United States Patent
Smith et al.

(10) Patent No.: US 12,258,412 B2
(45) Date of Patent: Mar. 25, 2025

(54) NUCLEIC ACID MOLECULES ENCODING BISPECIFIC ANTI-BCMA x ANTI-CD3 ANTIBODIES

(71) Applicant: Regeneron Pharmaceuticals, Inc., Tarrytown, NY (US)

(72) Inventors: Eric Smith, New York, NY (US); Kara Olson, White Plains, NY (US); Frank Delfino, Poughquag, NY (US); David DiLillo, New York, NY (US); Jessica Kirshner, New York, NY (US); Olga Sineshchekova, Pleasantville, NY (US); Qian Zhang, Lexington, MA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 122 days.

(21) Appl. No.: 17/828,847

(22) Filed: May 31, 2022

(65) Prior Publication Data
US 2022/0306758 A1    Sep. 29, 2022

Related U.S. Application Data

(63) Continuation of application No. 16/516,028, filed on Jul. 18, 2019, now Pat. No. 11,384,153.
(Continued)

(51) Int. Cl.
*C07K 16/28* (2006.01)
*A61K 39/00* (2006.01)
(Continued)

(52) U.S. Cl.
CPC ...... *C07K 16/2878* (2013.01); *A61K 39/4611* (2023.05); *A61K 39/464417* (2023.05);
(Continued)

(58) Field of Classification Search
None
See application file for complete search history.

(56) References Cited

U.S. PATENT DOCUMENTS

| | | |
|---|---|---|
| 6,737,056 B1 | 5/2004 | Presta |
| 7,083,785 B2 | 8/2006 | Browning et al. |

(Continued)

FOREIGN PATENT DOCUMENTS

| | | |
|---|---|---|
| AU | 2013340799 B2 | 11/2013 |
| CN | 107827989 | 3/2018 |

(Continued)

OTHER PUBLICATIONS

Abramson, "The Multiple Myeloma Drug Pipeline-2018: A Review of Small Molecules and Their Therapeutic Targets," The Multiple Myeloma Drug Pipeline, 1-19, (2018).
(Continued)

*Primary Examiner* — Claire Kaufman
(74) *Attorney, Agent, or Firm* — Schwabe, Williamson & Wyatt PC; Aparna Patankar

(57) ABSTRACT

B-cell maturation antigen (BCMA) is expressed on malignant plasma cells. The present invention provides novel bispecific antibodies (bsAbs) that bind to both BCMA and CD3 and activate T cells via the CD3 complex in the presence of BCMA-expressing tumor cells. In certain embodiments, the bispecific antigen-binding molecules of the present invention are capable of inhibiting the growth of tumors expressing BCMA. The bispecific antigen-binding molecules of the invention are useful for the treatment of diseases and disorders in which an upregulated or induced BCMA-targeted immune response is desired and/or therapeutically beneficial. For example, the bispecific antibodies
(Continued)

of the invention are useful for the treatment of various cancers, including multiple myeloma.

20 Claims, 7 Drawing Sheets

Specification includes a Sequence Listing.

Related U.S. Application Data

(60) Provisional application No. 62/793,645, filed on Jan. 17, 2019, provisional application No. 62/750,968, filed on Oct. 26, 2018, provisional application No. 62/700,596, filed on Jul. 19, 2018.

(51) Int. Cl.
  *C07K 16/46* (2006.01)
  *A61P 35/00* (2006.01)

(52) U.S. Cl.
  CPC .. *A61K 39/464429* (2023.05); *C07K 16/2809* (2013.01); *C07K 16/468* (2013.01); *A61K 2239/31* (2023.05); *A61K 2239/38* (2023.05); *A61K 2239/48* (2023.05); *A61P 35/00* (2018.01); *C07K 2317/31* (2013.01); *C07K 2317/76* (2013.01); *C07K 2317/92* (2013.01)

(56) References Cited

U.S. PATENT DOCUMENTS

| | | |
|---|---|---|
| 7,261,893 B2 | 8/2007 | Veldman et al. |
| 7,691,804 B2 | 4/2010 | Jeffrey et al. |
| 7,700,099 B2 | 4/2010 | Strohl |
| 8,193,322 B2 | 6/2012 | Yan et al. |
| 8,323,962 B2 | 12/2012 | Dall' Acqua et al. |
| 8,920,776 B2 | 12/2014 | Gaiger et al. |
| 9,034,324 B2 | 5/2015 | Kalled et al. |
| 9,150,664 B2 | 10/2015 | Kufer et al. |
| 9,243,058 B2 | 1/2016 | Armitage et al. |
| 9,273,141 B2 | 3/2016 | Algate et al. |
| 9,340,621 B2 | 5/2016 | Kufer et al. |
| 9,598,500 B2 | 3/2017 | Kufer et al. |
| 9,650,430 B2 | 5/2017 | Browning et al. |
| 9,657,102 B2 | 5/2017 | Smith et al. |
| 9,963,513 B2 | 5/2018 | Vu et al. |
| 9,969,809 B2 | 5/2018 | Kuo et al. |
| 10,040,860 B2 | 8/2018 | Kuo et al. |
| 10,072,088 B2 | 9/2018 | Pillarisetti et al. |
| 10,077,315 B2 | 9/2018 | Vu et al. |
| 10,144,782 B2 | 12/2018 | Oden et al. |
| 10,189,906 B2 | 1/2019 | Lipp et al. |
| 10,220,090 B2 | 3/2019 | Armitage et al. |
| 10,253,104 B2 | 4/2019 | Vu et al. |
| 11,124,577 B2 * | 9/2021 | Vu .................. C07K 16/2896 |
| 11,384,153 B2 | 7/2022 | Smith et al. |
| 2005/0244374 A1 | 11/2005 | Goebel et al. |
| 2013/0273055 A1 | 10/2013 | Borges et al. |
| 2014/0112914 A1 | 4/2014 | Nezu et al. |
| 2015/0023967 A1 | 1/2015 | Kufer et al. |
| 2015/0344583 A1 | 12/2015 | Armitage et al. |
| 2016/0176973 A1 | 6/2016 | Kufer et al. |
| 2017/0051074 A1 | 2/2017 | Kirshner et al. |
| 2017/0165373 A1 | 6/2017 | Armitage et al. |
| 2017/0209571 A1 | 7/2017 | Kanapuram et al. |
| 2017/0218077 A1 | 8/2017 | Raum et al. |
| 2017/0226216 A1 | 8/2017 | Morgan et al. |
| 2017/0233484 A1 | 8/2017 | Sussman et al. |
| 2017/0253670 A1 | 9/2017 | Klein et al. |
| 2017/0327580 A1 | 11/2017 | Vu et al. |
| 2018/0030148 A1 | 2/2018 | Algate et al. |
| 2018/0112384 A1 | 4/2018 | Rothleitner et al. |
| 2018/0118842 A1 | 5/2018 | Brentjens et al. |
| 2018/0147293 A1 | 5/2018 | Algate et al. |
| 2018/0171018 A1 | 6/2018 | Kuo et al. |
| 2018/0194850 A1 | 7/2018 | Faustman |
| 2018/0222991 A1 | 8/2018 | Vu et al. |
| 2018/0273605 A1 | 9/2018 | Browning et al. |
| 2018/0298108 A1 | 10/2018 | Kuo et al. |
| 2018/0360880 A1 | 12/2018 | Brentjens et al. |
| 2019/0023801 A1 | 1/2019 | Sussman et al. |
| 2019/0040152 A1 | 2/2019 | Kinneer et al. |
| 2019/0106499 A1 | 4/2019 | Lipp et al. |
| 2019/0112381 A1 | 4/2019 | Wesche et al. |
| 2019/0112382 A1 | 4/2019 | Oden et al. |
| 2019/0161552 A1 | 5/2019 | Kalled et al. |
| 2020/0048349 A1 | 2/2020 | Gaudet |
| 2020/0345843 A1 | 11/2020 | Asrat et al. |

FOREIGN PATENT DOCUMENTS

| | | |
|---|---|---|
| EP | 1975231 B1 | 8/2011 |
| EP | 2762496 A1 | 8/2014 |
| EP | 2762497 A1 | 8/2014 |
| EP | 2465871 B1 | 5/2015 |
| EP | 1210425 B2 | 6/2015 |
| EP | 1957533 B1 | 7/2015 |
| EP | 2982692 A1 | 2/2016 |
| EP | 1806143 B1 | 6/2016 |
| EP | 2982694 B1 | 6/2016 |
| EP | 3029068 A1 | 8/2016 |
| EP | 2552955 B1 | 5/2017 |
| EP | 2953974 B1 | 12/2017 |
| EP | 2647707 B1 | 9/2018 |
| EP | 3415531 A1 | 12/2018 |
| EP | 2780374 B1 | 8/2019 |
| EP | 2780375 B1 | 9/2019 |
| EP | 3572427 A1 | 11/2019 |
| EP | 3689908 A2 | 8/2020 |
| WO | 2012/066058 A1 | 5/2012 |
| WO | 2012/163805 A1 | 12/2012 |
| WO | 2013/072406 A1 | 5/2013 |
| WO | 2013/072415 A1 | 5/2013 |
| WO | 13/154760 A1 | 10/2013 |
| WO | 2014/047231 A1 | 3/2014 |
| WO | 2014/068079 A1 | 5/2014 |
| WO | 2014/089335 A2 | 6/2014 |
| WO | 2014/122143 A1 | 8/2014 |
| WO | 2017/129585 A1 | 8/2014 |
| WO | 2014/140248 A1 | 9/2014 |
| WO | 15/052538 A1 | 4/2015 |
| WO | 2015/166073 A1 | 11/2015 |
| WO | 2016/087531 A1 | 6/2016 |
| WO | 2016/090327 A2 | 6/2016 |
| WO | 2016/094304 A2 | 6/2016 |
| WO | 2016/166629 A1 | 10/2016 |
| WO | 2016/166630 A1 | 10/2016 |
| WO | 2017/031104 A1 | 2/2017 |
| WO | WO-2017053856 A1 * | 3/2017 ............. A61P 35/00 |
| WO | 2017/083511 A1 | 5/2017 |
| WO | 2017/093942 A1 | 6/2017 |
| WO | 2017/143069 A1 | 8/2017 |
| WO | 2017/173349 A1 | 10/2017 |
| WO | 2017/211900 A1 | 12/2017 |
| WO | 2018/009904 A2 | 1/2018 |
| WO | 2018/052503 A1 | 3/2018 |
| WO | 2018/067331 A1 | 4/2018 |
| WO | 2018/075359 A1 | 4/2018 |
| WO | 2018/083204 A1 | 5/2018 |
| WO | 2018/099978 A1 | 6/2018 |
| WO | 2018/119215 A9 | 6/2018 |
| WO | 2018/145075 A1 | 8/2018 |
| WO | 2018/151836 A1 | 8/2018 |
| WO | 2018/201051 A1 | 11/2018 |
| WO | 2018/204907 A1 | 11/2018 |
| WO | 2018/237037 A2 | 12/2018 |
| WO | 2019/149249 A1 | 8/2019 |
| WO | 2020/191346 A1 | 9/2020 |

OTHER PUBLICATIONS

Bluhm et al., "CAR T Cells with Enhanced Sensitivity to B Cell Maturation Antigen for the Targeting of B Cell Non-Hodgkin's

(56) References Cited

OTHER PUBLICATIONS

Lymphoma and Multiple Myeloma," American Society of Gene & Cell Therapy, Molecular Therapy, vol. 26 No. 8; 1-15 (2018). [https://doi.org/10.1016/j.ymthe.2018.06.012].

Dilillo et al., "REGN5458, a Bispecific BCMAxCD3 T Cell Engaging Antibody, Demonstrates Robust in Vitro and In Vivo Anti-Tumor Efficacy in Multiple Myeloma Models, Comparable to that of BCMA CAR T Cells," Myeloma: Pathophysiology and Preclinical studies, excluding therapy: poster I, Article 132: 1-5 (2018). XP-002794959.

Harrington et al., "Development of JCARH125: Optimization of a Fully Human Anti-Bcma CAR for Use in the Treatment of Multiple Myeloma," Blood 130 (Suppl. 1): 1813, 1-2 (2017). XP-002795011.

Hoffman et al., "B Cells, Antibodies, and More," American Society of Nephrology, vol. 11: 137-154 (2016). Doi: 10.2215/CJN.09430915.

Smith et al., "Development and Evaluation of an Optimal Human Single-Chain Variable Fragment-Derived BCMA-Targeted CAR T Cell Vector," Molecular Therapy, vol. 26(No. 6) 1447-1456 (2018). XP-002795010.

Tai et al., "Targeting B-cell maturation antigen in multiple myeloma," Future Medicine: Immunotherapy, vol. 7(11): 1187-1199 (2015).

U.S. Appl. No. 16/516,028, Non-Final Office Action mailed Sep. 14, 2021.

U.S. Appl. No. 16/516,028, Notice of Allowance mailed Feb. 28, 2022.

U.S. Appl. No. 16/516,028, Requirement for Restriction/Election mailed May 14, 2021.

WIPO Application No. PCT/US2019/042447, Invitation to Pay Additional Fees and, where applicable, Protest Fee mailed Oct. 23, 2019.

WIPO Application No. PCT/US2019/042447, PCT International Search Report and Written Opinion of the International Searching Authority mailed Dec. 20, 2019.

WIPO Application No. PCT/US2019/042452, Invitation to Pay Additional Fees and, where applicable, Protest Fee mailed Oct. 25, 2019.

WIPO Application No. PCT/US2019/042452, PCT International Search Report and Written Opinion of the International Searching Authority mailed Nov. 22, 2019.

U.S. Appl. No. 16/516,060, Requirement for Restriction/Election mailed May 10, 2023.

U.S. Appl. No. 16/516,060, Non-Final Office Action mailed Oct. 26, 2023.

U.S. Appl. No. 16/516,060, Notice of Allowance mailed Feb. 22, 2024.

U.S. Appl. No. 16/516,060, Notice of Allowance mailed Jul. 3, 2024.

* cited by examiner

NUCLEIC ACID MOLECULES ENCODING BISPECIFIC ANTI-BCMA x ANTI-CD3 ANTIBODIES

CROSS-REFERENCE TO RELATED APPLICATIONS

This application is a division of U.S. application Ser. No. 16/516,028, filed Jul. 18, 2019, which claims the benefit under 35 USC § 119(e) of U.S. Provisional Application No. 62/700,596, filed Jul. 19, 2018; 62/750,968, filed Oct. 26, 2018; and 62/793,645, filed Jan. 17, 2019, each of which is incorporated herein by reference in its entirety for all purposes.

REFERENCE TO A SEQUENCE LISTING

This application incorporates by reference the Sequence Listing submitted in Computer Readable Form as file 10452US02-Sequence, created on May 31, 2022 and containing 63,253 bytes.

FIELD OF THE INVENTION

The present invention relates to antibodies, and antigen-binding fragments thereof, which are specific for B-cell maturation antigen (BCMA), and methods of use thereof. The present invention includes bispecific antigen-binding molecules (e.g., bispecific antibodies) that bind BCMA and CD3, and methods of use thereof.

BACKGROUND

B-cell maturation antigen (BCMA), also known as TNFRSF17, or CD269, is a type III transmembrane protein lacking a signal peptide and containing a cysteine-rich extracellular domain. BCMA, along with closely related proteins, promotes B-cell survival at distinct stages of development. BCMA is expressed exclusively in B-cell lineage cells, particularly in the interfollicular region of the germinal center as well as on plasmablasts and differentiated plasma cells. BCMA is selectively induced during plasma cell differentiation, and is required for optimal survival of long-lived plasma cells in the bone marrow. In multiple myeloma, BCMA is widely expressed on malignant plasma cells at elevated levels, and BCMA expression is increased with progression from normal cells to active multiple myeloma. BCMA is also expressed in other B-cell malignancies, including Waldenström's macroglobulinemia, Burkitt lymphoma, and Diffuse Large B-Cell Lymphoma. Tai et al., *Immunotherapy*, 7(11):1187-1199, 2015.

CD3 is a homodimeric or heterodimeric antigen expressed on T cells in association with the T cell receptor complex (TCR) and is required for T cell activation. Functional CD3 is formed from the dimeric association of two of four different chains: epsilon, zeta, delta and gamma. The CD3 dimeric arrangements include gamma/epsilon, delta/epsilon and zeta/zeta. Antibodies against CD3 have been shown to cluster CD3 on T cells, thereby causing T cell activation in a manner similar to the engagement of the TCR by peptide-loaded MHC molecules. Thus, anti-CD3 antibodies have been proposed for therapeutic purposes involving the activation of T cells. In addition, bispecific antibodies that are capable of binding CD3 and a target antigen have been proposed for therapeutic uses involving targeting T cell immune responses to tissues and cells expressing the target antigen.

Antigen-binding molecules that target BCMA, including bispecific antigen-binding molecules that bind both BCMA and CD3 would be useful in therapeutic settings in which specific targeting and T cell-mediated killing of cells that express BCMA is desired.

BRIEF SUMMARY OF THE INVENTION

In one aspect, the present invention provides an isolated bispecific antigen binding molecule comprising: (a) a first antigen-binding domain that specifically binds a human B cell maturation antigen (BCMA) on a target tumor cell, with an $EC_{50}$ of less than about 100 nM as measured by an in vitro FACS binding assay; and (b) a second antigen-binding domain (D2) that specifically binds human CD3 with an $EC_{50}$ of less than about $10^{-6}$ M as measured by an in vitro FACS binding assay.

In some cases, the bispecific antigen binding molecule activates T cells in vitro with an $EC_{50}$ of less than about $10^{-9}$ M. In some cases, the bispecific antigen-binding molecule mediates in vitro T cell killing of tumor cell lines expressing BCMA with an $EC_{50}$ of less than about $10^{-9}$ M. In some cases, the bispecific antigen-binding molecule mediates in vitro autologous T cell killing of primary myeloma cells expressing BCMA with an $EC_{50}$ of less than about $10^{-8}$ M. In some embodiments, the bispecific antigen-binding molecule interacts with amino acid residues 1 through 43 of BCMA as set forth in SEQ ID NO: 115.

In some cases, the target tumor cell is a plasma cell. In some cases, the target tumor cell is from a patient suffering from multiple myeloma, or from another B-cell disorder characterized in part as having B cells expressing BCMA. In some cases, the bispecific antigen-binding molecule inhibits the proliferation of BCMA expressing tumor cells at a dose of from about 0.04 mg/kg to about 4.0 mg/kg. In some cases, the dose is 0.04 mg/kg, 0.4 mg/kg or 4 mg/kg. In some embodiments, the dose is administered to a patient in need thereof at least twice weekly for at least seven doses. In some cases, the bispecific antigen-binding molecule inhibits the proliferation of BCMA+ tumor cells selected from the group consisting of myeloma cells, lymphoma cells and leukemia cells. In some cases, the bispecific antigen-binding molecule inhibits the proliferation of BCMA+ tumor cells selected from the group consisting of H929 cells, MOLP-8 cells and OPM cells.

In some cases, the bispecific antigen-binding molecule cross-reacts with cynomolgus BCMA. In some cases, the bispecific antigen-binding molecule does not cross-react with cynomolgus BCMA.

In some embodiments, the isolated bispecific antigen binding molecule comprises a first antigen-binding domain that comprises: (a) three heavy chain complementarity determining regions (HCDR1, HCDR2 and HCDR3) contained within a heavy chain variable region (HCVR) comprising the amino acid sequence of SEQ ID NO: 66; and (b) three light chain complementarity determining regions (LCDR1, LCDR2 and LCDR3) contained within a light chain variable region (LCVR) comprising the amino acid sequence of SEQ ID NO:82. In some cases, the isolated bispecific antigen binding molecule comprises a HCDR1 comprising the amino acid sequence of SEQ ID NO:68, a HCDR2 comprising the amino acid sequence of SEQ ID NO:70, and a HCDR3 comprising the amino acid sequence of SEQ ID NO:72. In some cases, the isolated bispecific antigen-binding molecule comprises a LCDR1 comprising the amino acid sequence of SEQ ID NO:84, a LCDR2 comprising the amino acid sequence of SEQ ID NO:86, and a LCDR3 comprising the amino acid sequence of SEQ ID NO:88. In some cases, the first antigen-binding domain comprises a HCVR comprising the amino acid sequence of SEQ ID NO: 66, and a LCVR comprising the amino acid sequence of SEQ ID NO: 82.

In some embodiments, the isolated bispecific antigen-binding molecule comprises a second antigen-binding domain that comprises: (a) three heavy chain complementarity determining regions (HCDR1, HCDR2 and HCDR3) contained within a heavy chain variable region (HCVR) comprising the amino acid sequence of SEQ ID NO: 90 or SEQ ID NO: 98; and (b) three light chain complementarity determining regions (LCDR1, LCDR2 and LCDR3) contained within a light chain variable region (LCVR) comprising the amino acid sequence of SEQ ID NO:82. In some cases, the second antigen-binding domain comprises: (a) a HCDR1 comprising the amino acid sequence of SEQ ID NO: 92 or SEQ ID NO: 100; (b) a HCDR2 comprising the amino acid sequence of SEQ ID NO: 94 or SEQ ID NO: 102; and (c) a HCDR3 comprising the amino acid sequence of SEQ ID NO: 96 or SEQ ID NO: 104. In some cases, the second antigen-binding domain comprises a LCDR1 comprising the amino acid sequence of SEQ ID NO:84, a LCDR2 comprising the amino acid sequence of SEQ ID NO:86, and a LCDR3 comprising the amino acid sequence of SEQ ID NO:88. In some cases, the second antigen-binding domain comprises: (a) HCDR1, HCDR2, HCDR3 domains, respectively, comprising the amino acid sequences of SEQ ID NOs: 92, 94, 96; and LCDR1, LCDR2, LCDR3 domains, respectively, comprising the amino acid sequences of SEQ ID NOs: 84, 86, 88; or (b) HCDR1, HCDR2, HCDR3 domains, respectively, comprising the amino acid sequences of SEQ ID NOs: 100, 102, 104; and LCDR1, LCDR2, LCDR3 domains, respectively, comprising the amino acid sequences of SEQ ID NOs: 84, 86, 88. In some cases, the second antigen-binding domain comprises: (a) a HCVR comprising the amino acid sequence of SEQ ID NO: 90, and a LCVR comprising the amino acid sequence of SEQ ID NO: 82; or (b) a HCVR comprising the amino acid sequence of SEQ ID NO: 98, and a LCVR comprising the amino acid sequence of SEQ ID NO: 82.

In another aspect, the present invention provides an isolated bispecific antigen-binding molecule, comprising: (a) a first antigen-binding domain that comprises HCDR1, HCDR2, HCDR3 domains, respectively, comprising the amino acid sequences of SEQ ID NOs: 68, 70, 72, and LCDR1, LCDR2, LCDR3 domains, respectively, comprising the amino acid sequences of SEQ ID NOs: 84, 86, 88; and (b) a second antigen binding domain that comprises HCDR1, HCDR2, HCDR3 domains, respectively, comprising the amino acid sequences of SEQ ID NOs: 92, 94, 96, and LCDR1, LCDR2, LCDR3 domains, respectively, comprising the amino acid sequences of SEQ ID NOs: 84, 86, 88. In some cases, the isolated bispecific antigen-binding molecule comprises: (a) a first antigen binding domain that comprises a HCVR comprising the amino acid sequence of SEQ ID NO: 66, and a LCVR comprising the amino acid sequence of SEQ ID NO: 82; and (b) a second antigen binding domain that comprises a HCVR comprising the amino acid sequence of SEQ ID NO: 90, and a LCVR comprising the amino acid sequence of SEQ ID NO: 82.

In another aspect, the present invention provides an isolated bispecific antigen-binding molecule, comprising: (a) a first antigen-binding domain that comprises HCDR1, HCDR2, HCDR3 domains, respectively, comprising the amino acid sequences of SEQ ID NOs: 68, 70, 72, and LCDR1, LCDR2, LCDR3 domains, respectively, comprising the amino acid sequences of SEQ ID NOs: 84, 86, 88; and (b) a second antigen binding domain that comprises HCDR1, HCDR2, HCDR3 domains, respectively, comprising the amino acid sequences of SEQ ID NOs: 100, 102, 104, and LCDR1, LCDR2, LCDR3 domains, respectively, comprising the amino acid sequences of SEQ ID NOs: 84, 86, 88. In some cases, the isolated bispecific antigen-binding molecule comprises: (a) a first antigen binding domain that comprises a HCVR comprising the amino acid sequence of SEQ ID NO: 66, and a LCVR comprising the amino acid sequence of SEQ ID NO: 82; and (b) a second antigen binding domain that comprises a HCVR comprising the amino acid sequence of SEQ ID NO: 98, and a LCVR comprising the amino acid sequence of SEQ ID NO: 82.

In another aspect, the present invention provides an isolated bispecific antigen-binding molecule, comprising: (a) a first antigen-binding domain that specifically binds human BCMA, and comprises the CDRs of a HCVR comprising an amino acid sequence selected from the group consisting of SEQ ID NOs: 2, 18, 34, 50, 66, 122, and 124, and the CDRs of a LCVR comprising an amino acid sequence selected from the group consisting of SEQ ID NO: 10, 26, 42, 58, 74, 82, 123, and 125; and (b) a second antigen-binding domain that specifically binds human CD3. In some cases, the first antigen-binding domain comprises the CDRs from a HCVR/LCVR amino acid sequence pair selected from the group consisting of SEQ ID NOs: 2/10, 18/26, 34/42, 50/58, 66/74, 122/123, 124/125, 2/82, 18/82, 34/82, 50/82, 66/82, 122/82, and 124/82. In some cases, the first antigen-binding domain comprises HCDR1-HCDR2-HCDR3-LCDR1-LCDR2-LCDR3 domains, respectively, selected from the group consisting of SEQ ID NOs: 4-6-8-12-14-16, 20-22-24-28-30-32, 36-38-40-44-46-48, 52-54-56-60-62-64, 68-70-72-76-78-80, 4-6-8-84-86-88, 20-22-24-84-86-88, 36-38-40-84-86-88, 52-54-56-84-86-88, and 68-70-72-84-86-88. In some cases, the first antigen-binding domain comprises the a HCVR/LCVR amino acid sequence pair selected from the group consisting of SEQ ID NOs: 2/10, 18/26, 34/42, 50/58, 66/74, 122/123, 124/125, 2/82, 18/82, 34/82, 50/82, 66/82, 122/82, and 124/82. In some cases, the second antigen-binding domain comprises the CDRs of a HCVR/LCVR amino acid sequence pair selected from the group consisting of SEQ ID NOs: 90/82 and 98/82.

In another aspect, the present invention provides an isolated bispecific antigen binding molecule that competes for binding to BCMA, or binds to the same epitope on BCMA as a reference antibody, wherein the reference antibody comprises a first antigen-binding domain comprising an HCVR/LCVR pair comprising the amino acid sequences of SEQ ID NOs: 66/82 and a second antigen-binding domain comprising an HCVR/LCVR pair comprising the amino acid sequences of either SEQ ID NOs: 90/82 or SEQ ID NOs: 98/82.

In another aspect, the present invention provides an isolated bispecific antigen binding molecule that competes for binding to human CD3, or binds to the same epitope on human CD3 as a reference antibody, wherein the reference antibody comprises a first antigen-binding domain comprising an HCVR/LCVR pair comprising the amino acid sequences of SEQ ID NOs: 66/82 and a second antigen-binding domain comprising an HCVR/LCVR pair comprising the amino acid sequences of either SEQ ID NOs: 90/82 or SEQ ID NOs: 98/82.

Any of the bispecific antigen-binding molecules discussed above or herein may be a bispecific antibody. In some cases, the bispecific antibody comprises a human IgG heavy chain constant region. In some cases, the human IgG heavy chain constant region is isotype IgG1. In some cases, the human IgG heavy chain constant region is isotype IgG4. In various embodiments, the bispecific antibody comprises a chimeric hinge that reduces Fcγ receptor binding relative to a wild-type hinge of the same isotype.

In another aspect, the present invention provides a pharmaceutical composition comprising the bispecific antigen-binding molecule (e.g., bispecific antibody) discussed above or herein, and a pharmaceutically acceptable carrier or diluent.

In another aspect, the present invention provides a nucleic acid molecule comprising a nucleotide sequence encoding a bispecific antigen-binding molecule (e.g., bispecific antibody) discussed above or herein.

In another aspect, the present invention provides an expression vector comprising the nucleic acid molecule discussed above.

In another aspect, the present invention provides a host cell comprising the expression vector discussed above.

In another aspect, the present invention provides a method of inhibiting growth of a plasma cell tumor in a subject, comprising administering an isolated bispecific antigen-binding molecule, or a pharmaceutical composition comprising the bispecific antigen-binding molecule, as discussed above or herein, to the subject. In some cases, the plasma cell tumor is multiple myeloma. In some cases, the method further comprises administering a second therapeutic agent, or therapeutic regimen. In some embodiments, the second therapeutic agent comprises an anti-tumor agent (e.g. chemotherapeutic agents including melphalan, vincristine (Oncovin), cyclophosphamide (Cytoxan), etoposide (VP-16), doxorubicin (Adriamycin), liposomal doxorubicin (Doxil), obendamustine (Treanda), or any others known to be effective in treating a plasma cell tumor in a subject.). In some embodiments, the second therapeutic agent comprises steroids. In some embodiments, the second therapeutic agent comprises targeted therapies including thalidomide, lenalidomide, and bortezomib, which are therapies approved to treat newly diagnosed patients. Lenalidomide, pomalidornide, bortezomib, carfilzomib, panobinostat, ixazornib, elotuzumab, and daratumumab are examples of a second therapeutic agent effective for treating recurrent myeloma. In certain embodiments the second therapeutic agent is a regimen comprising radiotherapy or a stem cell transplant. In certain embodiments, the second therapeutic agent may be an immunomodulatory agent. In certain embodiments, the second therapeutic agent may be a proteasome inhibitor; including bortezomib (Velcade), carfilzomib (Kyprolis), ixazomib (Ninlaro). In certain embodiments the second therapeutic agent may be a histone deacetylase inhibitor such as panobinostat (Farydak). In certain embodiments, the second therapeutic agent may be a monoclonal antibody, an antibody drug conjugate, a bispecific antibody conjugated to an anti-tumor agent, a checkpoint inhibitor, or combinations thereof.

In another aspect, the present invention provides a method of treating a patient suffering from multiple myeloma, or from another BCMA-expressing B cell malignancy, where the method comprises administering an isolated bispecific antigen-binding molecule or a pharmaceutical composition comprising the bispecific antigen-binding molecule, as discussed above or herein, to the subject. In some cases, the BCMA-expressing B cell malignancy is selected from the group consisting of Waldenström's macroglobulinemia, Burkitt's lymphoma and Diffuse Large B-Cell lymphoma, Non-Hodgkin's lymphoma, chronic lymphocytic leukemia, follicular lymphoma, mantle cell lymphoma, marginal zone lymphoma, lymphoplasmacytic lymphoma, and Hodgkin's lymphoma. In some cases, the method further comprises administering a second therapeutic agent. In some embodiments, the second therapeutic agent comprises an anti-tumor agent (a chemotherapeutic agent), DNA alkylators, immunomodulators, proteasome inhibitors, histone deacetylase inhibitors radiotherapy, a stem cell transplant, an immunomodulator, a monoclonal antibody that interacts with an antigen expressed on the tumor cell surface, a monoclonal antibody other than those described herein, which may interact with a different antigen on the plasma cell surface, a bispecific antibody, which has one arm that binds to an antigen on the tumor cell surface and the other arm binds to an antigen on a T cell, an antibody drug conjugate, a bispecific antibody conjugated with an anti-tumor agent, a checkpoint inhibitor, for example, one that targets, PD-1 or CTLA-4, or combinations thereof. In certain embodiments, the checkpoint inhibitors may be selected from PD-1 inhibitors, such as pembrolizumab (Keytruda), nivolumab (Opdivo), or cemiplimab (REGN2810). In certain embodiments, the checkpoint inhibitors may be selected from PD-L1 inhibitors, such as atezolizumab (Tecentriq), avelumab (Bavencio), or Durvalumab (Imfinzi)). In certain embodiments, the checkpoint inhibitors may be selected from CTLA-4 inhibitors, such as ipilimumab (Yervoy). Other combinations that may be used in conjunction with an antibody of the invention are described above.

In another aspect, the present invention provides a method of treating a patient suffering from a BCMA-expressing tumor, wherein the method comprises administering an isolated bispecific antigen-binding molecule as discussed above or herein, or a pharmaceutical composition comprising same, to the subject in combination with an anti-PD-1 antibody or antigen-binding fragment thereof. In some cases, the anti-PD-1 antibody or antigen-binding fragment is an anti-PD-1 antibody. In some embodiments, the anti-PD-1 antibody is cemiplimab (REGN2810). In various embodiments, the combination of anti-BCMA×anti-CD3 bispecific antigen-binding molecule (e.g., a bispecific antibody) and an anti-PD-1 antibody or antigen-binding fragment (e.g., an anti-PD-1 antibody) produces a synergistic therapeutic effect in the treatment of BCMA-expressing tumors.

In another aspect, the present invention provides for use of the bispecific antigen-binding molecules discussed above or herein, or the pharmaceutical compositions discussed above or herein, in the treatment of a disease or disorder associated with expression of BCMA. In some cases, the disease or disorder is cancer. In some embodiments, the cancer is multiple myeloma. In some cases, the disease or disorder is Castleman disease. In some cases, the antigen-binding molecules are for use in combination with an anti-PD-1 antibody or antigen-binding fragment thereof, optionally wherein the anti-PD-1 antibody is cemiplimab (REGN2810).

The present invention further includes use of the bispecific antigen-binding molecules discussed above or herein in the manufacture of a medicament for treating a disease or disorder associated with expression of BCMA. In some cases, the disease or disorder is cancer. In some embodiments, the cancer is multiple myeloma.

In various embodiments, any of the features or components of embodiments discussed above or herein may be combined, and such combinations are encompassed within the scope of the present disclosure. Any specific value discussed above or herein may be combined with another related value discussed above or herein to recite a range with the values representing the upper and lower ends of the range, and such ranges are encompassed within the scope of the present disclosure.

Other embodiments will become apparent from a review of the ensuing detailed description.

DETAILED DESCRIPTION

Figure 1:
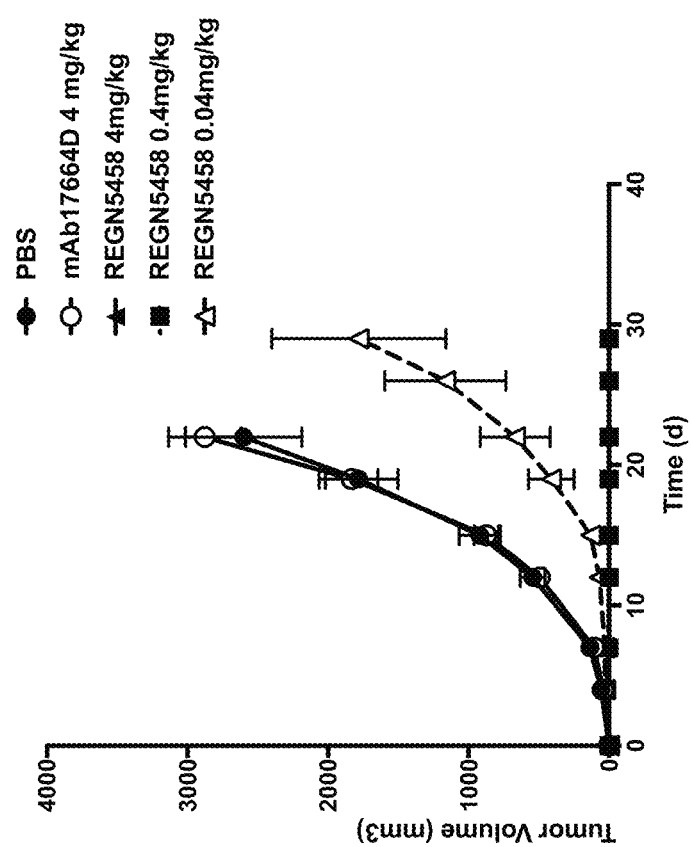
FIGS. 1 and 2 illustrate prophylactic dose-dependent tumor inhibition of BCMA-expressing NCI-H929 human multiple myeloma tumor cells in vivo by anti-BCMA×anti-CD3 bispecific antibodies REGN5458 and REGN5459, respectively. NCI-H929 cells express high levels of BCMA.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expression "CD3," as used herein, refers to an antigen which is expressed on T cells as part of the multimolecular T cell receptor (TCR) and which consists of a homodimer or heterodimer formed from the association of two of four receptor chains: CD3-epsilon, CD3-delta, CD3-zeta, and CD3-gamma. Human CD3-epsilon comprises the amino acid sequence as set forth in SEQ ID NO:116; human CD3-delta comprises the amino acid sequence as set forth in SEQ ID NO:117; human CD3-zeta comprises the amino acid sequence as set forth in SEQ ID NO: 118; and CD3-gamma comprises the amino acid sequence as set forth in SEQ ID NO 119. All references to proteins, polypeptides and protein fragments herein are intended to refer to the human version of the respective protein, polypeptide or protein fragment unless explicitly specified as being from a non-human species. Thus, the expression "CD3" means human CD3 unless specified as being from a non-human species, e.g., "mouse CD3," "monkey CD3," etc.

As used herein, "an antibody that binds CD3" or an "anti-CD3 antibody" includes antibodies and antigen-binding fragments thereof that specifically recognize a single CD3 subunit (e.g., epsilon, delta, gamma or zeta), as well as antibodies and antigen-binding fragments thereof that specifically recognize a dimeric complex of two CD3 subunits (e.g., gamma/epsilon, delta/epsilon, and zeta/zeta CD3 dimers). The antibodies and antigen-binding fragments of the present invention may bind soluble CD3 and/or cell surface expressed CD3. Soluble CD3 includes natural CD3 proteins as well as recombinant CD3 protein variants such as, e.g., monomeric and dimeric CD3 constructs, that lack a transmembrane domain or are otherwise unassociated with a cell membrane.

As used herein, the expression "cell surface-expressed CD3" means one or more CD3 protein(s) that is/are expressed on the surface of a cell in vitro or in vivo, such that at least a portion of a CD3 protein is exposed to the extracellular side of the cell membrane and is accessible to an antigen-binding portion of an antibody. "Cell surface-expressed CD3" includes CD3 proteins contained within the context of a functional T cell receptor in the membrane of a cell. The expression "cell surface-expressed CD3" includes CD3 protein expressed as part of a homodimer or heterodimer on the surface of a cell (e.g., gamma/epsilon, delta/epsilon, and zeta/zeta CD3 dimers). The expression, "cell surface-expressed CD3" also includes a CD3 chain (e.g., CD3-epsilon, CD3-delta or CD3-gamma) that is expressed by itself, without other CD3 chain types, on the surface of a cell. A "cell surface-expressed CD3" can comprise or consist of a CD3 protein expressed on the surface of a cell which normally expresses CD3 protein. Alternatively, "cell surface-expressed CD3" can comprise or consist of CD3 protein expressed on the surface of a cell that normally does not express human CD3 on its surface but has been artificially engineered to express CD3 on its surface.

The expression "BCMA," as used herein, refers to B-cell maturation antigen. BCMA (also known as TNFRSF17 and CD269) is a cell surface protein expressed on malignant plasma cells, and plays a central role in regulating B cell maturation and differentiation into immunoglobulin-producing plasma cells. The amino acid sequence of human BCMA is shown in SEQ ID NO: 115, and can also be found in GenBank accession number NP 001183.2.

As used herein, "an antibody that binds BCMA" or an "anti-BCMA antibody" includes antibodies and antigen-binding fragments thereof that specifically recognize BCMA.

The term "antigen-binding molecule" includes antibodies and antigen-binding fragments of antibodies, including, e.g., bispecific antibodies.

The term "antibody", as used herein, means any antigen-binding molecule or molecular complex comprising at least one complementarity determining region (CDR) that specifically binds to or interacts with a particular antigen (e.g., BCMA or CD3). The term "antibody" includes immunoglobulin molecules comprising four polypeptide chains, two heavy (H) chains and two light (L) chains inter-connected by disulfide bonds, as well as multimers thereof (e.g., IgM). The term "antibody" also includes immunoglobulin molecules consisting of four polypeptide chains, two heavy (H) chains and two light (L) chains inter-connected by disulfide bonds. Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-BCMA antibody or anti-CD3 antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (V) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

In certain embodiments of the invention, the anti-BCMA monospecific antibodies or anti-BCMA×anti-CD3 bispecific antibodies of the invention are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies of the invention may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The present invention also includes one-arm antibodies that bind BCMA. As used herein, a "one-arm antibody" means an antigen-binding molecule comprising a single antibody heavy chain and a single antibody light chain. The one-arm antibodies of the present invention may comprise any of the HCVR/LCVR or CDR amino acid sequences as set forth in Table 1.

The anti-BCMA or anti-BCMAxanti-CD3 antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-BCMA or anti-BCMA×anti-CD3 antibodies comprising variants of any of the HCVR, LCVR, and/or CDR amino acid sequences disclosed herein having one or more conservative substitutions. For example, the present invention includes anti-BCMA or anti-BCMA×anti-CD3 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Tables 1 and 3 herein, or the anti-CD3 antibodies disclosed in WO 2014/047231 or WO 2017/053856, each of which is incorporated herein by reference.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

Germline Mutations

The anti-CD3 antibodies disclosed herein comprise one or more amino acid substitutions, insertions and/or deletions in the framework and/or CDR regions of the heavy chain variable domains as compared to the corresponding germline sequences from which the antibodies were derived.

The present invention also includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"), and having weak or no detectable binding to a CD3 antigen.

Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be tested for one or more desired properties such as, improved binding specificity, weak or reduced binding affinity, improved or enhanced pharmacokinetic properties, reduced immunogenicity, etc. Antibodies and antigen-binding fragments obtained in this general manner given the guidance of the present disclosure are encompassed within the present invention.

The present invention also includes antigen-binding molecules comprising an antigen-binding domain with an HCVR and/or CDR amino acid sequence that is substantially identical to any of the HCVR and/or CDR amino acid sequences disclosed herein, while maintaining or improving the desired weak affinity to CD3 antigen. The term "substantial identity" or "substantially identical," when referring to an amino acid sequence means that two amino acid sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402.

Binding Properties of the Antibodies

As used herein, the term "binding" in the context of the binding of an antibody, immunoglobulin, antibody-binding fragment, or Fc-containing protein to either, e.g., a predetermined antigen, such as a cell surface protein or fragment thereof, typically refers to an interaction or association between a minimum of two entities or molecular structures, such as an antibody-antigen interaction.

For instance, binding affinity typically corresponds to a $K_D$ value of about $10^{-7}$ M or less, such as about $10^{-8}$ M or less, such as about $10^{-9}$ M or less when determined by, for instance, surface plasmon resonance (SPR) technology in a BIAcore 3000 instrument using the antigen as the ligand and the antibody, Ig, antibody-binding fragment, or Fc-containing protein as the analyte (or antiligand). Cell-based binding strategies, such as fluorescent-activated cell sorting (FACS) binding assays, are also routinely used, and FACS data correlates well with other methods such as radioligand competition binding and SPR (Benedict, C A, J Immunol Methods. 1997, 201(2):223-31; Geuijen, C A, et al. J Immunol Methods. 2005, 302(1-2):68-77).

Accordingly, the antibody or antigen-binding protein of the invention binds to the predetermined antigen or cell surface molecule (receptor) having an affinity corresponding to a $K_D$ value that is at least ten-fold lower than its affinity for binding to a non-specific antigen (e.g., BSA, casein). According to the present invention, the affinity of an antibody corresponding to a $K_D$ value that is equal to or less than ten-fold lower than a non-specific antigen may be considered non-detectable binding, however such an antibody may be paired with a second antigen binding arm for the production of a bispecific antibody of the invention.

The term "$K_D$" (M) refers to the dissociation equilibrium constant of a particular antibody-antigen interaction, or the dissociation equilibrium constant of an antibody or antibody-binding fragment binding to an antigen. There is an inverse relationship between $K_D$ and binding affinity, therefore the smaller the $K_D$ value, the higher, i.e. stronger, the affinity. Thus, the terms "higher affinity" or "stronger affinity" relate to a higher ability to form an interaction and therefore a smaller $K_D$ value, and conversely the terms "lower affinity" or "weaker affinity" relate to a lower ability to form an interaction and therefore a larger $K_D$ value. In some circumstances, a higher binding affinity (or $K_D$) of a particular molecule (e.g. antibody) to its interactive partner molecule (e.g. antigen X) compared to the binding affinity of the molecule (e.g. antibody) to another interactive partner molecule (e.g. antigen Y) may be expressed as a binding ratio determined by dividing the larger $K_D$ value (lower, or weaker, affinity) by the smaller $K_D$ (higher, or stronger, affinity), for example expressed as 5-fold or 10-fold greater binding affinity, as the case may be.

The term "$k_d$" (sec-1 or 1/s) refers to the dissociation rate constant of a particular antibody-antigen interaction, or the dissociation rate constant of an antibody or antibody-binding fragment. Said value is also referred to as the $k_{off}$ value.

The term "$k_a$" (M-1×sec-1 or 1/M) refers to the association rate constant of a particular antibody-antigen interaction, or the association rate constant of an antibody or antibody-binding fragment.

The term "$K_A$" (M-1 or 1/M) refers to the association equilibrium constant of a particular antibody-antigen interaction, or the association equilibrium constant of an antibody or antibody-binding fragment. The association equilibrium constant is obtained by dividing the $k_a$ by the $k_d$.

The term "EC50" or "$EC_{50}$" refers to the half maximal effective concentration, which includes the concentration of an antibody which induces a response halfway between the baseline and maximum after a specified exposure time. The $EC_{50}$ essentially represents the concentration of an antibody where 50% of its maximal effect is observed. In certain embodiments, the $EC_{50}$ value equals the concentration of an antibody of the invention that gives half-maximal binding to cells expressing CD3 or tumor-associated antigen (e.g., BCMA), as determined by e.g. a FACS binding assay. Thus, reduced or weaker binding is observed with an increased $EC_{50}$, or half maximal effective concentration value.

In one embodiment, decreased binding can be defined as an increased $EC_{50}$ antibody concentration which enables binding to the half-maximal amount of target cells.

In another embodiment, the $EC_{50}$ value represents the concentration of an antibody of the invention that elicits half-maximal depletion of target cells by T cell cytotoxic activity. Thus, increased cytotoxic activity (e.g. T cell-mediated tumor cell killing) is observed with a decreased $EC_{50}$, or half maximal effective concentration value.

Bispecific Antigen-Binding Molecules

The antibodies of the present invention may be monospecific, bi-specific, or multispecific. Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-BCMA monospecific antibodies or anti-BCMA×anti-CD3 bispecific antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second or additional binding specificity.

Use of the expression "anti-CD3 antibody" or "anti-BCMA antibody" herein is intended to include both monospecific anti-CD3 or anti-BCMA antibodies as well as bispecific antibodies comprising a CD3-binding arm and a BCMA-binding arm. Thus, the present invention includes bispecific antibodies wherein one arm of an immunoglobulin binds human CD3, and the other arm of the immunoglobulin is specific for human BCMA. The CD3-binding arm can comprise any of the HCVR/LCVR or CDR amino acid sequences as set forth in Table 3 herein, or the anti-CD3 antibodies disclosed in WO 2014/047231 or WO 2017/053856.

In certain embodiments, the CD3-binding arm binds to human CD3 and induces human T cell activation. In certain embodiments, the CD3-binding arm binds weakly to human CD3 and induces human T cell activation. In other embodiments, the CD3-binding arm binds weakly to human CD3 and induces tumor-associated antigen-expressing cell killing in the context of a bispecific or multispecific antibody. In other embodiments, the CD3-binding arm binds or associates weakly with human and cynomolgus (monkey) CD3, yet the binding interaction is not detectable by in vitro assays known in the art. The BCMA-binding arm can comprise any of the HCVR/LCVR or CDR amino acid sequences as set forth in Table 1 herein.

According to certain exemplary embodiments, the present invention includes bispecific antigen-binding molecules that specifically bind CD3 and BCMA. Such molecules may be referred to herein as, e.g., "anti-BCMA×anti-CD3" or "anti-CD3/anti-BCMA," or "anti-CD3×BCMA" or "CD3× BCMA" bispecific molecules, or other similar terminology (e.g., anti-BCMA/anti-CD3).

The term "BCMA," as used herein, refers to the human BCMA protein unless specified as being from a non-human species (e.g., "mouse BCMA," "monkey BCMA," etc.). The human BCMA protein has the amino acid sequence shown in SEQ ID NO: 115.

The aforementioned bispecific antigen-binding molecules that specifically bind CD3 and BCMA may comprise an anti-CD3 antigen-binding molecule which binds to CD3 with a weak binding affinity such as exhibiting a $K_D$ of greater than about 40 nM, as measured by an in vitro affinity binding assay.

As used herein, the expression "antigen-binding molecule" means a protein, polypeptide or molecular complex comprising or consisting of at least one complementarity determining region (CDR) that alone, or in combination with one or more additional CDRs and/or framework regions (FRs), specifically binds to a particular antigen. In certain embodiments, an antigen-binding molecule is an antibody or a fragment of an antibody, as those terms are defined elsewhere herein.

As used herein, the expression "bispecific antigen-binding molecule" means a protein, polypeptide or molecular complex comprising at least a first antigen-binding domain and a second antigen-binding domain. Each antigen-binding domain within the bispecific antigen-binding molecule comprises at least one CDR that alone, or in combination with one or more additional CDRs and/or FRs, specifically binds to a particular antigen. In the context of the present invention, the first antigen-binding domain specifically binds a first antigen (e.g., BCMA), and the second antigen-binding domain specifically binds a second, distinct antigen (e.g., CD3).

In certain exemplary embodiments of the present invention, the bispecific antigen-binding molecule is a bispecific antibody. Each antigen-binding domain of a bispecific antibody comprises a heavy chain variable domain (HCVR) and a light chain variable domain (LCVR). In the context of a bispecific antigen-binding molecule comprising a first and a second antigen-binding domain (e.g., a bispecific antibody), the CDRs of the first antigen-binding domain may be designated with the prefix "D1" and the CDRs of the second antigen-binding domain may be designated with the prefix "D2". Thus, the CDRs of the first antigen-binding domain may be referred to herein as D1-HCDR1, D1-HCDR2, and D1-HCDR3; and the CDRs of the second antigen-binding domain may be referred to herein as D2-HCDR1, D2-HCDR2, and D2-HCDR3.

In certain exemplary embodiments, the isolated bispecific antigen binding molecule comprises a first antigen-binding domain that comprises: (a) three heavy chain complementarity determining regions (HCDR1, HCDR2 and HCDR3) contained within a heavy chain variable region (HCVR) comprising the amino acid sequence of SEQ ID NO: 66; and (b) three light chain complementarity determining regions (LCDR1, LCDR2 and LCDR3) contained within a light chain variable region (LCVR) comprising the amino acid sequence of SEQ ID NO:82. In some cases, the isolated bispecific antigen binding molecule comprises a HCDR1 comprising the amino acid sequence of SEQ ID NO:68, a HCDR2 comprising the amino acid sequence of SEQ ID NO:70, and a HCDR3 comprising the amino acid sequence of SEQ ID NO:72. In some cases, the isolated bispecific antigen-binding molecule comprises a LCDR1 comprising the amino acid sequence of SEQ ID NO:84, a LCDR2 comprising the amino acid sequence of SEQ ID NO:86, and a LCDR3 comprising the amino acid sequence of SEQ ID NO:88. In some cases, the first antigen-binding domain comprises a HCVR comprising the amino acid sequence of SEQ ID NO: 66, and a LCVR comprising the amino acid sequence of SEQ ID NO: 82.

In certain exemplary embodiments, the isolated bispecific antigen-binding molecule comprises a second antigen-binding domain that comprises: (a) three heavy chain complementarity determining regions (HCDR1, HCDR2 and HCDR3) contained within a heavy chain variable region (HCVR) comprising the amino acid sequence of SEQ ID NO: 90 or SEQ ID NO: 98; and (b) three light chain complementarity determining regions (LCDR1, LCDR2 and LCDR3) contained within a light chain variable region (LCVR) comprising the amino acid sequence of SEQ ID NO:82. In some cases, the second antigen-binding domain comprises: (a) a HCDR1 comprising the amino acid sequence of SEQ ID NO: 92 or SEQ ID NO: 100; (b) a HCDR2 comprising the amino acid sequence of SEQ ID NO: 94 or SEQ ID NO: 102; and (c) a HCDR3 comprising the amino acid sequence of SEQ ID NO: 96 or SEQ ID NO: 104. In some cases, the second antigen-binding domain comprises a LCDR1 comprising the amino acid sequence of SEQ ID NO:84, a LCDR2 comprising the amino acid sequence of SEQ ID NO:86, and a LCDR3 comprising the amino acid sequence of SEQ ID NO:88. In some cases, the second antigen-binding domain comprises: (a) HCDR1, HCDR2, HCDR3 domains, respectively, comprising the amino acid sequences of SEQ ID NOs: 92, 94, 96; and LCDR1, LCDR2, LCDR3 domains, respectively, comprising the amino acid sequences of SEQ ID NOs: 84, 86, 88; or (b) HCDR1, HCDR2, HCDR3 domains, respectively, comprising the amino acid sequences of SEQ ID NOs: 100, 102, 104; and LCDR1, LCDR2, LCDR3 domains, respectively, comprising the amino acid sequences of SEQ ID NOs: 84, 86, 88. In some cases, the second antigen-binding domain comprises: (a) a HCVR comprising the amino acid sequence of SEQ ID NO: 90, and a LCVR comprising the amino acid sequence of SEQ ID NO: 82; or (b) a HCVR comprising the amino acid sequence of SEQ ID NO: 98, and a LCVR comprising the amino acid sequence of SEQ ID NO: 82.

In certain exemplary embodiments, the isolated bispecific antigen-binding molecule comprises: (a) a first antigen-binding domain that comprises HCDR1, HCDR2, HCDR3 domains, respectively, comprising the amino acid sequences of SEQ ID NOs: 68, 70, 72, and LCDR1, LCDR2, LCDR3 domains, respectively, comprising the amino acid sequences of SEQ ID NOs: 84, 86, 88; and (b) a second antigen binding domain that comprises HCDR1, HCDR2, HCDR3 domains, respectively, comprising the amino acid sequences of SEQ ID NOs: 92, 94, 96, and LCDR1, LCDR2, LCDR3 domains, respectively, comprising the amino acid sequences of SEQ ID NOs: 84, 86, 88. In some cases, the isolated bispecific antigen-binding molecule comprises: (a) a first antigen binding domain that comprises a HCVR comprising the amino acid sequence of SEQ ID NO: 66, and a LCVR comprising the amino acid sequence of SEQ ID NO: 82; and (b) a second antigen binding domain that comprises a HCVR comprising the amino acid sequence of SEQ ID NO: 90, and a LCVR comprising the amino acid sequence of SEQ ID NO: 82.

In certain exemplary embodiments, the isolated bispecific antigen-binding molecule comprises: (a) a first antigen-binding domain that comprises HCDR1, HCDR2, HCDR3 domains, respectively, comprising the amino acid sequences of SEQ ID NOs: 68, 70, 72, and LCDR1, LCDR2, LCDR3 domains, respectively, comprising the amino acid sequences of SEQ ID NOs: 84, 86, 88; and (b) a second antigen binding domain that comprises HCDR1, HCDR2, HCDR3 domains, respectively, comprising the amino acid sequences of SEQ ID NOs: 100, 102, 104, and LCDR1, LCDR2, LCDR3 domains, respectively, comprising the amino acid sequences of SEQ ID NOs: 84, 86, 88. In some cases, the isolated bispecific antigen-binding molecule comprises: (a) a first antigen binding domain that comprises a HCVR comprising the amino acid sequence of SEQ ID NO: 66, and a LCVR comprising the amino acid sequence of SEQ ID NO: 82; and (b) a second antigen binding domain that comprises a HCVR comprising the amino acid sequence of SEQ ID NO: 98, and a LCVR comprising the amino acid sequence of SEQ ID NO: 82.

In certain exemplary embodiments, the isolated bispecific antigen-binding molecule comprises: (a) a first antigen-binding domain that specifically binds human BCMA, and comprises the CDRs of a HCVR comprising an amino acid sequence selected from the group consisting of SEQ ID NOs: 2, 18, 34, 50, 66, 122, and 124, and the CDRs of a LCVR comprising an amino acid sequence selected from the group consisting of SEQ ID NO: 10, 26, 42, 58, 74, 82, 123, and 125; and (b) a second antigen-binding domain that specifically binds human CD3. In some cases, the first antigen-binding domain comprises the CDRs from a HCVR/LCVR amino acid sequence pair selected from the group consisting of SEQ ID NOs: 2/10, 18/26, 34/42, 50/58, 66/74, 122/123, 124/125, 2/82, 18/82, 34/82, 50/82, 66/82, 122/82, and 124/82. In some cases, the first antigen-binding domain comprises HCDR1-HCDR2-HCDR3-LCDR1-LCDR2-LCDR3 domains, respectively, selected from the group consisting of SEQ ID NOs: 4-6-8-12-14-16, 20-22-24-28-30-32, 36-38-40-44-46-48, 52-54-56-60-62-64, 68-70-72-76-78-80, 4-6-8-84-86-88, 20-22-24-84-86-88, 36-38-40-84-86-88, 52-54-56-84-86-88, and 68-70-72-84-86-88. In some cases, the first antigen-binding domain comprises the a HCVR/LCVR amino acid sequence pair selected from the group consisting of SEQ ID NOs: 2/10, 18/26, 34/42, 50/58, 66/74, 122/123, 124/125, 2/82, 18/82, 34/82, 50/82, 66/82, 122/82, and 124/82. In some cases, the second antigen-binding domain comprises the CDRs of a HCVR/LCVR amino acid sequence pair selected from the group consisting of SEQ ID NOs: 90/82 and 98/82.

In certain exemplary embodiments, the isolated bispecific antigen binding molecule competes for binding to BCMA, or binds to the same epitope on BCMA as a reference antibody, wherein the reference antibody comprises a first antigen-binding domain comprising an HCVR/LCVR pair comprising the amino acid sequences of SEQ ID NOs: 66/82 and a second antigen-binding domain comprising an HCVR/LCVR pair comprising the amino acid sequences of either SEQ ID NOs: 90/82 or SEQ ID NOs: 98/82.

In certain exemplary embodiments, the isolated bispecific antigen binding molecule competes for binding to human CD3, or binds to the same epitope on human CD3 as a reference antibody, wherein the reference antibody comprises a first antigen-binding domain comprising an HCVR/LCVR pair comprising the amino acid sequences of SEQ ID NOs: 66/82 and a second antigen-binding domain comprising an HCVR/LCVR pair comprising the amino acid sequences of either SEQ ID NOs: 90/82 or SEQ ID NOs: 98/82.

The bispecific antigen-binding molecules discussed above or herein may be bispecific antibodies. In some cases, the bispecific antibody comprises a human IgG heavy chain constant region. In some cases, the human IgG heavy chain constant region is isotype IgG1. In some cases, the human IgG heavy chain constant region is isotype IgG4. In various embodiments, the bispecific antibody comprises a chimeric hinge that reduces Fcγ receptor binding relative to a wild-type hinge of the same isotype.

The first antigen-binding domain and the second antigen-binding domain may be directly or indirectly connected to one another to form a bispecific antigen-binding molecule of the present invention. Alternatively, the first antigen-binding domain and the second antigen-binding domain may each be connected to a separate multimerizing domain. The association of one multimerizing domain with another multimerizing domain facilitates the association between the two antigen-binding domains, thereby forming a bispecific antigen-binding molecule. As used herein, a "multimerizing domain" is any macromolecule, protein, polypeptide, peptide, or amino acid that has the ability to associate with a second multimerizing domain of the same or similar structure or constitution. For example, a multimerizing domain may be a polypeptide comprising an immunoglobulin $C_H3$ domain. A non-limiting example of a multimerizing component is an Fc portion of an immunoglobulin (comprising a $C_H2$-$C_H3$ domain), e.g., an Fc domain of an IgG selected from the isotypes IgG1, IgG2, IgG3, and IgG4, as well as any allotype within each isotype group.

Bispecific antigen-binding molecules of the present invention will typically comprise two multimerizing domains, e.g., two Fc domains that are each individually part of a separate antibody heavy chain. The first and second multimerizing domains may be of the same IgG isotype such as, e.g., IgG1/IgG1, IgG2/IgG2, IgG4/IgG4. Alternatively, the first and second multimerizing domains may be of different IgG isotypes such as, e.g., IgG1/IgG2, IgG1/IgG4, IgG2/IgG4, etc.

In certain embodiments, the multimerizing domain is an Fc fragment or an amino acid sequence of from 1 to about 200 amino acids in length containing at least one cysteine residue. In other embodiments, the multimerizing domain is a cysteine residue, or a short cysteine-containing peptide. Other multimerizing domains include peptides or polypeptides comprising or consisting of a leucine zipper, a helix-loop motif, or a coiled-coil motif.

Any bispecific antibody format or technology may be used to make the bispecific antigen-binding molecules of the present invention. For example, an antibody or fragment thereof having a first antigen binding specificity can be functionally linked (e.g., by chemical coupling, genetic fusion, noncovalent association or otherwise) to one or more other molecular entities, such as another antibody or antibody fragment having a second antigen-binding specificity to produce a bispecific antigen-binding molecule. Specific exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, and Mabe bispecific formats (see, e.g., Klein et al. 2012, mAbs 4:6, 1-11, and references cited therein, for a review of the foregoing formats).

In the context of bispecific antigen-binding molecules of the present invention, the multimerizing domains, e.g., Fc domains, may comprise one or more amino acid changes (e.g., insertions, deletions or substitutions) as compared to the wild-type, naturally occurring version of the Fc domain. For example, the invention includes bispecific antigen-binding molecules comprising one or more modifications in the Fc domain that results in a modified Fc domain having a modified binding interaction (e.g., enhanced or diminished) between Fc and FcRn. In one embodiment, the bispecific antigen-binding molecule comprises a modification in a $C_H2$ or a $C_H3$ region, wherein the modification increases the affinity of the Fc domain to FcRn in an acidic environment (e.g., in an endosome where pH ranges from about 5.5 to about 6.0). Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

The present invention also includes bispecific antigen-binding molecules comprising a first $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). See, for example, U.S. Pat. No. 8,586,713. Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies.

In certain embodiments, the Fc domain may be chimeric, combining Fc sequences derived from more than one immunoglobulin isotype. For example, a chimeric Fc domain can comprise part or all of a $C_H2$ sequence derived from a human IgG1, human IgG2 or human IgG4 $C_H2$ region, and part or all of a $C_H3$ sequence derived from a human IgG1, human IgG2 or human IgG4. A chimeric Fc domain can also contain a chimeric hinge region. For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region. A particular example of a chimeric Fc domain that can be included in any of the antigen-binding molecules set forth herein comprises, from N- to C-terminus: [IgG4 $C_H1$]-[IgG4 upper hinge]-[IgG2 lower hinge]-[IgG4 CH2]-[IgG4 CH3]. Another example of a chimeric Fc domain that can be included in any of the antigen-binding molecules set forth herein comprises, from N- to C-terminus: [IgG1 CH1]-[IgG1 upper hinge]-[IgG2 lower hinge]-[IgG4 CH2]-[IgG1 CH3]. These and other examples of chimeric Fc domains that can be included in any of the antigen-binding molecules of the present invention are described in US Publication 2014/0243504, published Aug. 28, 2014, which is herein incorporated in its entirety. Chimeric Fc domains having these general structural arrangements, and variants thereof, can have altered Fc receptor binding, which in turn affects Fc effector function.

Sequence Variants

The antibodies and bispecific antigen-binding molecules of the present invention may comprise one or more amino acid substitutions, insertions and/or deletions in the framework and/or CDR regions of the heavy and light chain variable domains as compared to the corresponding germline sequences from which the individual antigen-binding domains were derived. Such mutations can be readily ascertained by comparing the amino acid sequences disclosed herein to germline sequences available from, for example, public antibody sequence databases. The antigen-binding molecules of the present invention may comprise antigen-binding domains which are derived from any of the exemplary amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antigen-binding domain was originally derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antigen-binding domain was originally derived). Furthermore, the antigen-binding domains may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antigen-binding domains that contain one or more germline mutations can be easily tested for one or more desired property such as, improved binding specificity, increased binding affinity, improved or enhanced antagonistic or agonistic biological properties (as the case may be), reduced immunogenicity, etc. Bispecific antigen-binding molecules comprising one or more antigen-binding domains obtained in this general manner are encompassed within the present invention.

pH-Dependent Binding

The present invention includes anti-BCMA antibodies, and anti-BCMA×anti-CD3 bispecific antigen-binding molecules, with pH-dependent binding characteristics. For example, an anti-BCMA antibody of the present invention may exhibit reduced binding to BCMA at acidic pH as compared to neutral pH. Alternatively, anti-BCMA antibodies of the invention may exhibit enhanced binding to BCMA at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding . . . at acidic pH as compared to neutral pH" is expressed in terms of a ratio of the $K_D$ value of the antibody binding to its antigen at acidic pH to the $K_D$ value of the antibody binding to its antigen at neutral pH (or vice versa). For example, an antibody or antigen-binding fragment thereof may be regarded as exhibiting "reduced binding to BCMA at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0 or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained.

Antibodies Comprising Fc Variants

According to certain embodiments of the present invention, anti-BCMA antibodies, and anti-BCMA×anti-CD3 bispecific antigen-binding molecules, are provided comprising an Fc domain comprising one or more mutations which enhance or diminish antibody binding to the FcRn receptor, e.g., at acidic pH as compared to neutral pH. For example, the present invention includes antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present invention includes anti-BCMA antibodies, and anti-BCMA×anti-CD3 bispecific antigen-binding molecules, comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

Biological Characteristics of the Antibodies and Bispecific Antigen-Binding Molecules The present invention includes antibodies and antigen-binding fragments thereof that bind human BCMA with high affinity (e.g., nanomolar or sub-nanomolar $K_D$ values).

According to certain embodiments, the present invention includes antibodies and antigen-binding fragments of antibodies that bind human BCMA (e.g., at 25° C.) with a $K_D$ of less than about 5 nM as measured by surface plasmon resonance, e.g., using an assay format as defined in Example 4 herein. In certain embodiments, the antibodies or antigen-binding fragments of the present invention bind BCMA with a $K_D$ of less than about 20 nM, less than about 10 nM, less than about 8 nM, less than about 7 nM, less than about 6 nM, less than about 5 nM, less than about 4 nM, less than about 3 nM, less than about 2 nM, less than about 1 nM, less than about 800 pM, less than about 700 pM, less than about 500 pM, less than about 400 pM, less than about 300 pM, less than about 200 pM, less than about 100 pM, less than about 50 pM, or less than about 25 pM as measured by surface plasmon resonance, e.g., using an assay format as defined in Example 4 herein, or a substantially similar assay. The present invention includes bispecific antigen-binding molecules (e.g., bispecific antibodies which bind human BCMA with a $K_D$ of less than about 25 pM, and which bind monkey BCMA with a $K_D$ of less than about 170 pM, as measured by surface plasmon resonance, e.g., using an assay format as defined in Example 4 herein, or a substantially similar assay.

The present invention also includes antibodies and antigen-binding fragments thereof that bind BCMA with a dissociative half-life (t½) of greater than about 10 minutes or greater than about 125 minutes as measured by surface plasmon resonance at 25° C., e.g., using an assay format as defined in Example 4 herein, or a substantially similar assay. In certain embodiments, the antibodies or antigen-binding fragments of the present invention bind BCMA with a t½ of greater than about 3 minutes, greater than about 4 minutes, greater than about 10 minutes, greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 100 minutes, greater than about 110 minutes, or greater than about 120 minutes, as measured by surface plasmon resonance at 25° C., e.g., using an assay format as defined in Example 4 herein, or a substantially similar assay. The present invention includes bispecific antigen-binding molecules (e.g., bispecific antibodies which bind BCMA with a of greater than about 10 minutes as measured by surface plasmon resonance at 25° C., e.g., using an assay format as defined in Example 4 herein, or a substantially similar assay.

The present invention also includes antibodies and antigen-binding fragments thereof which bind specifically to human cell lines which express endogenous BCMA (e.g., NCI-H929, MOLP-8 or OMP-2), as determined by a FACS binding assay as set forth in Example 6 or a substantially similar assay.

The present invention also includes anti-BCMA×anti-CD3 bispecific antigen-binding molecules which exhibit one or more characteristics selected from the group consisting of: (a) inhibiting tumor growth in immunocompromised mice bearing human multiple myeloma xenografts; (b) suppressing tumor growth of established tumors in immunocompromised mice bearing human multiple myeloma xenografts (see, e.g., Examples 10-15), and (c) suppressing tumor growth of syngenic melanoma and colon carcinoma cells engineered to express human BCMA in immunocompetent mice expressing human CD3.

The present invention includes antibodies and antigen-binding fragments thereof that bind human CD3 with high affinity. The present invention also includes antibodies and antigen-binding fragments thereof that bind human CD3 with medium or low affinity, depending on the therapeutic context and particular targeting properties that are desired.

In some cases, the low affinity includes antibodies that bind CD3 with a $K_D$ or $EC_{50}$ (e.g., as measured in a surface plasmon resonance assay) of greater than about 300 nM, greater than 500 nM or greater than 1 pM. The present invention also includes antibodies and antigen-binding fragments thereof that bind human CD3 with no measureable affinity. For example, in the context of a bispecific antigen-binding molecule, wherein one arm binds CD3 and another arm binds a target antigen (e.g., BCMA), it may be desirable for the target antigen-binding arm to bind the target antigen with high affinity while the anti-CD3 arm binds CD3 with only moderate or low affinity or no affinity. In this manner, preferential targeting of the antigen-binding molecule to cells expressing the target antigen may be achieved while avoiding general/untargeted CD3 binding and the consequent adverse side effects associated therewith.

The present invention includes bispecific antigen-binding molecules (e.g., bispecific antibodies) which are capable of simultaneously binding to human CD3 and a human BCMA. The binding arm that interacts with cells that express CD3 may have weak to no detectable binding as measured in a suitable in vitro binding assay. The extent to which a bispecific antigen-binding molecule binds cells that express CD3 and/or BCMA can be assessed by fluorescence activated cell sorting (FACS), as illustrated in Examples 5 and 6 herein.

For example, the present invention includes antibodies, antigen-binding fragments, and bispecific antibodies thereof which specifically bind human T-cell lines which express CD3 but do not express BCMA (e.g., Jurkat), and/or BCMA-expressing cells.

The present invention includes antibodies, antigen-binding fragments, and bispecific antibodies thereof that bind human CD3 with weak (i.e. low) or even no detectable affinity.

The present invention includes antibodies, antigen-binding fragments, and bispecific antibodies thereof that bind monkey (i.e. cynomolgus) CD3 with weak (i.e. low) or even no detectable affinity.

The present invention includes antibodies, antigen-binding fragments, and bispecific antibodies thereof that bind human CD3 and induce T cell activation.

The present invention includes anti-BCMA×anti-CD3 bispecific antigen-binding molecules which are capable of depleting or reducing tumor antigen-expressing cells in a subject (see, e.g., Examples 8-16, or a substantially similar assay). For example, according to certain embodiments, anti-BCMA×anti-CD3 bispecific antigen-binding molecules are provided, wherein a single administration, or multiple administrations, of 0.04 mg/kg, 0.4 mg/kg or 4 mg/kg of the bispecific antigen-binding molecule to a subject causes a reduction in the number of BCMA-expressing cells in the subject (e.g., tumor growth in the subject is suppressed or inhibited).

Epitope Mapping and Related Technologies

The epitope on CD3 and/or BCMA to which the antigen-binding molecules of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of a CD3 or BCMA protein. Alternatively, the epitope may consist of a plurality of non-contiguous amino acids (or amino acid sequences) of CD3 or BCMA. The antibodies of the invention may interact with amino acids contained within a single CD3 chain (e.g., CD3-epsilon, CD3-delta or CD3-gamma), or may interact with amino acids on two or more different CD3 chains. The term "epitope," as used herein, refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstances, an epitope may include moieties of saccharides, phosphoryl groups, or sulfonyl groups on the antigen.

Various techniques known to persons of ordinary skill in the art can be used to determine whether an antigen-binding domain of an antibody "interacts with one or more amino acids" within a polypeptide or protein. Exemplary techniques include, e.g., routine cross-blocking assay such as that described Antibodies, Harlow and Lane (Cold Spring Harbor Press, Cold Spring Harb., NY), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antigen-binding domain of an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A. X-ray crystallography of the antigen/antibody complex may also be used for epitope mapping purposes.

The present invention further includes anti-BCMA antibodies that bind to the same epitope as any of the specific exemplary antibodies described herein (e.g. antibodies comprising any of the amino acid sequences as set forth in Table 1 herein). Likewise, the present invention also includes anti-BCMA antibodies that compete for binding to BCMA with any of the specific exemplary antibodies described herein (e.g. antibodies comprising any of the amino acid sequences as set forth in Table 1 herein).

The present invention also includes bispecific antigen-binding molecules comprising a second antigen-binding domain that specifically binds human CD3 and/or cynomolgus CD3 with low or no detectable binding affinity, and a second antigen binding domain that specifically binds human BCMA, wherein the second antigen-binding domain binds to the same epitope on CD3 as any of the specific exemplary CD3-specific antigen-binding domains described herein, and/or wherein the second antigen-binding domain binds to the same epitope on BCMA as any of the specific exemplary BCMA-specific antigen-binding domains described herein.

Likewise, the present invention also includes bispecific antigen-binding molecules comprising a first antigen-binding domain that specifically binds human BCMA, and a second antigen binding domain that specifically binds human CD3, wherein the first antigen-binding domain competes for binding to BCMA with any of the specific exemplary BCMA-specific antigen-binding domains described herein, and/or wherein the second antigen-binding domain competes for binding to CD3 with any of the specific exemplary CD3-specific antigen-binding domains described herein.

One can easily determine whether a particular antigen-binding molecule (e.g., antibody) or antigen-binding domain thereof binds to the same epitope as, or competes for binding with, a reference antigen-binding molecule of the present invention by using routine methods known in the art. For example, to determine if a test antibody binds to the same epitope on BCMA (or CD3) as a reference bispecific antigen-binding molecule of the present invention, the reference bispecific molecule is first allowed to bind to a BCMA protein (or CD3 protein). Next, the ability of a test antibody to bind to the BCMA (or CD3) molecule is assessed. If the test antibody is able to bind to BCMA (or CD3) following saturation binding with the reference bispecific antigen-binding molecule, it can be concluded that the test antibody binds to a different epitope of BCMA (or CD3) than the reference bispecific antigen-binding molecule. On the other hand, if the test antibody is not able to bind to the BCMA (or CD3) molecule following saturation binding with the reference bispecific antigen-binding molecule, then the test antibody may bind to the same epitope of BCMA (or CD3) as the epitope bound by the reference bispecific antigen-binding molecule of the invention. Additional routine experimentation (e.g., peptide mutation and binding analyses) can then be carried out to confirm whether the observed lack of binding of the test antibody is in fact due to binding to the same epitope as the reference bispecific antigen-binding molecule or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antigen-binding proteins bind to the same (or overlapping) epitope if, e.g., a 1-, 5-, 10-, 20- or 100-fold excess of one antigen-binding protein inhibits binding of the other by at least 50% but preferably 75%, 90% or even 99% as measured in a competitive binding assay (see, e.g., Junghans et al., Cancer Res. 1990:50:1495-1502). Alternatively, two antigen-binding proteins are deemed to bind to the same epitope if essentially all amino acid mutations in the antigen that reduce or eliminate binding of one antigen-binding protein reduce or eliminate binding of the other. Two antigen-binding proteins are deemed to have "overlapping epitopes" if only a subset of the amino acid mutations that reduce or eliminate binding of one antigen-binding protein reduce or eliminate binding of the other.

To determine if an antibody or antigen-binding domain thereof competes for binding with a reference antigen-binding molecule, the above-described binding methodology is performed in two orientations: In a first orientation, the reference antigen-binding molecule is allowed to bind to a BCMA protein (or CD3 protein) under saturating conditions followed by assessment of binding of the test antibody to the BCMA (or CD3) molecule. In a second orientation, the test antibody is allowed to bind to a BCMA (or CD3) molecule under saturating conditions followed by assessment of binding of the reference antigen-binding molecule to the BCMA (or CD3) molecule. If, in both orientations, only the first (saturating) antigen-binding molecule is capable of binding to the BCMA (or CD3) molecule, then it is concluded that the test antibody and the reference antigen-binding molecule compete for binding to BCMA (or CD3). As will be appreciated by a person of ordinary skill in the art, an antibody that competes for binding with a reference antigen-binding molecule may not necessarily bind to the same epitope as the reference antibody, but may sterically block binding of the reference antibody by binding an overlapping or adjacent epitope.

Preparation of Antigen-Binding Domains and Construction of Bispecific Molecules

Antigen-binding domains specific for particular antigens can be prepared by any antibody generating technology known in the art. Once obtained, two different antigen-binding domains, specific for two different antigens (e.g., CD3 and BCMA), can be appropriately arranged relative to one another to produce a bispecific antigen-binding molecule of the present invention using routine methods. (A discussion of exemplary bispecific antibody formats that can be used to construct the bispecific antigen-binding molecules of the present invention is provided elsewhere herein). In certain embodiments, one or more of the individual components (e.g., heavy and light chains) of the multispecific antigen-binding molecules of the invention are derived from chimeric, humanized or fully human antibodies. Methods for making such antibodies are well known in the art. For example, one or more of the heavy and/or light chains of the bispecific antigen-binding molecules of the present invention can be prepared using VELOCIMMUNE™ technology. Using VELOCIMMUNE™ technology (or any other human antibody generating technology), high affinity chimeric antibodies to a particular antigen (e.g., CD3 or BCMA) are initially isolated having a human variable region and a mouse constant region. The antibodies are characterized and selected for desirable characteristics, including affinity, selectivity, epitope, etc. The mouse constant regions are replaced with a desired human constant region to generate fully human heavy and/or light chains that can be incorporated into the bispecific antigen-binding molecules of the present invention.

Genetically engineered animals may be used to make human bispecific antigen-binding molecules. For example, a genetically modified mouse can be used which is incapable of rearranging and expressing an endogenous mouse immunoglobulin light chain variable sequence, wherein the mouse expresses only one or two human light chain variable domains encoded by human immunoglobulin sequences operably linked to the mouse kappa constant gene at the endogenous mouse kappa locus. Such genetically modified mice can be used to produce fully human bispecific antigen-binding molecules comprising two different heavy chains that associate with an identical light chain that comprises a variable domain derived from one of two different human light chain variable region gene segments. (See, e.g., US 2011/0195454). Fully human refers to an antibody, or antigen-binding fragment or immunoglobulin domain thereof, comprising an amino acid sequence encoded by a DNA derived from a human sequence over the entire length of each polypeptide of the antibody or antigen-binding fragment or immunoglobulin domain thereof. In some instances, the fully human sequence is derived from a protein endogenous to a human. In other instances, the fully human protein or protein sequence comprises a chimeric sequence wherein each component sequence is derived from human sequence. While not being bound by any one theory, chimeric proteins or chimeric sequences are generally designed to minimize the creation of immunogenic epitopes in the junctions of component sequences, e.g. compared to any wild-type human immunoglobulin regions or domains.

Bioequivalents

The present invention encompasses antigen-binding molecules having amino acid sequences that vary from those of the exemplary molecules disclosed herein but that retain the ability to bind CD3 and/or BCMA. Such variant molecules may comprise one or more additions, deletions, or substitutions of amino acids when compared to parent sequence, but exhibit biological activity that is essentially equivalent to that of the described bispecific antigen-binding molecules.

The present invention includes antigen-binding molecules that are bioequivalent to any of the exemplary antigen-binding molecules set forth herein. Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antigen-binding proteins will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antigen-binding protein.

Bioequivalent variants of the exemplary bispecific antigen-binding molecules set forth herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antigen-binding proteins may include variants of the exemplary bispecific antigen-binding molecules set forth herein comprising amino acid changes which modify the glycosylation characteristics of the molecules, e.g., mutations which eliminate or remove glycosylation.

Species Selectivity and Species Cross-Reactivity

According to certain embodiments of the invention, antigen-binding molecules are provided which bind to human CD3 but not to CD3 from other species. Also provided are antigen-binding molecules which bind to human BCMA, but not to BCMA from other species. The present invention also includes antigen-binding molecules that bind to human CD3 and to CD3 from one or more non-human species; and/or antigen-binding molecules that bind to human BCMA and to BCMA from one or more non-human species.

According to certain exemplary embodiments of the invention, antigen-binding molecules are provided which bind to human CD3 and/or human BCMA and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee CD3 and/or BCMA. For example, in particular exemplary embodiments of the present invention bispecific antigen-binding molecules are provided comprising a first antigen-binding domain that binds human BCMA and cynomolgus BCMA, and a second antigen-binding domain that specifically binds human CD3, or bispecific antigen-binding molecules comprising a first antigen-binding domain that binds human BCMA and cynomolgus BCMA, and a second antigen-binding domain that specifically binds human CD3.

Therapeutic Formulation and Administration

The present invention provides pharmaceutical compositions comprising the antigen-binding molecules of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, PA These formulations include, for example, powders, pastes, ointments, jellies, waxes, oils, lipids, lipid (cationic or anionic) containing vesicles (such as LIPOFECTIN™, Life Technologies, Carlsbad, CA), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antigen-binding molecule administered to a patient may vary depending upon the age and the size of the patient, target disease, conditions, route of administration, and the like. The preferred dose is typically calculated according to body weight or body surface area. When a bispecific antigen-binding molecule of the present invention is used for therapeutic purposes in an adult patient, it may be advantageous to intravenously administer the bispecific antigen-binding molecule of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering a bispecific antigen-binding molecule may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L.P.), and the HUMIRA™ Pen (Abbott Labs, Abbott Park IL), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Florida. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antigen-Binding Molecules

The present invention includes methods comprising administering to a subject in need thereof a therapeutic composition comprising an anti-BCMA antibody or antigen-binding fragment thereof, or a bispecific antigen-binding molecule that specifically binds CD3 and BCMA. The therapeutic composition can comprise any of the antibodies or bispecific antigen-binding molecules as disclosed herein and a pharmaceutically acceptable carrier or diluent. As used herein, the expression "a subject in need thereof" means a human or non-human animal that exhibits one or more symptoms or indicia of cancer (e.g., a subject expressing a tumor or suffering from any of the cancers mentioned herein below), or who otherwise would benefit from an inhibition or reduction in BCMA activity or a depletion of BCMA+ cells (e.g., multiple myeloma cells).

The antibodies and bispecific antigen-binding molecules of the invention (and therapeutic compositions comprising the same) are useful, inter alia, for treating any disease or disorder in which stimulation, activation and/or targeting of an immune response would be beneficial. In particular, the anti-BCMA antibodies or the anti-BCMAxanti-CD3 bispecific antigen-binding molecules of the present invention may be used for the treatment, prevention and/or amelioration of any disease or disorder associated with or mediated by BCMA expression or activity or the proliferation of BCMA+ cells. The mechanism of action by which the therapeutic methods of the invention are achieved include killing of the cells expressing BCMA in the presence of effector cells, for example, by CDC, apoptosis, ADCC, phagocytosis, or by a combination of two or more of these mechanisms. Cells expressing BCMA which can be inhibited or killed using the bispecific antigen-binding molecules of the invention include, for example, multiple myeloma cells.

The antigen-binding molecules of the present invention may be used to treat a disease or disorder associates with BCMA expression including, e.g., a cancer including multiple myeloma or other B-cell or plasma cell cancers, such as Waldenström's macroglobulinemia, Burkitt lymphoma, and diffuse large B-Cell lymphoma, Non-Hodgkin's lymphoma, chronic lymphocytic leukemia, follicular lymphoma, mantle cell lymphoma, marginal zone lymphoma, lymphoplasmacytic lymphoma, and Hodgkin's lymphoma. According to certain embodiments of the present invention, the anti-BCMA antibodies or anti-BCMAxanti-CD3 bispecific antibodies are useful for treating a patient afflicted with multiple myeloma. According to other related embodiments of the invention, methods are provided comprising administering an anti-BCMA antibody or an anti-BCMAxanti-CD3 bispecific antigen-binding molecule as disclosed herein to a patient who is afflicted with multiple myeloma. Analytic/diagnostic methods known in the art, such as tumor scanning, etc., may be used to ascertain whether a patient harbors multiple myeloma or another B-cell lineage cancer.

The present invention also includes methods for treating residual cancer in a subject. As used herein, the term "residual cancer" means the existence or persistence of one or more cancerous cells in a subject following treatment with an anti-cancer therapy.

According to certain aspects, the present invention provides methods for treating a disease or disorder associated with BCMA expression (e.g., multiple myeloma) comprising administering one or more of the anti-BCMA or bispecific antigen-binding molecules described elsewhere herein to a subject after the subject has been determined to have multiple myeloma. For example, the present invention includes methods for treating multiple myeloma comprising administering an anti-BCMA antibody or an anti-BCMAx anti-CD3 bispecific antigen-binding molecule to a patient 1 day, 2 days, 3 days, 4 days, 5 days, 6 days, 1 week, 2 weeks, 3 weeks or 4 weeks, 2 months, 4 months, 6 months, 8 months, 1 year, or more after the subject has received other immunotherapy or chemotherapy.

Combination Therapies and Formulations

The present invention provides methods which comprise administering a pharmaceutical composition comprising any of the exemplary antibodies and bispecific antigen-binding molecules described herein in combination with one or more additional therapeutic agents. Exemplary additional therapeutic agents that may be combined with or administered in combination with an antigen-binding molecule of the present invention include, e.g., an anti-tumor agent (e.g. chemotherapeutic agents including melphalan, vincristine (Oncovin), cyclophosphamide (Cytoxan), etoposide (VP-16), doxorubicin (Adriamycin), liposomal doxorubicin (Doxil), obendamustine (Treanda), or any others known to be effective in treating a plasma cell tumor in a subject.). In some embodiments, the second therapeutic agent comprises steroids. In some embodiments, the second therapeutic agent comprises targeted therapies including thalidomide, lenalidomide, and bortezomib, which are therapies approved to treat newly diagnosed patients. Lenalidomide, pomalidomide, bortezomib, carfilzomib, panobinostat, ixazomib, elotuzumab, and daratumumab are examples of a second therapeutic agent effective for treating recurrent myeloma. In certain embodiments the second therapeutic agent is a regimen comprising radiotherapy or a stem cell transplant.

In certain embodiments, the second therapeutic agent may be an immunomodulatory agent. In certain embodiments; the second therapeutic agent may be a proteasome inhibitor; including bortezomib (Velcade), carfilzomib (Kyprolis), ixazomib (Ninlaro). In certain embodiments the second therapeutic agent may be a histone deacetylase inhibitor such as panobinostat (Farydak). In certain embodiments, the second therapeutic agent may be a monoclonal antibody, an antibody drug conjugate, a bispecific antibody conjugated to an anti-tumor agent, a checkpoint inhibitor, or combinations thereof. Other agents that may be beneficially administered in combination with the antigen-binding molecules of the invention include cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors. The pharmaceutical compositions of the present invention (e.g., pharmaceutical compositions comprising an anti-BCMA×anti-CD3 bispecific antigen-binding molecule as disclosed herein) may also be administered as part of a therapeutic regimen comprising one or more therapeutic combinations selected from a monoclonal antibody other than those described herein, which may interact with a different antigen on the plasma cell surface, a bispecific antibody, which has one arm that binds to an antigen on the tumor cell surface and the other arm binds to an antigen on a T cell, an antibody drug conjugate, a bispecific antibody conjugated with an anti-tumor agent, a checkpoint inhibitor, for example, one that targets, PD-1 or CTLA-4, or combinations thereof. In certain embodiments, the checkpoint inhibitors may be selected from PD-1 inhibitors, such as pembrolizumab (Keytruda), nivolumab (Opdivo), or cemiplimab (REGN2810). In certain embodiments, the checkpoint inhibitors may be selected from PD-L1 inhibitors, such as atezolizumab (Tecentriq), avelumab (Bavencio), or Durvalumab (Imfinzi)). In certain embodiments, the checkpoint inhibitors may be selected from CTLA-4 inhibitors, such as ipilimumab (Yervoy). Other combinations that may be used in conjunction with an antibody of the invention are described above.

The present invention also includes therapeutic combinations comprising any of the antigen-binding molecules mentioned herein and an inhibitor of one or more of VEGF, Ang2, DLL4, EGFR, ErbB2, ErbB3, ErbB4, EGFRvIII, cMet, IGF1R, B-raf, PDGFR-α, PDGFR-β, FOLH1 (PSMA), PRLR, STEAP1, STEAP2, TMPRSS2, MSLN, CA9, uroplakin, or any of the aforementioned cytokines, wherein the inhibitor is an aptamer, an antisense molecule, a ribozyme, an siRNA, a peptibody, a nanobody or an antibody fragment (e.g., Fab fragment; F(ab')$_2$ fragment; Fd fragment; Fv fragment; scFv; dAb fragment; or other engineered molecules, such as diabodies, triabodies, tetrabodies, minibodies and minimal recognition units). The antigen-binding molecules of the invention may also be administered and/or co-formulated in combination with antivirals, antibiotics, analgesics, corticosteroids and/or NSAIDs. The antigen-binding molecules of the invention may also be administered as part of a treatment regimen that also includes radiation treatment and/or conventional chemotherapy.

The additional therapeutically active component(s) may be administered just prior to, concurrent with, or shortly after the administration of an antigen-binding molecule of the present invention; (for purposes of the present disclosure, such administration regimens are considered the administration of an antigen-binding molecule "in combination with" an additional therapeutically active component).

The present invention includes pharmaceutical compositions in which an antigen-binding molecule of the present invention is co-formulated with one or more of the additional therapeutically active component(s) as described elsewhere herein.

Administration Regimens

According to certain embodiments of the present invention, multiple doses of an antigen-binding molecule (e.g., an anti-BCMA antibody or a bispecific antigen-binding molecule that specifically binds BCMA and CD3) may be administered to a subject over a defined time course. The methods according to this aspect of the invention comprise sequentially administering to a subject multiple doses of an antigen-binding molecule of the invention. As used herein, "sequentially administering" means that each dose of an antigen-binding molecule is administered to the subject at a different point in time, e.g., on different days separated by a predetermined interval (e.g., hours, days, weeks or months). The present invention includes methods which comprise sequentially administering to the patient a single initial dose of an antigen-binding molecule, followed by one or more secondary doses of the antigen-binding molecule, and optionally followed by one or more tertiary doses of the antigen-binding molecule.

The terms "initial dose," "secondary doses," and "tertiary doses," refer to the temporal sequence of administration of the antigen-binding molecule of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the antigen-binding molecule, but generally may differ from one another in terms of frequency of administration. In certain embodiments, however, the amount of an antigen-binding molecule contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of antigen-binding molecule which is administered to a patient prior to the administration of the very next dose in the sequence with no intervening doses.

The methods according to this aspect of the invention may comprise administering to a patient any number of secondary and/or tertiary doses of an antigen-binding molecule (e.g., an anti-BCMA antibody or a bispecific antigen-binding molecule that specifically binds BCMA and CD3). For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antibodies

The anti-BCMA antibodies of the present invention may also be used to detect and/or measure BCMA, or BCMA-expressing cells in a sample, e.g., for diagnostic purposes. For example, an anti-BCMA antibody, or fragment thereof, may be used to diagnose a condition or disease characterized by aberrant expression (e.g., over-expression, under-expression, lack of expression, etc.) of BCMA. Exemplary diagnostic assays for BCMA may comprise, e.g., contacting a sample, obtained from a patient, with an anti-BCMA antibody of the invention, wherein the anti-BCMA antibody is labeled with a detectable label or reporter molecule. Alternatively, an unlabeled anti-BCMA antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, beta-galactosidase, horseradish peroxidase, or luciferase. Another exemplary diagnostic use of the anti-BCMA antibodies of the invention includes $^{89}$Zr-labeled, such as $^{89}$Zr-desferrioxamine-labeled, antibody for the purpose of noninvasive identification and tracking of tumor cells in a subject (e.g. positron emission tomography (PET) imaging). (See, e.g., Tavare, R. et al. Cancer Res. 2016 Jan. 1; 76(1):73-82; and Azad, B B. et al. Oncotarget. 2016 Mar. 15; 7(11):12344-58.) Specific exemplary assays that can be used to detect or measure BCMA in a sample include enzyme-linked immunosorbent assay (ELISA), radioimmunoassay (RIA), and fluorescence-activated cell sorting (FACS).

Samples that can be used in BCMA diagnostic assays according to the present invention include any tissue or fluid sample obtainable from a patient which contains detectable quantities of BCMA protein, or fragments thereof, under normal or pathological conditions. Generally, levels of BCMA in a particular sample obtained from a healthy patient (e.g., a patient not afflicted with a disease or condition associated with abnormal BCMA levels or activity) will be measured to initially establish a baseline, or standard, level of BCMA. This baseline level of BCMA can then be compared against the levels of BCMA measured in samples obtained from individuals suspected of having a BCMA related disease (e.g., a tumor containing BCMA-expressing cells) or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Generation of Anti-BCMA Antibodies

Anti-BCMA antibodies were obtained by immunizing a genetically modified mouse with a human BCMA antigen (e.g., hBCMA, SEQ ID NO: 115) or by immunizing an engineered mouse comprising DNA encoding human immunoglobulin heavy and kappa light chain variable regions with a human BCMA antigen.

Following immunization, splenocytes were harvested from each mouse and either (1) fused with mouse myeloma cells to preserve their viability and form hybridoma cells and screened for BCMA specificity, or (2) B-cell sorted (as described in US 2007/0280945A1) using a human BCMA fragment as the sorting reagent that binds and identifies reactive antibodies (antigen-positive B cells).

Chimeric antibodies to BCMA were initially isolated having a human variable region and a mouse constant region. The antibodies were characterized and selected for desirable characteristics, including affinity, selectivity, etc. If necessary, mouse constant regions were replaced with a desired human constant region, for example wild-type or modified IgG1 or IgG4 constant region, to generate a fully human anti-BCMA antibody. While the constant region selected may vary according to specific use, high affinity antigen-binding and target specificity characteristics reside in the variable region.

Heavy and Light Chain Variable Region Amino Acid and Nucleic Acid Sequences of anti-BCMA antibodies: Table 1 sets forth the amino acid sequence identifiers of the heavy and light chain variable regions and CDRs of selected anti-BCMA antibodies of the invention. The corresponding nucleic acid sequence identifiers are set forth in Table 2.

TABLE 1

| Antibody | Amino Acid Sequence Identifiers | | | | | | | |
|---|---|---|---|---|---|---|---|---|
| | SEQ ID NOs: | | | | | | | |
| Designation | HCVR | HCDR1 | HCDR2 | HCDR3 | LCVR | LCDR1 | LCDR2 | LCDR3 |
| mAb16711 | 2 | 4 | 6 | 8 | 10 | 12 | 14 | 16 |
| mAb16716 | 18 | 20 | 22 | 24 | 26 | 28 | 30 | 32 |
| mAb16732 | 34 | 36 | 38 | 40 | 42 | 44 | 46 | 48 |

TABLE 1-continued

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| mAb16747 | 50 | 52 | 54 | 56 | 58 | 60 | 62 | 64 |
| mAb21581 | 66 | 68 | 70 | 72 | 74 | 76 | 78 | 80 |
| mAb21587 | 122 | | | | 123 | | | |
| mAb21589 | 124 | | | | 125 | | | |

TABLE 2

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| mAb16711 | 1 | 3 | 5 | 7 | 9 | 11 | 13 | 15 |
| mAb16716 | 17 | 19 | 21 | 23 | 25 | 27 | 29 | 31 |
| mAb16732 | 33 | 35 | 37 | 39 | 41 | 43 | 45 | 47 |
| mAb16747 | 49 | 51 | 53 | 55 | 57 | 59 | 61 | 63 |
| mAb21581 | 65 | 67 | 69 | 71 | 73 | 75 | 77 | 79 |

Example 2: Generation of Anti-CD3 Antibodies

Anti-CD3 antibodies were generated as described in WO 2017/053856, which is herein incorporated by reference. Two such anti-CD3 antibodies were selected from the production of bispecific anti-BCMA×anti-CD3 antibodies in accordance with the present invention. Table 3 sets forth the amino acid sequence identifiers of the heavy and light chain variable regions and CDRs of selected anti-CD3 antibodies. The corresponding nucleic acid sequence identifiers are set forth in Table 4. Other anti-CD3 antibodies for use in preparing bispecific antibodies in accordance with the present invention can be found in, e.g., WO 2014/047231.

Example 3: Generation of Bispecific Antibodies that Bind BCMA and CD3

The present invention provides bispecific antigen-binding molecules that bind CD3 and BCMA; such bispecific antigen-binding molecules are also referred to herein as "anti-BCMA×anti-CD3 or anti-CD3×BCMA or anti-BCMA×anti-CD3 bispecific molecules." The anti-BCMA portion of the anti-BCMA×anti-CD3 bispecific molecule is useful for targeting tumor cells that express BCMA (also known as CD269), and the anti-CD3 portion of the bispecific molecule is useful for activating T-cells. The simultaneous binding of BCMA on a tumor cell and CD3 on a T-cell facilitates directed killing (cell lysis) of the targeted tumor cell by the activated T-cell.

TABLE 3

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| mAb7221G | 90 | 92 | 94 | 96 | 82 | 84 | 86 | 88 |
| mAb7221G20 | 98 | 100 | 102 | 104 | 82 | 84 | 86 | 88 |

TABLE 4

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| mAb7221G | 89 | 91 | 93 | 95 | 81 | 83 | 85 | 87 |
| mAb7221G20 | 97 | 99 | 101 | 103 | 81 | 83 | 85 | 87 |

Bispecific antibodies comprising an anti-BCMA-specific binding domain and an anti-CD3-specific binding domain were constructed using standard methodologies, wherein the anti-BCMA antigen binding domain and the anti-CD3 antigen binding domain each comprise different, distinct HCVRs paired with a common LCVR. In exemplified bispecific antibodies, the molecules were constructed utilizing a heavy chain from an anti-CD3 antibody, a heavy chain from an anti-BCMA antibody and a common light chain from the anti-CD3 antibody (10082). In other instances, the bispecific antibodies may be constructed utilizing a heavy chain from an anti-CD3 antibody, a heavy chain from an anti-BCMA antibody and an antibody light chain known to be promiscuous or pair effectively with a variety of heavy chain arms.

TABLE 5

Summary of Component Parts of Anti-BCMA × Anti-CD3 Bispecific Antibodies

| Bispecific Antibody Identifier | Anti-BCMA Antigen-Binding Domain Heavy Chain Variable Region | Anti-CD3 Antigen-Binding Domain Heavy Chain Variable Region | Common Light Chain Variable Region |
|---|---|---|---|
| bsAb25441D9 (also referred to as REGN5458) | mAb21581 | mAb7221G | mAb7221G |
| bsAb25442D (also referred to as REGN5459) | mAb21581 | mAb7221G20 | mAb7221G20 |

Table 6 shows the amino acid sequence identifiers for the bispecific anti-BCMA×anti-CD3 antibodies exemplified herein.

HEPES pH 7.4, 0.15M NaCl, 3 mM EDTA, 0.05% v/v Surfactant P20 (HBS-ET running buffer). For monomeric affinities, different concentrations of the extracellular domain of human BCMA expressed with C-terminal myc-myc-hexahistidine tag (human BCMA-MMH; SEQ ID NO: 106) or monkey BCMA expressed with C-terminal myc-myc-hexahistidine tag (monkey BCMA-MMH; SEQ ID NO: 110) were prepared in HBS-ET running buffer (ranging from 90 to 1.11 nM, 3-fold dilutions). For dimeric affinities, different concentrations of the extracellular domain of human BCMA expressed with C-terminal mFc tag (human BCMA-MFC; SEQ ID NO: 108) monkey BCMA expressed with C-terminal mFc tag (monkey BCMA-MFC; SEQ ID NO: 112) prepared in HBS-ET running buffer (ranging from 30 to 0.37 nM, 3-fold dilutions) or 30 nM BCMA expressed with C-terminal mFc tag (mouse BCMA-MFC; SEQ ID NO: 114) were prepared. Antigen samples were then injected over the anti-BCMA and anti-BCMA×anti-CD3 bispecific mAbs captured surfaces at a flow rate of 30 µL/minute. Antibody-reagent association was monitored for 5 minutes while dissociation in HBS-ET running buffer was monitored for 10 minutes. All of the binding kinetics experiments were performed at 25° C. Kinetic association ($k_a$) and dissociation ($k_d$) rate constants were determined by fitting the real-time sensorgrams to a 1:1 binding model using Scrubber 2.0c curve fitting software. Binding dissociation equilibrium constants ($K_D$) and dissociative half-lives (t½) were calculated from the kinetic rate constants as:

$$K_D(M) = \frac{kd}{ka}, \text{ and}$$

$$t\frac{1}{2}(\min) = \frac{\ln(2)}{60 * kd}$$

As shown in Table 7, at 25° C., all of the anti-BCMA antibodies of the invention bound to human BCMA-MMH with $K_D$ values ranging from 1.06 nM to 3.56 nM. As shown

TABLE 6

Amino Acid Sequences of Anti-BCMA × Anti-CD3 Bispecific Antibodies

| Bispecific Antibody | Anti-BCMA First Antigen-Binding Domain | | | | Anti-CD3 Second Antigen-Binding Domain | | | | Common Light Chain Variable Region | | | |
|---|---|---|---|---|---|---|---|---|---|---|---|---|
| Identifier | HCVR | HCDR1 | HCDR2 | HCDR3 | HCVR | HCDR1 | HCDR2 | HCDR3 | LCVR | LCDR1 | LCDR2 | LCDR3 |
| bsAb25441D (REGN5458) | 66 | 68 | 70 | 72 | 90 | 92 | 94 | 96 | 82 | 84 | 86 | 88 |
| bsAb25442D (REGN5459) | 66 | 68 | 70 | 72 | 98 | 100 | 102 | 104 | 82 | 84 | 86 | 88 |

Example 4: Surface Plasmon Resonance Derived Binding Affinities and Kinetic Constants of Anti-BCMA Antibodies and Anti-BCMA×Anti-CD3 Bispecific Antibodies Equilibrium dissociation constants ($K_D$ values) for hBCMA.mmh (SEQ ID NO: 106) binding to purified anti-BCMA mAbs and anti-BCMA×anti-CD3 bispecific mAbs were determined using a real-time surface plasmon resonance biosensor using a Biacore 4000 instrument. The CM5 Biacore sensor surface was derivatized by amine coupling with a monoclonal mouse anti-human Fc antibody (GE, #BR-1008-39) to capture purified anti-BCMA mAbs and anti-BCMA×anti-CD3 bispecific mAbs. All Biacore binding studies were performed in a buffer composed of 0.01M in Table 8, at 25° C., all of the anti-BCMA antibodies of the invention bound to human BCMA-MFC with $K_D$ values ranging from 22.3 pM to 103 pM. As shown in Table 9, at 25° C., two of the anti-BCMA antibodies of the invention bound to monkey BCMA-MMH with $K_D$ values ranging from 38.8 nM to 49.92 nM. As shown in Table 10, at 25° C., four of the anti-BCMA antibodies of the invention bound to monkey BCMA-MFC with $K_D$ values ranging from 148 pM to 14.7 nM. As shown in Table 11, at 25° C., four of the anti-BCMA antibodies of the invention bound to mouse BCMA-MFC with $K_D$ values ranging from 677 pM to 18.8 nM.

TABLE 7

Binding Kinetics parameters of anti-BCMA monoclonal antibodies binding to human BCMA-MMH at 25° C.

| REGN # | Ab PID # | mAb Capture (RU) | 90 nM hBCMA.mmh Bind (RU) | ka (1/Ms) | kd (1/s) | KD (M) | t½ (min) |
|---|---|---|---|---|---|---|---|
| REGN5458 | bsAb25441D | 437.5 ± 1.1 | 19.9 | 8.27E+05 | 8.74E−04 | 1.06E−09 | 13.2 |
| REGN5459 | bsAb25442D | 384.8 ± 1.4 | 17.0 | 7.30E+05 | 1.01E−03 | 1.38E−09 | 11.5 |
|  | mAb16711 | 275.0 ± 2.8 | 22.2 | 2.01E+06 | 3.47E−03 | 1.73E−09 | 3.3 |
|  | mAb16716 | 310.3 ± 2.2 | 26.4 | 8.41E+05 | 2.99E−03 | 3.56E−09 | 3.9 |
| REGN4514 | mAb16732 | 284.1 ± 0.9 | 25.3 | 1.06E+06 | 2.85E−03 | 2.69E−09 | 4.1 |
| REGN4515 | mAb16747 | 332.5 ± 0.9 | 31.4 | 8.69E+05 | 2.47E−03 | 2.84E−09 | 4.7 |

TABLE 8

Binding Kinetics parameters of anti-BCMA monoclonal antibodies binding to human BCMA-MFC at 25° C.

| REGN # | Ab PID # | mAb Capture (RU) | 30 nM hBCMA.mFc Bind (RU) | ka (1/Ms) | kd (1/s) | KD (M) | t½ (min) |
|---|---|---|---|---|---|---|---|
| REGN5458 | bsAb25441D | 437.9 ± 0.1 | 106.8 | 4.48E+05 | ≤1E−5 | 2.23E−11 | ≤1155 |
| REGN5459 | bsAb25442D | 385.2 ± 0.1 | 96.8 | 4.49E+05 | ≤1E−5 | 2.23E−11 | ≤1155 |
|  | mAb16711 | 268.9 ± 1.4 | 113.5 | 1.85E+06 | 1.90E−04 | 1.03E−10 | 60.8 |
|  | mAb16716 | 303.4 ± 1.2 | 120.3 | 8.62E+05 | 8.35E−05 | 9.68E−11 | 138.4 |
| REGN4514 | mAb16732 | 282.3 ± 1.0 | 124.1 | 1.07E+06 | 4.53E−05 | 4.22E−11 | 255.2 |
| REGN4515 | mAb16747 | 327.3 ± 1.5 | 146.0 | 1.41E+06 | 8.95E−05 | 6.33E−11 | 129.0 |

TABLE 9

Binding Kinetics parameters of anti-BCMA monoclonal antibodies binding to monkey BCMA-MMH at 25° C.

| REGN # | Ab PID # | mAb Capture (RU) | 90 nM mfBCMA.mmh Bind (RU) | ka (1/Ms) | kd (1/s) | KD (M) | t½ (min) |
|---|---|---|---|---|---|---|---|
| REGN5458 | bsAb25441D | 438.2 ± 0.9 | 14.8 | 1.82E+05 | 9.09E−03 | 4.99E−08 | 1.3 |
| REGN5459 | bsAb25442D | 384.6 ± 1.4 | 12.7 | 2.23E+05 | 8.64E−03 | 3.88E−08 | 1.3 |
|  | mAb16711 | 263.5 ± 1.7 | −0.5 | NB | NB | NB | NB |
|  | mAb16716 | 301.8 ± 0.5 | 0.8 | NB | NB | NB | NB |
| REGN4514 | mAb16732 | 279.1 ± 0.8 | 1.1 | NB | NB | NB | NB |
| REGN4515 | mAb16747 | 326.2 ± 0.5 | 1.9 | NB | NB | NB | NB |

TABLE 10

Binding Kinetics parameters of anti-BCMA monoclonal antibodies binding to monkey BCMA-MFC at 25° C.

| REGN # | Ab PID # | mAb Capture (RU) | 30 nM mfBCMA.mFc Bind (RU) | ka (1/Ms) | kd (1/s) | KD (M) | t½ (min) |
|---|---|---|---|---|---|---|---|
| REGN5458 | bsAb25441D | 437.9 ± 1.1 | 107.7 | 5.28E+05 | 8.80E−05 | 1.67E−10 | 131.2 |
| REGN5459 | bsAb25442D | 386.2 ± 0.22 | 97.0 | 4.82E+05 | 7.15E−05 | 1.48E−10 | 161.6 |
|  | mAb16711 | 259.4 ± 1.4 | 0.9 | NB | NB | NB | NB |
|  | mAb16716 | 300.8 ± 0.6 | 3.2 | IC | IC | IC | IC |
| REGN4514 | mAb16732 | 276.9 ± 1.1 | 40.3 | 4.92E+05 | 7.24E−03 | 1.47E−08 | 1.6 |
| REGN4515 | mAb16747 | 324.4 ± 0.7 | 101.3 | 2.13E+06 | 7.16E−03 | 3.37E−09 | 1.6 |

TABLE 11

Binding Kinetics parameters of anti-BCMA monoclonal antibodies binding to mouse BCMA-MFC at 25° C.

| REGN # | Ab PID # | mAb Capture (RU) | 30 nM mfBCMA.mFc Bind (RU) | ka (1/Ms) | kd (1/s) | KD (M) | t½ (min) |
|---|---|---|---|---|---|---|---|
| REGN5458 | bsAb25441D | 438.8 | 2.7 | NB | NB | NB | NB |
| REGN5459 | bsAb25442D | 383.9 | 2.4 | NB | NB | NB | NB |
|  | mAb16711 | 257.0 | 90.0 | 1.07E+06 | 1.10E-03 | 1.02E-09 | 10.5 |
|  | mAb16716 | 300.0 | 33.4 | 2.05E+05 | 3.85E-03 | 1.88E-08 | 3.0 |
| REGN4514 | mAb16732 | 276.1 | 109.6 | 3.97E+05 | 2.69E-04 | 6.77E-10 | 43.0 |
| REGN4515 | mAb16747 | 323.1 | 107.6 | 9.47E+05 | 4.18E-03 | 4.42E-09 | 2.8 |

Example 5: FACS Binding of Anti-BCMA×Anti-CD3 Bispecific Antibodies to Human and Cynomolgous CD3 Expressing Cells Flow cytometric analysis was utilized to determine binding of BCMA×CD3 bispecific antibodies to human and cynomolgus CD3 (Jurkat cells, mfCD3 engineered Jurkat cells, primary human CD8+ and cynomolgus CD8+ T cells). Briefly, 1e05 cells/well were incubated in the presence of FACS wash with block (PBS+1% filtered FBS+5% mouse serum) with a serial dilution of BCMA×CD3 and control antibodies for 30 minutes on ice. After incubation, the cells were washed twice with cold FACS wash (PBS+1% filtered FBS) and bound antibody was detected by incubating with Alexa 647-conjugated anti-human secondary antibody on ice for an additional 30 minutes. Wells containing no antibody or secondary only were used as a control. For the detection of monkey and human T cells, a cocktail of human and cynomolgus cross-reactive antibodies to CD4, CD8 and CD16 was added to the anti-human secondary. After incubation, cells were washed, re-suspended in 200 μL cold PBS containing 1% filtered FBS and analyzed by flow cytometry on a BD FACS Canto II. Cells were gated by FSC-H by FSC-A to select singlet events, followed by side and forward scatters to select for live events. For monkey T cells, additional gating on CD8+/CD16− cells was performed.

EC50 values for FACS binding were calculated using 4-parameter non-linear regression analysis in Prism software.

Jurkat cells are a human CD3 expressing T cell lymphoblastic cell line. REGN5458 bound to human CD3 on Jurkat cells and primary human CD8+ T cells with median EC50s $1.50\times10^{-8}$M and $3.20\times10^{-8}$M respectively. Binding of REGN5459 to human CD3 was weaker, with median EC50 of $5.58\times10^{-7}$M to Jurkat cells and $4.71\times10^{-6}$ to primary human CD8+ T cells. Utilizing CRISPR/Cas9 technology, a Jurkat cell line was engineered to express cynomolgus CD3ε and CD3δ chains in place of the human versions. Median EC50 of binding of REGN5458 to the mfCD3 engineered Jurkat cell line was $1.51\times10^{-8}$M and to primary cynomolgus CD8+ T cells was $4.66\times10^{-8}$M. REGN5459 did not bind to mfCD3 expressing cells.

No binding was observed on any cell line for the negative isotype control antibody, designated mAb15260.

TABLE 12

Binding to CD3 expressing cells: Median EC50

| REGN | Jurkat-hCD3 EC50 [M] | n | Jurkat-mfCD3 EC50 [M] | n | Human CD8+ T cells EC50 [M] | n | Mf (Cyno) CD8+ T cells EC50 [M] | n |
|---|---|---|---|---|---|---|---|---|
| REGN5458 | 1.50E-08 | 5 | 1.51E-08 | 2 | 3.20E-08 | 1 | 4.66E-08 | 1 |
| REGN5459 | 5.58E-07 | 5 | No Binding | 2 | 4.71E-06 | 1 | No binding | 1 |

Example 6: FACS Binding Assay to Assess Cell Surface Antigen Binding Capacity The ability of the anti-BCMA×CD3 antibody, mAb25442D, to bind the surface of BCMA positive multiple myeloma (NCI-H929, MM.1S, OPM-2, and RPMI-8226), BCMA positive lymphoma (Raji and Daudi), and BCMA negative (HEK293) cells was determined via flow cytometry. Cells were harvested from the flasks using cell dissociation buffer (Millipore, Cat #S-004-C) and plated in staining buffer (PBS, without Calcium and Magnesium (Irving 9240)+2% FBS (ATCC 30-2020) at a density of 500,000 cells per well in a 96 well V-Bottom plate. Cells were stained for 30 mins at 4° C. with two-fold serial dilutions of an Alexa647 conjugated anti-BCMA×CD3 antibody (mAb25442D-A647) or an Alexa 647 conjugated isotype control with the same CD3 binding arm paired with an irrelevant tumor targeting arm (Isotype-A647). Cells were washed twice with staining buffer and labeled with the LIVE/DEAD™ Fixable Green Dead Cell Stain Kit (Invitrogen, L34970) according to manufacture instructions to discriminate between live and dead cells. Cells were then washed and fixed for 25 mins at 4° C. using a 50% solution of BD Cytofix (BD, Cat #554655) diluted in PBS. Samples were run on the Accuri C6 flow cytometer (BD Biosciences) and analyzed in Flowjo 10.2 (Tree Star). After gating for live cells and single cells, the mean fluorescent intensity (MFI) was determined, and MFI values were plotted in Graphpad Prism using a four-parameter logistic equation over a 10-point response curve to calculate $EC_{50}$s. The zero condition for each dose-response curve is also included in the analysis as a continuation of the two-fold serial dilution and is represented as the lowest dose. The signal to noise (S/N)

is determined by taking the ratio of the mAb25442D-A647 MFI to the Isotype-A647 MFI. (Table 13). The mAb25442D-A647 S/N ranged from 2 to 470 and the $EC_{50}$ values ranged from 27 to 83 nM. No detectable binding was observed on HEK293 cells.

TABLE 13

Binding to Cells

| Cell Line | mAb25442D-A647 S/N | mAb25442D-A647 $EC_{50}$ (nM) |
|---|---|---|
| NCI-H929 | 470 | 79 |
| MM.1S | 43 | 83 |
| OPM-2 | 19 | 57 |
| RPMI-8226 | 9 | 27 |
| Daudi | 3 | ND |
| Raji | 2 | ND |
| HEK293 | 1 | ND |

ND = not determined due to non-sigmoidal curves

Example 7: T-Cell Activation Via Bispecific Anti-BCMA×Anti-CD3 Antibodies in the Presence of BCMA-Expressing Cells Activity of the anti-BCMA×anti-CD3 bispecific antibodies were assessed in a Jurkat/NFATLuc reporter bioassay utilizing several cell lines with varying levels of BCMA surface expression. The Jurkat cells were engineered to express an NFAT-luciferase reporter (Jurkat/NFATLuc.3C7), and 50,000 Jurkat reporter cells were combined with 50,000 BCMA positive (Daudi, MM1-S, NCI-H929, OPM-2, RPMI-8226, MOLP-8, or Raji) or BCMA negative (HEK293) cells in Thermo Nunclon delta 96 well white microwell plates (Thermo Scientific, Cat #136102) in 50 ul of assay media (RPMI media with 10% FBS and 1% P/S/G). Three-fold serial dilutions of the BCMA×CD3 bispecific antibodies (mAb25441D or mAb25442D), or a bivalent anti-BCMA antibody (mAb21581) were immediately added in 50 uL of assay buffer. The plates were gently agitated and incubated in a 37° C., 5% $CO_2$ incubator for 4-6 hours. NFAT-Luciferase activity was determined using Promega One-Glo (Cat #E6130) and a Perkin Elmer Envision plate reader. RLU were plotted in GraphPad Prism using a four-parameter logistic equation over a 12-point response curve to calculate $EC_{50}$ values. The no antibody treatment condition for each dose-response curve is also included in the analysis as a continuation of the three-fold serial dilution and is represented as the lowest dose. The signal to noise (S:N) is determined by taking the ratio of the highest RLU on the curve to the lowest.

mAb25441D activated Jurkat/NFATLuc cells in the presence of BCMA expressing cells with EC50s ranging from 0.61 nM to 2.1 nM and S:N ranging from 8 to 123. mAb25442D activated Jurkat/NFATLuc cells in the presence of BCMA expressing cells with EC50s ranging from 2.6 nM to 11 nM and S:N ranging from 7 to 120. The BCMA×CD3 bispec mAb25441D with the higher affinity CD3 binding arm was consistently more potent than mAb25442D with a lower affinity CD3 binding arm; whereas, the S:N was similar for the two bispecifics. Neither antibody activated Jurkat/NFATLuc cells in the presence of HEK293 cells, and control bispecific antibodies did not significantly increase Jurkat reporter activity with any of the tested cell lines. The results are shown in Tables 14A and 14B, below.

TABLE 14A

Activation of T-Cells

| | Daudi | | MM1-S | | NCI-H929 | | OPM-2 | |
|---|---|---|---|---|---|---|---|---|
| Antibodies | EC50 | S:N | EC50 | S:N | EC50 | S:N | EC50 | S:N |
| bsAb25441D | 2.1E−9 | 43 | 1.2E−9 | 165 | 6.8E−10 | 39 | 6.6E−10 | 8 |
| bsAb25442D | 7.9E−9 | 25 | 4.4E−9 | 120 | 2.7E−9 | 32 | 2.6E−9 | 7 |
| mAb21581 | ND | 1 | ND | 1 | ND | 1 | ND | 1 |

TABLE 14B

Activation of T-Cells

| | RPMI-8226 | | MOLP-8 | | Raji | | HEK293 | |
|---|---|---|---|---|---|---|---|---|
| Antibodies | EC50 | S:N | EC50 | S:N | EC50 | S:N | EC50 | S:N |
| bsAb25441D | 6.1E−10 | 55 | 1.4E−9 | 32 | 1.6E−9 | 123 | ND | 1 |
| bsAb25442D | 2.6E−9 | 42 | 1.1E−8 | 31 | 7.4E−9 | 78 | ND | 1 |
| mAb21581 | ND | 1 | ND | 1 | ND | 1 | ND | 1 |

Example 8: FACS Based Cytotoxicity Assay to Assess T Cell-Mediated Killing of BCMA-Expressing Multiple Myeloma Cells in the Presence of Anti-BCMA×Anti-CD3 Bispecific Antibodies Antibody binding capacity (ABC) of a commercially available anti-human BCMA antibody (clone 19F2) was determined on a panel of multiple myeloma cell lines using a Quantum Simply Cellular anti-human IgG kit and following the manufacturer's instructions (Bangs Laboratories).

Briefly, multiple myeloma (MM) cell lines (H929, MM1S, U266, MOLP8 and RPMI8226) and Quantum Simply Cellular beads were incubated for 30 minutes at 4° C. with a titration of APC conjugated anti-hBCMA-19F2 antibody. After incubation, cells and beads were washed three times, re-suspended in 200 μL cold PBS containing 1% filtered FBS and analyzed by flow cytometry. Using the QuickCal® template (Bangs Labs), the ABC of a saturating level of anti-BCMA 19F2 for each cell line was interpolated from the standard curve generated by the channel intensity of the bead populations at saturation.

Killing of BCMA expressing target cells by resting human or cynomolgus monkey T cells was determined by flow cytometry. Briefly, human or cynomolgus monkey peripheral blood mononuclear cells (PBMC) were plated in supplemented RPMI (human) or X-Vivo™ (cyno) media at $1 \times 10^6$ cells/mL and incubated overnight at 37° C. in order to enrich for lymphocytes by depleting adherent macrophages, dendritic cells, and some monocytes. The next day, BCMA expressing target cells were labeled with 1 μM of Violet CellTrace™ and co-incubated with adherent cell-depleted PBMC (effector/target cell 4:1 ratio) and a serial dilution of BCMA×CD3 bispecifics, or control antibodies at 37° C. After 48-72 hrs, cells were removed from cell culture plates, stained with a cocktail phenotyping antibodies and live/dead cell viability dye, and analyzed by FACS. In order to quantify the number of live target cells present in the wells, 20 μl CountBright™ absolute counting beads were added to the wells just prior to acquisition. For the assessment of specificity of killing, cells were gated on Violet cell tracker labeled populations. Percent survival of target cells was calculated as followed: Target survival=$(R_1/R_2)*100$, where $R_1$=absolute number of live target cells in the presence of effector cells and antibody, and $R_2$=number of live target cells only (cultured without effector cells or test antibody).

Human CD8+ T cells were gated as CD45+/CD14−/CD4−/CD8+. Cynomolgus CD8+ T cells were gated as CD45+/CD20−/CD14−/CD4−/CD8+ T cell activation was reported as the percent of CD25+ or CD69+ T cells out of total CD8+ T cells.

EC50 values for target cell survival and T cell activation were calculated using 4-parameter non-linear regression analysis in Prism software.

Anti-BCMA×anti-CD3 bispecific antibodies were tested for their ability to activate resting human and cynomolgus T cells to kill a panel of BCMA expressing cells with differing surface BCMA levels. With resting human T cells as effector cells, REGN5458 mediated killing of 5 different BCMA cell lines with $EC_{50}$ values ranging from $7.07 \times 10^{-10}$ M to $3.45 \times 10^{-11}$ M. REGN5459 showed killing of the same 5 cell lines with EC50s values ranging from $1.66 \times 10^{-9}$ M to $1.06 \times 10^{-10}$ M. $EC_{50}$s for T cell activation, as measured by CD25 upregulation on CD8+ T cells were similar to killing $EC_{50}$s. Modest T cell activation was observed in the presence of 1-arm CD3 isotype control mAb17664D, but only for the U266 cell line. No cytotoxicity was observed for the isotype controls tested.

BCMA×CD3 mediated killing by cynomolgus T cells was tested only on the MM cell line H929. The $EC_{50}$ for cytotoxicity mediated by REGN5458 and REGN5459 was $2.34 \times 10^{-11}$ and $6.92 \times 10^{-11}$ respectively. No cytotoxicity or T cell activation was observed for the isotype control antibody mAb15260 with either human or cynomolgus effector cells. The results are shown in Tables 15A, 15B and 16, below.

TABLE 15A

Median $EC_{50}$, Human Effector Cells

| | H929 (40000 ABC) | | | MM1S (18000 ABC) | | | U266 (13000 ABC) | | |
|---|---|---|---|---|---|---|---|---|---|
| REGN# | n | % Survival | % T activation | n | % Survival | % T activation | n | % Survival | % T activation |
| REGN5458 | 3 | 1.03E−10 | 2.11E−10 | 2 | 6.46E−11 | 7.06E−11 | 1 | 3.28E−10 | 1.07E−10 |
| REGN5459 | 4 | 3.01E−10 | 3.00E−10 | 2 | 2.88E−10 | 4.58E−10 | 1 | 1.66E−09 | 4.69E−10 |

TABLE 15B

Median $EC_{50}$, Human Effector Cells

| | RPMI8226 (10000 ABC) | | | Molp8 (2000 ABC) | | |
|---|---|---|---|---|---|---|
| REGN# | n | % Survival | % T activation | n | % Survival | % T activation |
| REGN5458 | 1 | 3.45E−11 | 6.49E−11 | 2 | 7.07E−10 | 1.10E−9 |
| REGN5459 | 1 | 1.06E−10 | 7.50E−10 | 3 | 1.36E−09 | 6.47E−9 |

TABLE 16

Median $EC_{50}$, Cynomolgus effector cells

| | H929 | | |
|---|---|---|---|
| REGN# | n | % Survival | % T activation |
| REGN5458 | 4 | 2.34E−11 | 6.83E−11 |
| REGN5459 | 4 | 6.92E−11 | 1.58E−10 |

Example 9: FACS Cytotoxicity Assay to Autologous T Cell-Mediated Killing of Primary Multiple Myeloma Blast Cells in the Presence of Anti-BCMA×Anti-CD3 Bispecific Antibodies In order to monitor the specific killing of multiple myeloma cells by flow cytometry, bone marrow mononuclear cells (BMMC) from multiple myeloma patients were plated on human stromal cells (HS5) and rested overnight at 37 C. Separately, matching patient peripheral blood mononuclear cells (PBMC) were thawed and cultured in supplemented RPMI media at $1 \times 10^6$ cells/mL overnight at 37° C. in order to enrich for lymphocytes by depleting adherent cells. The next day, BMMC were co-incubated with adherent cell-depleted naïve PBMC on stromal cells (HS5) and a serial 10× dilution of BCMA×CD3 bispecific or 1-arm CD3 isotype control (starting concentration 66.7 nM) at 37° C. Cells were removed from cell culture plates at day 3, 4 or 7 and analyzed by FACS. For the assessment of specificity of killing, multiple myeloma cells were gated as single, live, CD90 negative (to exclude stromal cells), CD2 negative, CD56 positive. CD45 was low on multiple myeloma cells in most samples except MM455. Percent of live target cells was reported for the calculation of adjusted survival as follows: Adjusted survival=$(R1/R2)*100$, where R1=% live target cells in the presence of antibody, and R2=% live target cells in the absence of test antibody.

T cells were gated as CD2 positive, CD56 negative and either CD4 or CD8 positive. T cell activation was reported as the percent of CD25+CD4 or CD8 T cells out of total CD4 or CD8 T cells.

BCMAxCD3 bispecific antibodies were tested for their ability to redirect killing of primary multiple myeloma blast cells by autologous donor PBMC. Maximal BCMAxCD3 mediated cytotoxicity of primary MM blast ranged from 52-96%, with EC50s ranging from $9.89 \times 10^{-11}$ M to $3.67 \times 10^{-9}$ M for REGN5458 and $4.96 \times 10^{-10}$ M to $7.94 \times 10^{-8}$ M for REGN5459. T cell activation was measured by assessing the upregulation of CD25 on CD8+ T cells. EC50s of T cell activation ranged from $3.23 \times 10^{-9}$ to $1.69 \times 10^{-10}$. Modest cytotoxicity and T cell activation was observed for the 1-arm CD3 (no target binding) isotype control. Results are shown in Tables 17A and 17B, below.

TABLE 17A

MM % lysis

| Sample ID | Disease Stage | E:T ratio | length of treatment | % MM lysis at 66 nM REGN5458 | % MM lysis at 66 nM REGN5459 | % MM lysis at 66 nM Isotype |
|---|---|---|---|---|---|---|
| MM2 | newly diagnosed | 1.4 | 7 days | 88 | 85 | 27.5 |
| MM369 | newly diagnosed | 0.3 | 3 days | 96 | 94 | 0 |
| MM453 | newly diagnosed | 2.4 | 3 days | 82 | 80 | 40 |
| MM455 | progression, treated | 0.4 | 3 days | 63 | 52 | 24 |

TABLE 17B

MM lysis EC50 and T cell activation

| Sample ID | Disease Stage | E:T ratio | length of treatment | MM Lysis EC50 REGN5458 | MM lysis EC50 REGN5459 | CD25 upreg EC50 REGN5456 | CD25 upreg EC50 REGN5456 |
|---|---|---|---|---|---|---|---|
| MM2 | newly diagnosed | 1.4 | 7 days | 7.47E-10 | 7.24E-09 | Not done | Not done |
| MM369 | newly diagnosed | 0.3 | 3 days | 1.07E-10 | 4.96E-10 | 1.69E-10 | 2.03E-10 |
| MM453 | newly diagnosed | 2.4 | 3 days | 9.89E-11 | 1.19E-09 | 1.71E-10 | 3.23E-9 |
| MM455 | progression, treated | 0.4 | 3 days | 3.67E-09 | 7.94E-08 | 2.06E-10 | 1.16E-9 |

Example 10: Anti-BCMAxAnti-CD3 Bispecific Antibodies Prevent Growth of BCMA-Expressing Tumors (NCI-H929) In Vivo in a Xenogenic Tumor Model To determine the in vivo efficacy of BCMAxCD3 bispecific antibodies (Abs), a xenogenic tumor study was performed. Immunodeficient NOD.Cg-Prkdc$^{scid}$Il2rg$^{tm1Wjl}$/SzJ (NSG) mice were subcutaneously implanted with a mixture of $10 \times 10^6$ BCMA-expressing NCI-H929 multiple myeloma cells and $0.5 \times 10^6$ human peripheral blood mononuclear cells (PBMC) isolated from a normal donor. The mice (n=7 per group) were immediately administered a PBS vehicle control, an irrelevant anti-FelD1 bivalent isotype control Ab (REGN2759), a CD3-binding control bispecific Ab (mAb17664D), a BCMAxCD3 (G; REGN5458) bispecific Ab, or a BCMAxCD3 (G20; REGN5459) bispecific Ab at a dose of 4 mg/kg. The mice were administered Abs twice per week for a total of three weeks, and tumor growth was assessed over 40 days. While BCMA+ tumors grew similarly in the vehicle-, isotype control-, and CD3-binding control-treated mice, both BCMAxCD3 Abs that were tested prevented the growth of tumors in vivo.

Implantation and measurement of syngeneic tumors: NSG mice were subcutaneously implanted with a mixture of $10 \times 10^6$ BCMA-expressing NCI-H929 multiple myeloma cells and $0.5 \times 10^6$ PBMC derived from a normal donor. The mice (n=7 per group) were immediately administered a PBS vehicle control, an irrelevant anti-FelD1 bivalent isotype control Ab (REGN2759), a CD3-binding control bispecific Ab (mAb17664D), a BCMAxCD3 (G; REGN5458) bispecific Ab, or a BCMAxCD3 (G20; REGN5459) bispecific Ab at a dose of 4 mg/kg. The mice were administered Abs twice per week for a total of three weeks. Tumor growth was measured with calipers twice per week for the duration of the experiment. Mice were sacrificed 40 days after tumor implantation.

Calculation of syngeneic tumor growth and inhibition: In order to determine tumor volume by external caliper, the greatest longitudinal diameter (length in mm) and the greatest transverse diameter (width in mm) were determined. Tumor volumes based on caliper measurements were calculated by the formula: Volume (mm$^3$)=(length×width$^2$)/2.

BCMAxCD3 bispecific Abs prevented the growth of BCMA+ NCI-H929 tumors in vivo in a xenogenic tumor model. Results are shown in Table 18, below.

TABLE 18

Average Tumor Size at Various Time Points

| Antibody (4 mg/kg) | Average Tumor Size (mm3) ± SEM on Day 4 |
|---|---|
| PBS (Vehicle Control) | 67.1 ± 5.9 |
| REGN2759 (Isotype Control) | 62.6 ± 3.7 |
| mAb17664D (CD3 Binding Control) | 76.1 ± 7.6 |
| REGN5458 (BCMA x CD3-G) | 39.5 ± 9.1 |
| REGN5459 (BCMA x CD3-G20) | 26.5 ± 6.2 |

TABLE 18-continued

Average Tumor Size at Various Time Points

Antibody (4 mg/kg)

| | Average Tumor Size (mm3) ± SEM on Day 7 |
|---|---|
| PBS (Vehicle Control) | 123.0 ± 25.2 |
| REGN2759 (Isotype Control) | 109.7 ± 20.3 |
| mAb17664D (CD3 Binding Control) | 182.0 ± 19.4 |
| REGN5458 (BCMA × CD3-G) | 0 ± 0 |
| REGN5459 (BCMA × CD3-G20) | 0 ± 0 |

| | Average Tumor Size (mm3) ± SEM on Day 11 |
|---|---|
| PBS (Vehicle Control) | 361.5 ± 35.7 |
| REGN2759 (Isotype Control) | 415.3 ± 11.4 |
| mAb17664D (CD3 Binding Control) | 449.6 ± 46.6 |
| REGN5458 (BCMA × CD3-G) | 0 ± 0 |
| REGN5459 (BCMA × CD3-G20) | 0 ± 0 |

| | Average Tumor Size (mm3) ± SEM on Day 14 |
|---|---|
| PBS (Vehicle Control) | 581.4 ± 57.9 |
| REGN2759 (Isotype Control) | 734.3 ± 41.8 |
| mAb17664D (CD3 Binding Control) | 741.2 ± 56.0 |
| REGN5458 (BCMA × CD3-G) | 0 ± 0 |
| REGN5459 (BCMA × CD3-G20) | 0 ± 0 |

| | Average Tumor Size (mm3) ± SEM on Day 18 |
|---|---|
| PBS (Vehicle Control) | 1033.4 ± 143.7 |
| REGN2759 (Isotype Control) | 1586.1 ± 101.4 |
| mAb17664D (CD3 Binding Control) | 1511.4 ± 80.7 |
| REGN5458 (BCMA × CD3-G) | 0 ± 0 |
| REGN5459 (BCMA × CD3-G20) | 0 ± 0 |

| | Average Tumor Size (mm3) ± SEM on Day 21 |
|---|---|
| PBS (Vehicle Control) | 1730.9 ± 244.8 |
| REGN2759 (Isotype Control) | 2554.7 ± 148.8 |
| mAb17664D (CD3 Binding Control) | 2474.0 ± 132.6 |
| REGN5458 (BCMA × CD3-G) | 0 ± 0 |
| REGN5459 (BCMA × CD3-G20) | 0 ± 0 |

| | Average Tumor Size (mm3) ± SEM on Day 28 |
|---|---|
| PBS (Vehicle Control) | Euthanized - Not measured |
| REGN2759 (Isotype Control) | Euthanized - Not measured |
| mAb17664D (CD3 Binding Control) | Euthanized - Not measured |
| REGN5458 (BCMA × CD3-G) | 0 ± 0 |
| REGN5459 (BCMA × CD3-G20) | 0 ± 0 |

| | Average Tumor Size (mm3) ± SEM on Day 40 |
|---|---|
| PBS (Vehicle Control) | Euthanized - Not measured |
| REGN2759 (Isotype Control) | Euthanized - Not measured |
| mAb17664D (CD3 Binding Control) | Euthanized - Not measured |
| REGN5458 (BCMA × CD3-G) | 0 ± 0 |
| REGN5459 (BCMA × CD3-G20) | 0 ± 0 |

Example 11: Anti-BCMA×Anti-CD3 Bispecific Antibodies Prevent Growth of BCMA-Expressing Tumors (NCI-H929) in a Dose-Dependent Manner in a Xenogenic In Vivo Tumor Model To determine the in vivo efficacy of anti-BCMA×anti-CD3 bispecific antibodies (Abs), a xenogenic tumor study was performed. Immunodeficient NOD.Cg-Prkdc$^{scid}$Il2rg$^{tm1Wjl}$/SzJ (NSG) mice were subcutaneously implanted with a mixture of 10×10$^6$ BCMA-expressing NCI-H929 human multiple myeloma tumor cells and 0.5×10$^6$ human peripheral blood mononuclear cells (PBMC) isolated from a normal, healthy donor. The mice (n=7 per group) were then immediately administered a PBS vehicle control, a CD3-binding control bispecific Ab (G; mAb17664D) at a dose of 4 mg/kg, a CD3-binding control bispecific Ab (G20; REGN4460) at a dose of 4 mg/kg, a BCMA×CD3 (G; REGN5458) bispecific Ab at doses of either 4 mg/kg, 0.4 mg/kg, or 0.04 mg/kg, or a BCMA×CD3 (G20; REGN5459) bispecific Ab at doses of either 4 mg/kg, 0.4 mg/kg, or 0.04 mg/kg. The mice were administered these Abs twice per week for a total of seven doses, and tumor growth was assessed over 60 days. While BCMA$^+$ NCI-H929 tumors grew similarly in the vehicle- and CD3-binding control-treated mice, both anti-BCMA×anti-CD3 Abs that were tested prevented the growth of tumors in a dose-dependent manner in vivo.

Implantation and measurement of xenogenic tumors: NSG mice were subcutaneously implanted with a mixture of 10×10$^6$ BCMA-expressing NCI-H929 multiple myeloma cells and 0.5×10$^6$ PBMC derived from a normal, healthy donor. The mice (n=7 per group) were immediately administered a PBS vehicle control, a CD3-binding control bispecific Ab (G; mAb17664D), a CD3-binding control bispecific Ab (G20; REGN4460), a BCMA×CD3 (G; REGN5458) bispecific Ab, or a BCMA×CD3 (G20; REGN5459) bispecific Ab. mAb17664D and REGN4460 were dosed at 4 mg/kg, while REGN5458 and REGN5459 were administered at either 4 mg/kg, 0.4 mg/kg, or 0.04 mg/kg. The mice were administered Abs twice per week for a total of seven doses. Tumor growth was measured with calipers twice per week for the duration of the experiment.

Calculation of xenogenic tumor growth and inhibition: In order to determine tumor volume by external caliper, the greatest longitudinal diameter (length in mm) and the greatest transverse diameter (width in mm) were determined. Tumor volumes based on caliper measurements were calculated by the formula: Volume (mm$^3$)=(length×width$^2$)/2.

Figure 2:
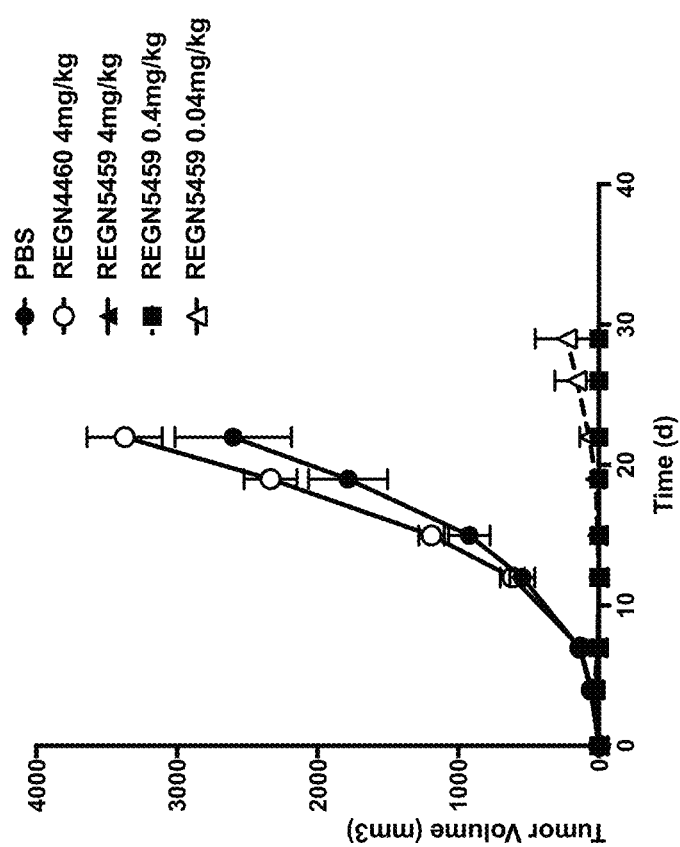

BCMA×CD3 bispecific Abs prevented the growth of BCMA$^+$ NCI-H929 tumors in a dose-dependent manner in this xenogenic in vivo tumor model. Results are shown in Table 19, below, and illustrated in FIGS. 1 and 2.

TABLE 19

Average Tumor Size at Various Time Points

Antibody Treatment

| | Average Tumor Size (mm3) ± SEM on Day 4 |
|---|---|
| PBS (Vehicle Control) | 60.1 ± 7.9 |
| mAb17664D (CD3 Binding Control-G) - 4 mg/kg | 42.5 ± 4.7 |
| REGN4460 (CD3 Binding Control-G20) - 4 mg/kg | 52.0 ± 5.9 |
| REGN5458 (BCMA × CD3-G) - 4 mg/kg | 18.0 ± 1.2 |
| REGN5458 (BCMA × CD3-G) - 0.4 mg/kg | 31.9 ± 2.0 |
| REGN5458 (BCMA × CD3-G) - 0.04 mg/kg | 32.0 ± 2.9 |
| REGN5459 (BCMA × CD3-G20) - 4 mg/kg | 21.8 ± 3.4 |
| REGN5459 (BCMA × CD3-G20) - 0.4 mg/kg | 19.6 ± 4.4 |
| REGN5459 (BCMA × CD3-G20) - 0.04 mg/kg | 33.0 ± 4.4 |

| | Average Tumor Size (mm3) ± SEM on Day 7 |
|---|---|
| PBS (Vehicle Control) | 138.2 ± 25.1 |
| mAb17664D (CD3 Binding Control-G) - 4 mg/kg | 108.6 ± 17.8 |
| REGN4460 (CD3 Binding Control-G20) - 4 mg/kg | 132.4 ± 21.1 |
| REGN5458 (BCMA × CD3-G) - 4 mg/kg | 1.3 ± 1.3 |

TABLE 19-continued

Average Tumor Size at Various Time Points

| Antibody Treatment | |
|---|---|
| REGN5458 (BCMA x CD3-G) - 0.4 mg/kg | 11.3 ± 3.0 |
| REGN5458 (BCMA x CD3-G) - 0.04 mg/kg | 30.8 ± 5.5 |
| REGN5459 (BCMA x CD3-G20) - 4 mg/kg | 8.0 ± 4.3 |
| REGN5459 (BCMA x CD3-G20) - 0.4 mg/kg | 7.3 ± 3.6 |
| REGN5459 (BCMA x CD3-G20) - 0.04 mg/kg | 8.4 ± 4.0 |

Average Tumor Size (mm3) ± SEM on Day 12

| Antibody Treatment | |
|---|---|
| PBS (Vehicle Control) | 545.4 ± 88.7 |
| mAb17664D (CD3 Binding Control-G) - 4 mg/kg | 493.4 ± 67.5 |
| REGN4460 (CD3 Binding Control-G20) - 4 mg/kg | 616.2 ± 84.4 |
| REGN5458 (BCMA x CD3-G) - 4 mg/kg | 0 ± 0 |
| REGN5458 (BCMA x CD3-G) - 0.4 mg/kg | 1.6 ± 1.6 |
| REGN5458 (BCMA x CD3-G) - 0.04 mg/kg | 71.5 ± 22.4 |
| REGN5459 (BCMA x CD3-G20) - 4 mg/kg | 1.7 ± 1.7 |
| REGN5459 (BCMA x CD3-G20) - 0.4 mg/kg | 0 ± 0 |
| REGN5459 (BCMA x CD3-G20) - 0.04 mg/kg | 0 ± 0 |

Average Tumor Size (mm3) ± SEM on Day 15

| Antibody Treatment | |
|---|---|
| PBS (Vehicle Control) | 921.4 ± 147.5 |
| mAb17664D (CD3 Binding Control-G) - 4 mg/kg | 874.8 ± 86.6 |
| REGN4460 (CD3 Binding Control-G20) - 4 mg/kg | 1190.7 ± 91.2 |
| REGN5458 (BCMA x CD3-G) - 4 mg/kg | 0 ± 0 |
| REGN5458 (BCMA x CD3-G) - 0.4 mg/kg | 0 ± 0 |
| REGN5458 (BCMA x CD3-G) - 0.04 mg/kg | 133.4 ± 50.9 |
| REGN5459 (BCMA x CD3-G20) - 4 mg/kg | 0 ± 0 |
| REGN5459 (BCMA x CD3-G20) - 0.4 mg/kg | 0 ± 0 |
| REGN5459 (BCMA x CD3-G20) - 0.04 mg/kg | 7.9 ± 7.9 |

Average Tumor Size (mm3) ± SEM on Day 19

| Antibody Treatment | |
|---|---|
| PBS (Vehicle Control) | 1785.3 ± 282.2 |
| mAb17664D (CD3 Binding Control-G) - 4 mg/kg | 1833.4 ± 186.6 |
| REGN4460 (CD3 Binding Control-G20) - 4 mg/kg | 2336.5 ± 188.3 |
| REGN5458 (BCMA x CD3-G) - 4 mg/kg | 0 ± 0 |
| REGN5458 (BCMA x CD3-G) - 0.4 mg/kg | 0 ± 0 |
| REGN5458 (BCMA x CD3-G) - 0.04 mg/kg | 413.7 ± 162.7 |
| REGN5459 (BCMA x CD3-G20) - 4 mg/kg | 0 ± 0 |
| REGN5459 (BCMA x CD3-G20) - 0.4 mg/kg | 0 ± 0 |
| REGN5459 (BCMA x CD3-G20) - 0.04 mg/kg | 23.1 ± 23.1 |

Average Tumor Size (mm3) ± SEM on Day 22

| Antibody Treatment | |
|---|---|
| PBS (Vehicle Control) | 2601.5 ± 414.5 |
| mAb17664D (CD3 Binding Control-G) - 4 mg/kg | 2878.5 ± 257.6 |
| REGN4460 (CD3 Binding Control-G20) - 4 mg/kg | 3374.3 ± 267.2 |
| REGN5458 (BCMA x CD3-G) - 4 mg/kg | 0 ± 0 |
| REGN5458 (BCMA x CD3-G) - 0.4 mg/kg | 0 ± 0 |
| REGN5458 (BCMA x CD3-G) - 0.04 mg/kg | 669.4 ± 248.5 |
| REGN5459 (BCMA x CD3-G20) - 4 mg/kg | 0 ± 0 |
| REGN5459 (BCMA x CD3-G20) - 0.4 mg/kg | 0 ± 0 |
| REGN5459 (BCMA x CD3-G20) - 0.04 mg/kg | 69.5 ± 69.5 |

Average Tumor Size (mm3) ± SEM on Day 26

| Antibody Treatment | |
|---|---|
| PBS (Vehicle Control) | Animals Euthanized |
| mAb17664D (CD3 Binding Control-G) - 4 mg/kg | Animals Euthanized |
| REGN4460 (CD3 Binding Control-G20) - 4 mg/kg | Animals Euthanized |
| REGN5458 (BCMA x CD3-G) - 4 mg/kg | 0 ± 0 |
| REGN5458 (BCMA x CD3-G) - 0.4 mg/kg | 0 ± 0 |
| REGN5458 (BCMA x CD3-G) - 0.04 mg/kg | 1167.0 ± 431.7 |
| REGN5459 (BCMA x CD3-G20) - 4 mg/kg | 0 ± 0 |
| REGN5459 (BCMA x CD3-G20) - 0.4 mg/kg | 0 ± 0 |
| REGN5459 (BCMA x CD3-G20) - 0.04 mg/kg | 156.7 ± 156.7 |

Average Tumor Size (mm3) ± SEM on Day 29

| Antibody Treatment | |
|---|---|
| PBS (Vehicle Control) | Animals Euthanized |
| mAb17664D (CD3 Binding Control-G) - 4 mg/kg | Animals Euthanized |
| REGN4460 (CD3 Binding Control-G20) - 4 mg/kg | Animals Euthanized |
| REGN5458 (BCMA x CD3-G) - 4 mg/kg | 0 ± 0 |
| REGN5458 (BCMA x CD3-G) - 0.4 mg/kg | 0 ± 0 |
| REGN5458 (BCMA x CD3-G) - 0.04 mg/kg | 1781.8 ± 620.7 |
| REGN5459 (BCMA x CD3-G20) - 4 mg/kg | 0 ± 0 |
| REGN5459 (BCMA x CD3-G20) - 0.4 mg/kg | 0 ± 0 |
| REGN5459 (BCMA x CD3-G20) - 0.04 mg/kg | 226.6 ± 226.6 |

Average Tumor Size (mm3) ± SEM on Day 34

| Antibody Treatment | |
|---|---|
| PBS (Vehicle Control) | Animals Euthanized |
| mAb17664D (CD3 Binding Control-G) - 4 mg/kg | Animals Euthanized |
| REGN4460 (CD3 Binding Control-G20) - 4 mg/kg | Animals Euthanized |
| REGN5458 (BCMA x CD3-G) - 4 mg/kg | 0 ± 0 |
| REGN5458 (BCMA x CD3-G) - 0.4 mg/kg | 0 ± 0 |
| REGN5458 (BCMA x CD3-G) - 0.04 mg/kg | Animals Euthanized |
| REGN5459 (BCMA x CD3-G20) - 4 mg/kg | 0 ± 0 |
| REGN5459 (BCMA x CD3-G20) - 0.4 mg/kg | 0 ± 0 |
| REGN5459 (BCMA x CD3-G20) - 0.04 mg/kg | Animals Euthanized |

Average Tumor Size (mm3) ± SEM on Day 39

| Antibody Treatment | |
|---|---|
| PBS (Vehicle Control) | Animals Euthanized |
| mAb17664D (CD3 Binding Control-G) - 4 mg/kg | Animals Euthanized |
| REGN4460 (CD3 Binding Control-G20) - 4 mg/kg | Animals Euthanized |
| REGN5458 (BCMA x CD3-G) - 4 mg/kg | 0 ± 0 |
| REGN5458 (BCMA x CD3-G) - 0.4 mg/kg | 0 ± 0 |
| REGN5458 (BCMA x CD3-G) - 0.04 mg/kg | Animals Euthanized |
| REGN5459 (BCMA x CD3-G20) - 4 mg/kg | 0 ± 0 |
| REGN5459 (BCMA x CD3-G20) - 0.4 mg/kg | 0 ± 0 |
| REGN5459 (BCMA x CD3-G20) - 0.04 mg/kg | Animals Euthanized |

Average Tumor Size (mm3) ± SEM on Day 42

| Antibody Treatment | |
|---|---|
| PBS (Vehicle Control) | Animals Euthanized |
| mAb17664D (CD3 Binding Control-G) - 4 mg/kg | Animals Euthanized |
| REGN4460 (CD3 Binding Control-G20) - 4 mg/kg | Animals Euthanized |
| REGN5458 (BCMA x CD3-G) - 4 mg/kg | 0 ± 0 |
| REGN5458 (BCMA x CD3-G) - 0.4 mg/kg | 0 ± 0 |
| REGN5458 (BCMA x CD3-G) - 0.04 mg/kg | Animals Euthanized |
| REGN5459 (BCMA x CD3-G20) - 4 mg/kg | 0 ± 0 |
| REGN5459 (BCMA x CD3-G20) - 0.4 mg/kg | 0 ± 0 |
| REGN5459 (BCMA x CD3-G20) - 0.04 mg/kg | Animals Euthanized |

Average Tumor Size (mm3) ± SEM on Day 46

| Antibody Treatment | |
|---|---|
| PBS (Vehicle Control) | Animals Euthanized |
| mAb17664D (CD3 Binding Control-G) - 4 mg/kg | Animals Euthanized |
| REGN4460 (CD3 Binding Control-G20) - 4 mg/kg | Animals Euthanized |
| REGN5458 (BCMA x CD3-G) - 4 mg/kg | 0 ± 0 |
| REGN5458 (BCMA x CD3-G) - 0.4 mg/kg | 0 ± 0 |
| REGN5458 (BCMA x CD3-G) - 0.04 mg/kg | Animals Euthanized |
| REGN5459 (BCMA x CD3-G20) - 4 mg/kg | 0 ± 0 |
| REGN5459 (BCMA x CD3-G20) - 0.4 mg/kg | 0 ± 0 |
| REGN5459 (BCMA x CD3-G20) - 0.04 mg/kg | Animals Euthanized |

Average Tumor Size (mm3) ± SEM on Day 55

| Antibody Treatment | |
|---|---|
| PBS (Vehicle Control) | Animals Euthanized |
| mAb17664D (CD3 Binding Control-G) - 4 mg/kg | Animals Euthanized |
| REGN4460 (CD3 Binding Control-G20) - 4 mg/kg | Animals Euthanized |
| REGN5458 (BCMA x CD3-G) - 4 mg/kg | 0 ± 0 |
| REGN5458 (BCMA x CD3-G) - 0.4 mg/kg | 0 ± 0 |
| REGN5458 (BCMA x CD3-G) - 0.04 mg/kg | Animals Euthanized |
| REGN5459 (BCMA x CD3-G20) - 4 mg/kg | 0 ± 0 |
| REGN5459 (BCMA x CD3-G20) - 0.4 mg/kg | 0 ± 0 |
| REGN5459 (BCMA x CD3-G20) - 0.04 mg/kg | Animals Euthanized |

TABLE 19-continued

Average Tumor Size at Various Time Points

| Antibody Treatment | Average Tumor Size (mm3) ± SEM on Day 60 |
|---|---|
| PBS (Vehicle Control) | Animals Euthanized |
| mAb17664D (CD3 Binding Control-G) - 4 mg/kg | Animals Euthanized |
| REGN4460 (CD3 Binding Control-G20) - 4 mg/kg | Animals Euthanized |
| REGN5458 (BCMA × CD3-G) - 4 mg/kg | 0 ± 0 |
| REGN5458 (BCMA × CD3-G) - 0.4 mg/kg | 0 ± 0 |
| REGN5458 (BCMA × CD3-G) - 0.04 mg/kg | Animals Euthanized |
| REGN5459 (BCMA × CD3-G20) - 4 mg/kg | 0 ± 0 |
| REGN5459 (BCMA × CD3-G20) - 0.4 mg/kg | 0 ± 0 |
| REGN5459 (BCMA × CD3-G20) - 0.04 mg/kg | Animals Euthanized |

Example 12: Anti-BCMA×Anti-CD3 Bispecific Antibodies Reduce the Size of and Prevent Growth of Established BCMA-Expressing Tumors (NCI-H929) in a Dose-Dependent Manner in a Xenogenic In Vivo Tumor Model To determine the in vivo efficacy of anti-BCMA×anti-CD3 bispecific antibodies (Abs), a xenogenic tumor study was performed. Immunodeficient NOD.Cg-Prkdc$^{scid}$Il2rg$^{tm1Wjl}$/SzJ (NSG) mice were subcutaneously implanted with a mixture of 10×10$^6$ BCMA-expressing NCI-H929 human multiple myeloma tumor cells and 0.5× 10$^6$ human peripheral blood mononuclear cells (PBMC) isolated from a normal, healthy donor. The tumors were allowed to grow and establish for 5 days until they were approximately 70 mm$^3$ in size. On day 5, the mice (n=7-8 per group) were then administered a PBS vehicle control, a CD3-binding control bispecific Ab (G; mAb17664D) at a dose of 4 mg/kg, a CD3-binding control bispecific Ab (G20; REGN4460) at a dose of 4 mg/kg, a BCMA×CD3 (G; REGN5458) bispecific Ab at doses of either 4 mg/kg, 0.4 mg/kg, or 0.04 mg/kg, or a BCMA×CD3 (G20; REGN5459) bispecific Ab at doses of either 4 mg/kg, 0.4 mg/kg, or 0.04 mg/kg. The mice were administered these Abs twice per week for a total of seven doses, and tumor growth was assessed over 55 days. While BCMA$^+$ NCI-H929 tumors grew similarly in the vehicle- and CD3-binding control-treated mice, both BCMA×CD3 Abs that were tested shrank established tumors and prevented the growth of tumors in a dose-dependent manner in vivo.

Implantation and measurement of xenogenic tumors: NSG mice were subcutaneously implanted with a mixture of 10×10$^6$ BCMA-expressing NCI-H929 multiple myeloma cells and 0.5×10$^6$ PBMC derived from a normal, healthy donor. The tumors were allowed to grow and establish for 5 days until they were approximately 70 mm$^3$ in size. On day 5, the mice (n=7-8 per group) were then administered a PBS vehicle control, a CD3-binding control bispecific Ab (G; mAb17664D), a CD3-binding control bispecific Ab (G20; REGN4460), a BCMA×CD3 (G; REGN5458) bispecific Ab, or a BCMA×CD3 (G20; REGN5459) bispecific Ab. mAb17664D and REGN4460 were dosed at 4 mg/kg, while REGN5458 and REGN5459 were administered at either 4 mg/kg, 0.4 mg/kg, or 0.04 mg/kg. The mice were administered Abs twice per week for a total of seven doses. Tumor growth was measured with calipers twice per week for the duration of the experiment.

Calculation of xenogenic tumor growth and inhibition: In order to determine tumor volume by external caliper, the greatest longitudinal diameter (length in mm) and the greatest transverse diameter (width in mm) were determined. Tumor volumes based on caliper measurements were calculated by the formula: Volume (mm$^3$)=(length×width$^2$)/2.

Figure 3:
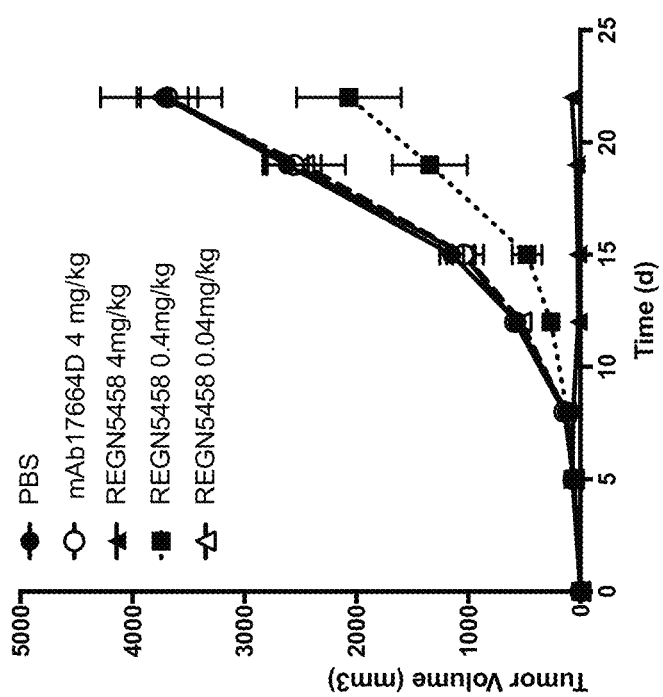
FIGS. 3 and 4 illustrate therapeutic dose-dependent tumor inhibition of established BCMA-expressing NCI-H929 human multiple myeloma tumor cells in vivo by anti-BCMA×anti-CD3 bispecific antibodies REGN5458 and REGN5459, respectively. NCI-H929 cells express high levels of BCMA.
Figure 4:
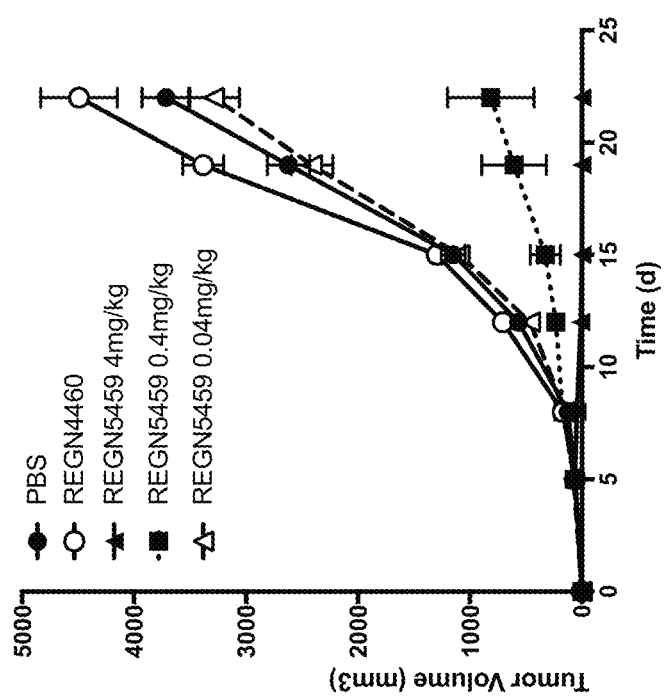

Anti-BCMA×anti-CD3 bispecific antibodies reduced the size of and prevented the growth of established BCMA$^+$ NCI-H929 tumors in a dose-dependent manner in this xenogenic in vivo tumor model. Results are shown in Table 20, below, and illustrated in FIGS. 3 and 4.

TABLE 20

Average Tumor Size at Various Time Points

| Antibody Treatment | Average Tumor Size (mm3) ± SEM on Day 5 |
|---|---|
| PBS (Vehicle Control) | 61.5 ± 6.4 |
| mAb17664D (CD3 Binding Control-G) - 4 mg/kg | 63.7 ± 5.4 |
| REGN4460 (CD3 Binding Control-G20) - 4 mg/kg | 62.6 ± 3.6 |
| REGN5458 (BCMA × CD3-G) - 4 mg/kg | 71.9 ± 10.3 |
| REGN5458 (BCMA × CD3-G) - 0.4 mg/kg | 69.3 ± 7.3 |
| REGN5458 (BCMA × CD3-G) - 0.04 mg/kg | 58.1 ± 5.6 |
| REGN5459 (BCMA × CD3-G20) - 4 mg/kg | 61.8 ± 5.2 |
| REGN5459 (BCMA × CD3-G20) - 0.4 mg/kg | 69.5 ± 4.1 |
| REGN5459 (BCMA × CD3-G20) - 0.04 mg/kg | 74.9 ± 6.4 |
| | Average Tumor Size (mm3) ± SEM on Day 8 |
| PBS (Vehicle Control) | 124.3 ± 17.3 |
| mAb17664D (CD3 Binding Control-G) - 4 mg/kg | 145.3 ± 22.0 |
| REGN4460 (CD3 Binding Control-G20) - 4 mg/kg | 170.7 ± 15.5 |
| REGN5458 (BCMA × CD3-G) - 4 mg/kg | 64.7 ± 16.4 |
| REGN5458 (BCMA × CD3-G) - 0.4 mg/kg | 120.3 ± 16.3 |
| REGN5458 (BCMA × CD3-G) - 0.04 mg/kg | 130.3 ± 16.7 |
| REGN5459 (BCMA × CD3-G20) - 4 mg/kg | 45.8 ± 9.8 |
| REGN5459 (BCMA × CD3-G20) - 0.4 mg/kg | 171.9 ± 23.2 |
| REGN5459 (BCMA × CD3-G20) - 0.04 mg/kg | 152.3 ± 20.0 |
| | Average Tumor Size (mm3) ± SEM on Day 12 |
| PBS (Vehicle Control) | 565.7 ± 64.7 |
| mAb17664D (CD3 Binding Control-G) - 4 mg/kg | 585.0 ± 64.4 |
| REGN4460 (CD3 Binding Control-G20) - 4 mg/kg | 706.8 ± 46.3 |
| REGN5458 (BCMA × CD3-G) - 4 mg/kg | 19.5 ± 10.9 |
| REGN5458 (BCMA × CD3-G) - 0.4 mg/kg | 262.7 ± 61.6 |
| REGN5458 (BCMA × CD3-G) - 0.04 mg/kg | 525.9 ± 71.5 |
| REGN5459 (BCMA × CD3-G20) - 4 mg/kg | 11.5 ± 8.9 |
| REGN5459 (BCMA × CD3-G20) - 0.4 mg/kg | 233.8 ± 63.5 |
| REGN5459 (BCMA × CD3-G20) - 0.04 mg/kg | 462.5 ± 57.7 |
| | Average Tumor Size (mm3) ± SEM on Day 15 |
| PBS (Vehicle Control) | 1150.4 ± 105.7 |
| mAb17664D (CD3 Binding Control-G) - 4 mg/kg | 1041.4 ± 101.3 |
| REGN4460 (CD3 Binding Control-G20) - 4 mg/kg | 1298.4 ± 71.0 |
| REGN5458 (BCMA × CD3-G) - 4 mg/kg | 25.6 ± 19.2 |
| REGN5458 (BCMA × CD3-G) - 0.4 mg/kg | 476.2 ± 133.5 |
| REGN5458 (BCMA × CD3-G) - 0.04 mg/kg | 1031.2 ± 164.3 |
| REGN5459 (BCMA × CD3-G20) - 4 mg/kg | 0 ± 0 |
| REGN5459 (BCMA × CD3-G20) - 0.4 mg/kg | 327.2 ± 135.6 |
| REGN5459 (BCMA × CD3-G20) - 0.04 mg/kg | 1094.2 ± 78.9 |
| | Average Tumor Size (mm3) ± SEM on Day 19 |
| PBS (Vehicle Control) | 2621.3 ± 190.9 |
| mAb17664D (CD3 Binding Control-G) - 4 mg/kg | 2557.5 ± 241.1 |
| REGN4460 (CD3 Binding Control-G20) - 4 mg/kg | 3383.3 ± 183.1 |
| REGN5458 (BCMA × CD3-G) - 4 mg/kg | 40.6 ± 32.8 |
| REGN5458 (BCMA × CD3-G) - 0.4 mg/kg | 1347.5 ± 334.7 |

TABLE 20-continued

Average Tumor Size at Various Time Points

| Antibody Treatment | |
|---|---|
| REGN5458 (BCMA x CD3-G) - 0.04 mg/kg | 2467.5 ± 370.0 |
| REGN5459 (BCMA x CD3-G20) - 4 mg/kg | 0 ± 0 |
| REGN5459 (BCMA x CD3-G20) - 0.4 mg/kg | 606.2 ± 288.8 |
| REGN5459 (BCMA x CD3-G20) - 0.04 mg/kg | 2412.5 ± 184.6 |
| Average Tumor Size (mm3) ± SEM on Day 22 | |
| PBS (Vehicle Control) | 3717.9 ± 214.5 |
| mAb17664D (CD3 Binding Control-G) - 4 mg/kg | 3688.9 ± 272.0 |
| REGN4460 (CD3 Binding Control-G20) - 4 mg/kg | 4492.2 ± 344.0 |
| REGN5458 (BCMA x CD3-G) - 4 mg/kg | 78.3 ± 60.8 |
| REGN5458 (BCMA x CD3-G) - 0.4 mg/kg | 2068.5 ± 465.0 |
| REGN5458 (BCMA x CD3-G) - 0.04 mg/kg | 3745.7 ± 541.2 |
| REGN5459 (BCMA x CD3-G20) - 4 mg/kg | 0 ± 0 |
| REGN5459 (BCMA x CD3-G20) - 0.4 mg/kg | 815.4 ± 387.1 |
| REGN5459 (BCMA x CD3-G20) - 0.04 mg/kg | 3285.9 ± 227.3 |
| Average Tumor Size (mm3) ± SEM on Day 27 | |
| PBS (Vehicle Control) | Animals Euthanized |
| mAb17664D (CD3 Binding Control-G) - 4 mg/kg | Animals Euthanized |
| REGN4460 (CD3 Binding Control-G20) - 4 mg/kg | Animals Euthanized |
| REGN5458 (BCMA x CD3-G) - 4 mg/kg | 252.2 ± 185.1 |
| REGN5458 (BCMA x CD3-G) - 0.4 mg/kg | 3463.9 ± 1025.0 |
| REGN5458 (BCMA x CD3-G) - 0.04 mg/kg | 1589.1 ± 0 |
| REGN5459 (BCMA x CD3-G20) - 4 mg/kg | 0 ± 0 |
| REGN5459 (BCMA x CD3-G20) - 0.4 mg/kg | 1849.9 ± 903.1 |
| REGN5459 (BCMA x CD3-G20) - 0.04 mg/kg | Animals Euthanized |
| Average Tumor Size (mm3) ± SEM on Day 30 | |
| PBS (Vehicle Control) | Animals Euthanized |
| mAb17664D (CD3 Binding Control-G) - 4 mg/kg | Animals Euthanized |
| REGN4460 (CD3 Binding Control-G20) - 4 mg/kg | Animals Euthanized |
| REGN5458 (BCMA x CD3-G) - 4 mg/kg | 411.3 ± 307.2 |
| REGN5458 (BCMA x CD3-G) - 0.4 mg/kg | 2144.2 ± 2144.2 |
| REGN5458 (BCMA x CD3-G) - 0.04 mg/kg | 2886.5 ± 0 |
| REGN5459 (BCMA x CD3-G20) - 4 mg/kg | 0 ± 0 |
| REGN5459 (BCMA x CD3-G20) - 0.4 mg/kg | 661.8 ± 490.1 |
| REGN5459 (BCMA x CD3-G20) - 0.04 mg/kg | Animals Euthanized |
| Average Tumor Size (mm3) ± SEM on Day 35 | |
| PBS (Vehicle Control) | Animals Euthanized |
| mAb17664D (CD3 Binding Control-G) - 4 mg/kg | Animals Euthanized |
| REGN4460 (CD3 Binding Control-G20) - 4 mg/kg | Animals Euthanized |
| REGN5458 (BCMA x CD3-G) - 4 mg/kg | 633.5 ± 473.5 |
| REGN5458 (BCMA x CD3-G) - 0.4 mg/kg | 0 ± 0 |
| REGN5458 (BCMA x CD3-G) - 0.04 mg/kg | Animals Euthanized |
| REGN5459 (BCMA x CD3-G20) - 4 mg/kg | 0 ± 0 |
| REGN5459 (BCMA x CD3-G20) - 0.4 mg/kg | 996.8 ± 771.0 |
| REGN5459 (BCMA x CD3-G20) - 0.04 mg/kg | Animals Euthanized |
| Average Tumor Size (mm3) ± SEM on Day 40 | |
| PBS (Vehicle Control) | Animals Euthanized |
| mAb17664D (CD3 Binding Control-G) - 4 mg/kg | Animals Euthanized |
| REGN4460 (CD3 Binding Control-G20) - 4 mg/kg | Animals Euthanized |
| REGN5458 (BCMA x CD3-G) - 4 mg/kg | 369.5 ± 369.5 |
| REGN5458 (BCMA x CD3-G) - 0.4 mg/kg | 0 ± 0 |
| REGN5458 (BCMA x CD3-G) - 0.04 mg/kg | Animals Euthanized |
| REGN5459 (BCMA x CD3-G20) - 4 mg/kg | 0 ± 0 |
| REGN5459 (BCMA x CD3-G20) - 0.4 mg/kg | 375.6 ± 375.6 |
| REGN5459 (BCMA x CD3-G20) - 0.04 mg/kg | Animals Euthanized |
| Average Tumor Size (mm3) ± SEM on Day 55 | |
| PBS (Vehicle Control) | Animals Euthanized |
| mAb17664D (CD3 Binding Control-G) - 4 mg/kg | Animals Euthanized |
| REGN4460 (CD3 Binding Control-G20) - 4 mg/kg | Animals Euthanized |
| REGN5458 (BCMA x CD3-G) - 4 mg/kg | 0 ± 0 |
| REGN5458 (BCMA x CD3-G) - 0.4 mg/kg | 0 ± 0 |
| REGN5458 (BCMA x CD3-G) - 0.04 mg/kg | Animals Euthanized |
| REGN5459 (BCMA x CD3-G20) - 4 mg/kg | 0 ± 0 |
| REGN5459 (BCMA x CD3-G20) - 0.4 mg/kg | 0 ± 0 |
| REGN5459 (BCMA x CD3-G20) - 0.04 mg/kg | Animals Euthanized |

Example 13: Anti-BCMAxAnti-CD3 Bispecific Antibodies Prevent Growth of BCMA-Expressing Tumors (MOLP-8) in a Dose-Dependent Manner in a Xenogenic In Vivo Tumor Model To determine the in vivo efficacy of anti-BCMAxanti-CD3 bispecific antibodies (Abs), a xenogenic tumor study was performed. Immunodeficient NOD.Cg-Prkdc$^{scid}$Il2rg$^{tm1Wjl}$/SzJ (NSG) mice were subcutaneously implanted with a mixture of $5\times10^6$ BCMA-expressing MOLP-8 human multiple myeloma tumor cells and $1\times10^6$ human peripheral blood mononuclear cells (PBMC) isolated from a normal, healthy donor. The mice (n=7 per group) were then immediately administered a PBS vehicle control, a CD3-binding control bispecific Ab (G; mAb17664D) at a dose of 4 mg/kg, a CD3-binding control bispecific Ab (G20; REGN4460) at a dose of 4 mg/kg, a BCMAxCD3 (G; REGN5458) bispecific Ab at doses of either 4 mg/kg, 0.4 mg/kg, or 0.04 mg/kg, or a BCMAxCD3 (G20; REGN5459) bispecific Ab at doses of either 4 mg/kg, 0.4 mg/kg, or 0.04 mg/kg. The mice were administered these Abs twice per week for a total of seven doses, and tumor growth was assessed over 56 days. While the BCMA$^+$ MOLP-8 tumors grew similarly in the vehicle- and CD3-binding control-treated mice, both BCMAxCD3 Abs that were tested prevented the growth of tumors in a dose-dependent manner in vivo.

Implantation and measurement of xenogenic tumors: NSG mice were subcutaneously implanted with a mixture of $5\times10^6$ BCMA-expressing MOLP-8 multiple myeloma cells and $1\times10^6$ PBMC derived from a normal, healthy donor. The mice (n=7 per group) were immediately administered a PBS vehicle control, a CD3-binding control bispecific Ab (G; mAb17664D), a CD3-binding control bispecific Ab (G20; REGN4460), a BCMAxCD3 (G; REGN5458) bispecific Ab, or a BCMAxCD3 (G20; REGN5459) bispecific Ab. mAb17664D and REGN4460 were dosed at 4 mg/kg, while REGN5458 and REGN5459 were administered at either 4 mg/kg, 0.4 mg/kg, or 0.04 mg/kg. The mice were administered Abs twice per week for a total of seven doses. Tumor growth was measured by caliper twice per week for the duration of the experiment.

Calculation of xenogenic tumor growth and inhibition: In order to determine tumor volume by external caliper, the greatest longitudinal diameter (length in mm) and the greatest transverse diameter (width in mm) were determined. Tumor volumes based on caliper measurements were calculated by the formula: Volume (mm$^3$)=(length×width$^2$)/2.

Figure 5:
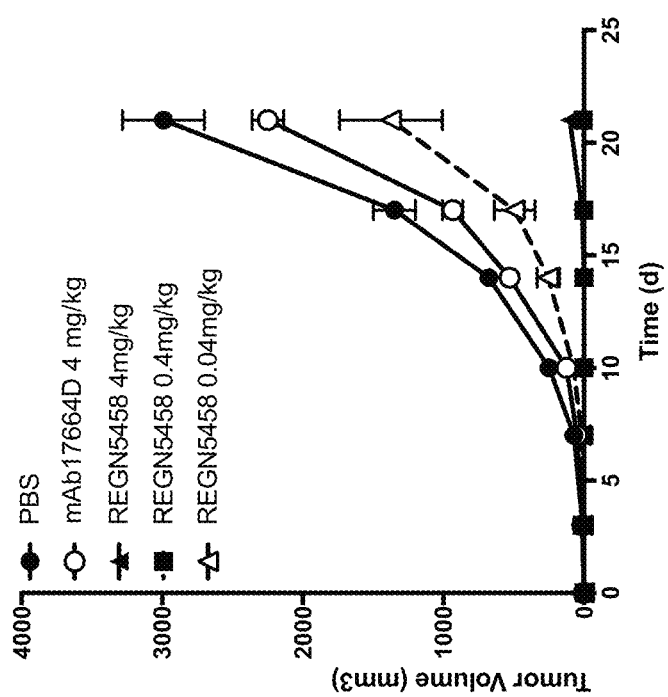
FIGS. 5 and 6 illustrate prophylactic dose-dependent tumor inhibition of BCMA-expressing MOLP-8 human multiple myeloma tumor cells in vivo by anti-BCMA×anti-CD3 bispecific antibodies REGN5458 and REGN5459, respectively. MOLP-8 cells express moderate levels of BCMA.
Figure 6:
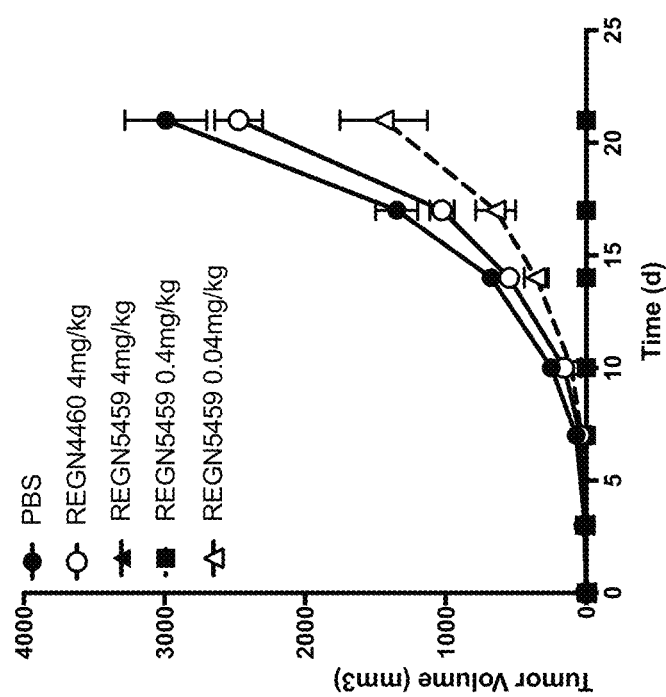

Anti-BCMAxanti-CD3 bispecific antibodies prevented the growth of BCMA$^+$ MOLP-8 tumors in a dose-dependent manner in this xenogenic in vivo tumor model. Results are shown in Table 21, below, and illustrated in FIGS. 5 and 6.

TABLE 21

Average Tumor Size at Various Time Points

Antibody Treatment

| | Average Tumor Size (mm3) ± SEM on Day 3 |
|---|---|
| PBS (Vehicle Control) | 10.3 ± 3.0 |
| mAb17664D (CD3 Binding Control-G) - 4 mg/kg | 11.6 ± 2.0 |
| REGN4460 (CD3 Binding Control-G20) - 4 mg/kg | 14.1 ± 3.9 |
| REGN5458 (BCMA x CD3-G) - 4 mg/kg | 12.5 ± 1.3 |
| REGN5458 (BCMA x CD3-G) - 0.4 mg/kg | 13.5 ± 1.5 |
| REGN5458 (BCMA x CD3-G) - 0.04 mg/kg | 9.3 ± 2.4 |
| REGN5459 (BCMA x CD3-G20) - 4 mg/kg | 12.9 ± 1.3 |
| REGN5459 (BCMA x CD3-G20) - 0.4 mg/kg | 14.0 ± 1.6 |
| REGN5459 (BCMA x CD3-G20) - 0.04 mg/kg | 11.7 ± 2.1 |

| | Average Tumor Size (mm3) ± SEM on Day 7 |
|---|---|
| PBS (Vehicle Control) | 73.4 ± 13.5 |
| mAb17664D (CD3 Binding Control-G) - 4 mg/kg | 50.0 ± 6.6 |
| REGN4460 (CD3 Binding Control-G20) - 4 mg/kg | 45.7 ± 6.1 |
| REGN5458 (BCMA x CD3-G) - 4 mg/kg | 0 ± 0 |
| REGN5458 (BCMA x CD3-G) - 0.4 mg/kg | 1.0 1.0 |
| REGN5458 (BCMA x CD3-G) - 0.04 mg/kg | 18.3 ± 5.0 |
| REGN5459 (BCMA x CD3-G20) - 4 mg/kg | 0.6 ± 0.6 |
| REGN5459 (BCMA x CD3-G20) - 0.4 mg/kg | 0 ± 0 |
| REGN5459 (BCMA x CD3-G20) - 0.04 mg/kg | 37.0 ± 5.7 |

| | Average Tumor Size (mm3) ± SEM on Day 10 |
|---|---|
| PBS (Vehicle Control) | 249.9 ± 47.6 |
| mAb17664D (CD3 Binding Control-G) - 4 mg/kg | 125.0 ± 6.8 |
| REGN4460 (CD3 Binding Control-G20) - 4 mg/kg | 173.9 ± 99 |
| REGN5458 (BCMA x CD3-G) - 4 mg/kg | 0 ± 0 |
| REGN5458 (BCMA x CD3-G) - 0.4 mg/kg | 0 ± 0 |
| REGN5458 (BCMA x CD3-G) - 0.04 mg/kg | 73.9 ± 25.7 |
| REGN5459 (BCMA x CD3-G20) - 4 mg/kg | 0 ± 0 |
| REGN5459 (BCMA x CD3-G20) - 0.4 mg/kg | 0 ± 0 |
| REGN5459 (BCMA x CD3-G20) - 0.04 mg/kg | 104 ± 23.0 |

| | Average Tumor Size (mm3) ± SEM on Day 14 |
|---|---|
| PBS (Vehicle Control) | 677.0 ± 62.7 |
| mAb17664D (CD3 Binding Control-G) - 4 mg/kg | 530.0 ± 44.6 |
| REGN4460 (CD3 Binding Control-G20) - 4 mg/kg | 549.1 ± 59.2 |
| REGN5458 (BCMA x CD3-G) - 4 mg/kg | 0 ± 0 |
| REGN5458 (BCMA x CD3-G) - 0.4 mg/kg | 0 ± 0 |
| REGN5458 (BCMA x CD3-G) - 0.04 mg/kg | 255.4 ± 79.7 |
| REGN5459 (BCMA x CD3-G20) - 4 mg/kg | 0 ± 0 |
| REGN5459 (BCMA x CD3-G20) - 0.4 mg/kg | 0 ± 0 |
| REGN5459 (BCMA x CD3-G20) - 0.04 mg/kg | 356.7 ± 84.6 |

| | Average Tumor Size (mm3) ± SEM on Day 17 |
|---|---|
| PBS (Vehicle Control) | 1349.5 ± 149.7 |
| mAb17664D (CD3 Binding Control-G) - 4 mg/kg | 935.3 ± 71.3 |
| REGN4460 (CD3 Binding Control-G20) - 4 mg/kg | 1027.1 ± 86.6 |
| REGN5458 (BCMA x CD3-G) - 4 mg/kg | 14.5 ± 7.3 |
| REGN5458 (BCMA x CD3-G) - 0.4 mg/kg | 1.7 ± 1.7 |
| REGN5458 (BCMA x CD3-G) - 0.04 mg/kg | 494.3 ± 144.3 |
| REGN5459 (BCMA x CD3-G20) - 4 mg/kg | 0 ± 0 |
| REGN5459 (BCMA x CD3-G20) - 0.4 mg/kg | 0 ± 0 |
| REGN5459 (BCMA x CD3-G20) - 0.04 mg/kg | 645.6 ± 140.9 |

| | Average Tumor Size (mm3) ± SEM on Day 21 |
|---|---|
| PBS (Vehicle Control) | 2990.9 ± 291.7 |
| mAb17664D (CD3 Binding Control-G) - 4 mg/kg | 2249.6 ± 113.5 |
| REGN4460 (CD3 Binding Control-G20) - 4 mg/kg | 2473.4 ± 170.3 |
| REGN5458 (BCMA x CD3-G) - 4 mg/kg | 102.7 ± 66.2 |
| REGN5458 (BCMA x CD3-G) - 0.4 mg/kg | 5.3 ± 5.3 |
| REGN5458 (BCMA x CD3-G) - 0.04 mg/kg | 1373.0 ± 366.6 |
| REGN5459 (BCMA x CD3-G20) - 4 mg/kg | 0 ± 0 |
| REGN5459 (BCMA x CD3-G20) - 0.4 mg/kg | 0 ± 0 |
| REGN5459 (BCMA x CD3-G20) - 0.04 mg/kg | 1442.4 ± 310.7 |

| | Average Tumor Size (mm3) ± SEM on Day 23 |
|---|---|
| PBS (Vehicle Control) | 4155.1 ± 401.8 |
| mAb17664D (CD3 Binding Control-G) - 4 mg/kg | 3288.4 ± 204.6 |
| REGN4460 (CD3 Binding Control-G20) - 4 mg/kg | 3592.7 ± 224.2 |
| REGN5458 (BCMA x CD3-G) - 4 mg/kg | 193.3 ± 117.7 |
| REGN5458 (BCMA x CD3-G) - 0.4 mg/kg | 9.7 ± 9.7 |
| REGN5458 (BCMA x CD3-G) - 0.04 mg/kg | 1882.3 ± 551.5 |
| REGN5459 (BCMA x CD3-G20) - 4 mg/kg | 0 ± 0 |
| REGN5459 (BCMA x CD3-G20) - 0.4 mg/kg | 0 ± 0 |
| REGN5459 (BCMA x CD3-G20) - 0.04 mg/kg | 2124.4 ± 444.1 |

| | Average Tumor Size (mm3) ± SEM on Day 28 |
|---|---|
| PBS (Vehicle Control) | Animals Euthanized |
| mAb17664D (CD3 Binding Control-G) - 4 mg/kg | Animals Euthanized |
| REGN4460 (CD3 Binding Control-G20) - 4 mg/kg | Animals Euthanized |
| REGN5458 (BCMA x CD3-G) - 4 mg/kg | 627.4 ± 318.1 |
| REGN5458 (BCMA x CD3-G) - 0.4 mg/kg | 47.4 ± 47.4 |
| REGN5458 (BCMA x CD3-G) - 0.04 mg/kg | 2542.5 ± 613.3 |
| REGN5459 (BCMA x CD3-G20) - 4 mg/kg | 1.9 ± 1.9 |
| REGN5459 (BCMA x CD3-G20) - 0.4 mg/kg | 0 ± 0 |
| REGN5459 (BCMA x CD3-G20) - 0.04 mg/kg | 1939.3 ± 840.6 |

| | Average Tumor Size (mm3) ± SEM on Day 31 |
|---|---|
| PBS (Vehicle Control) | Animals Euthanized |
| mAb17664D (CD3 Binding Control-G) - 4 mg/kg | Animals Euthanized |
| REGN4460 (CD3 Binding Control-G20) - 4 mg/kg | Animals Euthanized |
| REGN5458 (BCMA x CD3-G) - 4 mg/kg | 1018.5 ± 498.3 |
| REGN5458 (BCMA x CD3-G) - 0.4 mg/kg | 104.7 ± 92.6 |
| REGN5458 (BCMA x CD3-G) - 0.04 mg/kg | 2906.1 ± 532.6 |
| REGN5459 (BCMA x CD3-G20) - 4 mg/kg | 3.8 ± 3.0 |
| REGN5459 (BCMA x CD3-G20) - 0.4 mg/kg | 0 ± 0 |
| REGN5459 (BCMA x CD3-G20) - 0.04 mg/kg | 2688.7 ± 1176.6 |

| | Average Tumor Size (mm3) ± SEM on Day 35 |
|---|---|
| PBS (Vehicle Control) | Animals Euthanized |
| mAb17664D (CD3 Binding Control-G) - 4 mg/kg | Animals Euthanized |
| REGN4460 (CD3 Binding Control-G20) - 4 mg/kg | Animals Euthanized |
| REGN5458 (BCMA x CD3-G) - 4 mg/kg | 1342.9 ± 629.6 |
| REGN5458 (BCMA x CD3-G) - 0.4 mg/kg | 375.1 ± 307.5 |
| REGN5458 (BCMA x CD3-G) - 0.04 mg/kg | 3538.0 ± 0.0 |
| REGN5459 (BCMA x CD3-G20) - 4 mg/kg | 9.3 ± 7.5 |
| REGN5459 (BCMA x CD3-G20) - 0.4 mg/kg | 0 ± 0 |
| REGN5459 (BCMA x CD3-G20) - 0.04 mg/kg | 612.1 ± 0 |

| | Average Tumor Size (mm3) ± SEM on Day 42 |
|---|---|
| PBS (Vehicle Control) | Animals Euthanized |
| mAb17664D (CD3 Binding Control-G) - 4 mg/kg | Animals Euthanized |
| REGN4460 (CD3 Binding Control-G20) - 4 mg/kg | Animals Euthanized |
| REGN5458 (BCMA x CD3-G) - 4 mg/kg | 2363.0 ± 890.2 |
| REGN5458 (BCMA x CD3-G) - 0.4 mg/kg | 968.8 ± 689.2 |
| REGN5458 (BCMA x CD3-G) - 0.04 mg/kg | Animals Euthanized |
| REGN5459 (BCMA x CD3-G20) - 4 mg/kg | 12.8 ± 12.8 |
| REGN5459 (BCMA x CD3-G20) - 0.4 mg/kg | 0 ± 0 |
| REGN5459 (BCMA x CD3-G20) - 0.04 mg/kg | Animals Euthanized |

| | Average Tumor Size (mm3) ± SEM on Day 49 |
|---|---|
| PBS (Vehicle Control) | Animals Euthanized |
| mAb17664D (CD3 Binding Control-G) - 4 mg/kg | Animals Euthanized |
| REGN4460 (CD3 Binding Control-G20) - 4 mg/kg | Animals Euthanized |
| REGN5458 (BCMA x CD3-G) - 4 mg/kg | 1683.5 ± 1683.5 |
| REGN5458 (BCMA x CD3-G) - 0.4 mg/kg | No Recording |

TABLE 21-continued

Average Tumor Size at Various Time Points

| Antibody Treatment | |
|---|---|
| REGN5458 (BCMA × CD3-G) - 0.04 mg/kg | Animals Euthanized |
| REGN5459 (BCMA × CD3-G20) - 4 mg/kg | No Recording |
| REGN5459 (BCMA × CD3-G20) - 0.4 mg/kg | No Recording |
| REGN5459 (BCMA × CD3-G20) - 0.04 mg/kg | Animals Euthanized |
| | Average Tumor Size (mm3) ± SEM on Day 56 |
| PBS (Vehicle Control) | Animals Euthanized |
| mAb17664D (CD3 Binding Control-G) - 4 mg/kg | Animals Euthanized |
| REGN4460 (CD3 Binding Control-G20) - 4 mg/kg | Animals Euthanized |
| REGN5458 (BCMA × CD3-G) - 4 mg/kg | 3108.1 ± 3108.1 |
| REGN5458 (BCMA × CD3-G) - 0.4 mg/kg | 1742.4 ± 635.2 |
| REGN5458 (BCMA × CD3-G) - 0.04 mg/kg | Animals Euthanized |
| REGN5459 (BCMA × CD3-G20) - 4 mg/kg | 17.2 ± 17.2 |
| REGN5459 (BCMA × CD3-G20) - 0.4 mg/kg | 0 ± 0 |
| REGN5459 (BCMA × CD3-G20) - 0.04 mg/kg | Animals Euthanized |

Example 14: Anti-BCMA×Anti-CD3 Bispecific Antibodies Delay Growth of BCMA-Expressing Tumors (MOLP-8) in a Xenographic In Vivo Tumor Model To determine the in vivo efficacy of anti-BCMA×anti-CD3 bispecific antibodies (Abs), a xenogenic tumor study was performed. On day −11, immunodeficient NOD.Cg-Prkdc$^{scid}$Il2rg$^{tm1Wjl}$/SzJ (NSG) mice were intraperitoneally injected with 4×10$^6$ human peripheral blood mononuclear cells (PBMC) from a normal, healthy donor. On day 0, the mice were intravenously administered 2×10$^6$ BCMA$^+$ MOLP-8 human multiple myeloma tumor cells that were engineered to also express firefly luciferase (MOLP-8-luciferase cells). The mice (n=5 per group) were then immediately administered a CD3-binding control bispecific Ab (G; mAb17664D) at a dose of 4 mg/kg or a BCMA×CD3 (G; REGN5458) bispecific Ab at a dose of 4 mg/kg. The mice were administered these Abs twice more on days 3 and 7, for a total of three doses. Tumor growth was assessed over 48 days by measuring tumor bioluminescence (BLI) in anesthetized animals. As a positive control, a group of mice (n=5) was given only MOLP-8-luciferase cells, but not PBMC or antibody. In order to measure background BLI levels, a group of mice (n=5) were untreated and did not receive tumors, PBMC, or antibody. While the BCMA$^+$ MOLP-8-luciferase tumors grew progressively in the CD3-binding control-treated mice, BCMA×CD3 Ab treatment with REGN5458 delayed the growth of tumors in vivo.

Implantation and measurement of xenogenic tumors: On day −11, immunodeficient NOD.Cg-Prkdc$^{scid}$Il2rg$^{tm1Wjl}$/SzJ (NSG) mice were intraperitoneally injected with 5×10$^6$ human PBMC from a normal, healthy donor. On day 0, the mice were intravenously administered 2×10$^6$ BCMA$^+$ MOLP-8-luciferase cells. The mice (n=5 per group) were then immediately administered a CD3-binding control bispecific Ab (G; mAb17664D) at a dose of 4 mg/kg or a BCMA×CD3 (G; REGN5458) bispecific Ab at a dose of 4 mg/kg. The mice were administered these Abs twice more on days 3 and 7, for a total of three doses. Tumor growth was assessed over 48 days by measuring tumor BLI in anesthetized animals. As a positive control, a group of mice (n=5) was given only MOLP-8-luciferase cells, but not PBMC or antibody. In order to measure background BLI levels, a group of mice (n=5) were untreated and did not receive tumors, PBMC, or antibody.

Measurement of xenogenic tumor growth: BLI imaging was used to measure tumor burden. Mice were injected IP with 150 mg/kg of the luciferase substrate D-luciferin suspended in PBS. Five minutes after this injection, BLI imaging of the mice was performed under isoflurane anesthesia using the Xenogen IVIS system. Image acquisition was carried out with the field of view at D, subject height of 1.5 cm, and medium binning level with automatic exposure time determined by the Living Image Software. BLI signals were extracted using Living Image software: regions of interest were drawn around each tumor mass and photon intensities were recorded as p/s/cm2/sr.

Anti-BCMA×anti-CD3 bispecific antibody REGN5458 delayed the growth of BCMA$^+$ MOLP-8-luciferase tumors in this xenogenic in vivo tumor model. Results are shown in Table 22, below.

TABLE 22

Average Tumor Size (by radiance) at Various Time Points

| Antibody Treatment | |
|---|---|
| | Radiance [p/s/cm2$^2$/sr] 8 days post-implantation (mean ± SEM) |
| No tumor (background BLI) | 4.93E+05 ± 1.66E+04 |
| No PBMC/Antibody (positive control) | 5.73E+05 ± 5.27E+04 |
| mAb17664D (CD3 Binding Control-G) - 4 mg/kg | 6.08E+05 ± 5.16E+04 |
| REGN5458 (BCMA × CD3-G) - 4 mg/kg | 5.66E+05 ± 1.97E+04 |
| | Radiance [p/s/cm2$^2$/sr] 15 days post-implantation (mean ± SEM) |
| No tumor (background BLI) | 5.37E+05 ± 1.46E+04 |
| No PBMC/Antibody (positive control) | 1.24E+06 ± 9.67E+04 |
| mAb17664D (CD3 Binding Control-G) - 4 mg/kg | 1.61E+06 ± 9.64E+04 |
| REGN5458 (BCMA × CD3-G) - 4 mg/kg | 5.28E+05 ± 4.13E+04 |
| | Radiance [p/s/cm2$^2$/sr] 22 days post-implantation (mean ± SEM) |
| No tumor (background BLI) | 7.00E+05 ± 1.03E+04 |
| No PBMC/Antibody (positive control) | 1.23E+07 ± 1.02E+06 |
| mAb17664D (CD3 Binding Control-G) - 4 mg/kg | 1.98E+07 ± 8.86E+06 |
| REGN5458 (BCMA × CD3-G) - 4 mg/kg | 1.08E+06 ± 1.71E+05 |
| | Radiance [p/s/cm2$^2$/sr] 24 days post-implantation (mean ± SEM) |
| No tumor (background BLI) | 5.24E+05 ± 1.86E+04 |
| No PBMC/Antibody (positive control) | 1.56E+07 ± 1.29E+06 |
| mAb17664D (CD3 Binding Control-G) - 4 mg/kg | 5.26E+07 ± 1.91E+07 |
| REGN5458 (BCMA × CD3-G) - 4 mg/kg | 1.02E+06 ± 1.99E+05 |
| | Radiance [p/s/cm2$^2$/sr] 28 days post-implantation (mean ± SEM) |
| No tumor (background BLI) | 7.09E+05 ± 2.28E+04 |
| No PBMC/Antibody (positive control) | 3.01E+07 ± 4.78E+06 |
| mAb17664D (CD3 Binding Control-G) - 4 mg/kg | 5.69E+07 ± 2.77E+07 |
| REGN5458 (BCMA × CD3-G) - 4 mg/kg | 3.56E+06 ± 6.34E+05 |
| | Radiance [p/s/cm2$^2$/sr] 30 days post-implantation (mean ± SEM) |
| No tumor (background BLI) | 6.44E+05 ± 4.56E+04 |
| No PBMC/Antibody (positive control) | Animals Euthanized |
| mAb17664D (CD3 Binding Control-G) - 4 mg/kg | Animals Euthanized |
| REGN5458 (BCMA × CD3-G) - 4 mg/kg | 6.92E+06 ± 1.40E+06 |

TABLE 22-continued

Average Tumor Size (by radiance) at Various Time Points

| Antibody Treatment | Radiance [p/s/cm2²/sr] 34 days post-implantation (mean ± SEM) |
|---|---|
| No tumor (background BLI) | 7.78E+05 ± 3.02E+04 |
| No PBMC/Antibody (positive control) | Animals Euthanized |
| mAb17664D (CD3 Binding Control-G) - 4 mg/kg | Animals Euthanized |
| REGN5458 (BCMA × CD3-G) - 4 mg/kg | 2.65E+07 ± 1.36E+07 |
| | Radiance [p/s/cm2²/sr] 37 days post-implantation (mean ± SEM) |
| No tumor (background BLI) | 7.59E+05 ± 2.96E+04 |
| No PBMC/Antibody (positive control) | Animals Euthanized |
| mAb17664D (CD3 Binding Control-G) - 4 mg/kg | Animals Euthanized |
| REGN5458 (BCMA × CD3-G) - 4 mg/kg | 4.52E+07 ± 1.40E+07 |
| | Radiance [p/s/cm2²/sr] 43 days post-implantation (mean ± SEM) |
| No tumor (background BLI) | 6.26E+05 ± 4.18E+04 |
| No PBMC/Antibody (positive control) | Animals Euthanized |
| mAb17664D (CD3 Binding Control-G) - 4 mg/kg | Animals Euthanized |
| REGN5458 (BCMA × CD3-G) - 4 mg/kg | 1.06E+08 ± 3.43E+07 |
| | Radiance [p/s/cm2²/sr] 48 days post-implantation (mean ± SEM) |
| No tumor (background BLI) | 8.24E+05 ± 1.73E+04 |
| No PBMC/Antibody (positive control) | Animals Euthanized |
| mAb17664D (CD3 Binding Control-G) - 4 mg/kg | Animals Euthanized |
| REGN5458 (BCMA × CD3-G) - 4 mg/kg | 3.22E+08 ± 1.27E+08 |

Example 15: Anti-BCMA×Anti-CD3 Bispecific Antibodies Reduce Tumor (OPM-2) Burdens to Background Levels In Vivo To determine the in vivo efficacy of anti-BCMA×anti-CD3 bispecific antibodies (Abs), a xenogenic tumor study was performed. On day 0, immunodeficient NOD.Cg-Prkdc$^{scid}$Il2rg$^{tm1Wjl}$/SzJ (NSG) mice were intravenously administered $2 \times 10^6$ BCMA$^+$ OPM-2 human multiple myeloma tumor cells that were engineered to also express firefly luciferase (OPM-2-luciferase cells). On day 10, the mice were intraperitoneally injected with $4 \times 10^6$ human peripheral blood mononuclear cells (PBMC) from a normal, healthy donor. On day 21, the mice (n=5 per group) were administered a CD3-binding control bispecific Ab (G; mAb17664D) at a dose of 0.4 mg/kg, a BCMA×CD3 (G; REGN5458) bispecific Ab at 0.4 mg/kg, or a BCMA×CD3 (G20; REGN5459) bispecific Ab at 0.4 mg/kg. The mice were administered these Abs twice more on days 25 and 28, for a total of three doses. Tumor growth was assessed through day 61 by measuring tumor bioluminescence (BLI) in anesthetized animals. As a positive control, a group of mice (n=5) was given only OPM-2-luciferase cells, but not PBMC or antibody. In order to measure background BLI levels, a group of mice (n=5) were untreated and did not receive tumors, PBMC, or antibody. While the BCMA$^+$ OPM-2-luciferase tumors grew progressively in the CD3-binding control-treated mice, BCMA×CD3 Ab treatment with REGN5458 and REGN5459 reduced tumor burdens to background levels in the majority of animals.

Implantation and measurement of xenogenic tumors: On day 0, immunodeficient NOD.Cg-Prkdc$^{scid}$Il2rg$^{tm1Wjl}$/SzJ (NSG) mice were intravenously administered $2 \times 10^6$ BCMA$^+$ OPM-2 human multiple myeloma tumor cells that were engineered to also express firefly luciferase (OPM-2-luciferase cells). On day 10, the mice were intraperitoneally injected with $4 \times 10^6$ human peripheral blood mononuclear cells (PBMC) from a normal, healthy donor. On day 21, the mice (n=5 per group) were administered a CD3-binding control bispecific Ab (G; mAb17664D) at a dose of 0.4 mg/kg, a BCMA×CD3 (G; REGN5458) bispecific Ab at 0.4 mg/kg, or a BCMA×CD3 (G20; REGN5459) bispecific Ab at 0.4 mg/kg. The mice were administered these Abs twice more on days 25 and 28, for a total of three doses. Tumor growth was assessed through day 61 by measuring tumor bioluminescence (BLI) in anesthetized animals. As a positive control, a group of mice (n=5) was given only OPM-2-luciferase cells, but not PBMC or antibody. In order to measure background BLI levels, a group of mice (n=5) were untreated and did not receive tumors, PBMC, or antibody.

Measurement of xenogenic tumor growth: BLI imaging was used to measure tumor burden. Mice were injected IP with 150 mg/kg of the luciferase substrate D-luciferin suspended in PBS. Five minutes after this injection, BLI imaging of the mice was performed under isoflurane anesthesia using the Xenogen IVIS system. Image acquisition was carried out with the field of view at D, subject height of 1.5 cm, and medium binning level with automatic exposure time determined by the Living Image Software. BLI signals were extracted using Living Image software: regions of interest were drawn around each tumor mass and photon intensities were recorded as p/s/cm2/sr.

Figure 7:
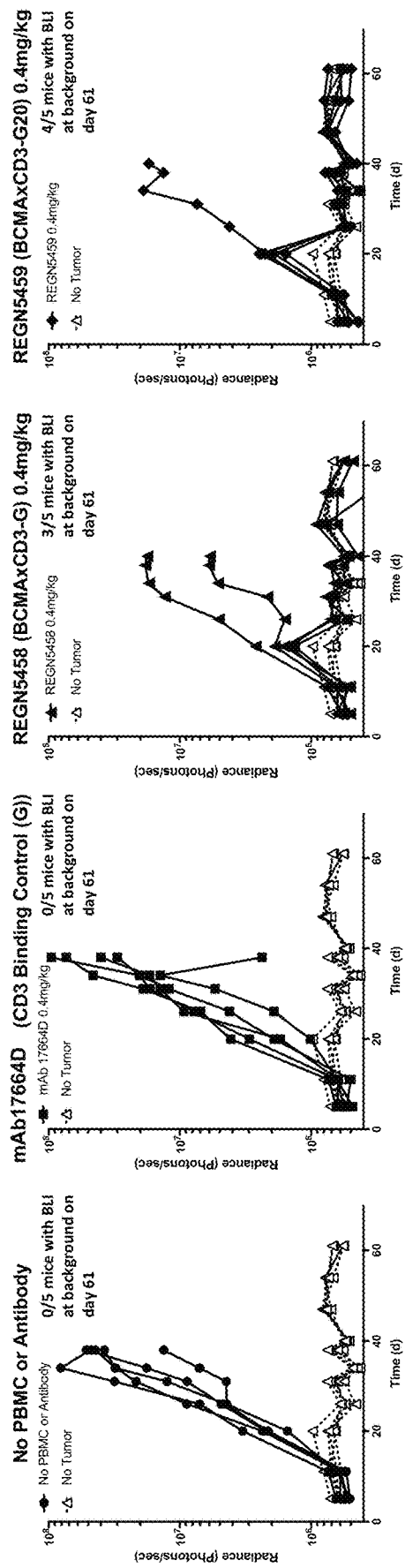
FIG. 7 illustrates a therapeutic reduction in established tumor burden of BCMA-expressing OPM-2 human multiple myeloma tumor cells in vivo by anti-BCMA×anti-CD3 bispecific antibodies REGN5458 and REGN5459, relative to controls. OPM-2 cells express low levels of BCMA.

While the BCMA$^+$ OPM-2-luciferase tumors grew progressively in the CD3-binding control-treated mice, BCMA×CD3 Ab treatment with REGN5458 and REGN5459 reduced tumor burdens to background levels in the majority of animals. Results are shown in Table 23, below, and illustrated in FIG. 7.

TABLE 23

Average Tumor Size (by radiance) at Various Time Points

| Antibody Treatment | Radiance [p/s/cm2²/sr] 5 days post-implantation (mean ± SEM) |
|---|---|
| No tumor (background BLI) | 6.22E+05 ± 2.77E+04 |
| No PBMC/Antibody (positive control) | 5.62E+05 ± 2.75E+04 |
| mAb17664D (CD3 Binding Control-G) - 0.4 mg/kg | 5.73E+05 ± 3.02E+04 |
| REGN5458 (BCMA × CD3-G) - 0.4 mg/kg | 5.87E+05 ± 2.40E+04 |
| REGN5459 (BCMA × CD3-G20) - 0.4 mg/kg | 5.09E+05 ± 3.56E+04 |
| | Radiance [p/s/cm2²/sr] 11 days post-implantation (mean ± SEM) |
| No tumor (background BLI) | 6.90E+05 ± 3.64E+04 |
| No PBMC/Antibody (positive control) | 6.22E+05 ± 3.34E+04 |
| mAb17664D (CD3 Binding Control-G) - 0.4 mg/kg | 6.25E+05 ± 3.80E+04 |
| REGN5458 (BCMA × CD3-G) - 0.4 mg/kg | 6.19E+05 ± 4.39E+04 |
| REGN5459 (BCMA × CD3-G20) - 0.4 mg/kg | 6.45E+05 ± 2.39E+04 |

TABLE 23-continued

Average Tumor Size (by radiance) at Various Time Points

| Antibody Treatment | Radiance [p/s/cm²/sr] |
|---|---|
| | 20 days post-implantation (mean ± SEM) |
| No tumor (background BLI) | 7.59E+05 ± 5.82E+04 |
| No PBMC/Antibody (positive control) | 2.32E+06 ± 2.94E+05 |
| mAb17664D (CD3 Binding Control-G) - 0.4 mg/kg | 2.36E+06 ± 5.46E+05 |
| REGN5458 (BCMA × CD3-G) - 0.4 mg/kg | 1.81E+06 ± 2.37E+05 |
| REGN5459 (BCMA × CD3-G20) - 0.4 mg/kg | 2.13E+06 ± 1.69E+05 |
| | Radiance [p/s/cm²/sr] 26 days post-implantation (mean ± SEM) |
| No tumor (background BLI) | 5.51E+05 ± 2.51E+04 |
| No PBMC/Antibody (positive control) | 5.96E+06 ± 8.74E+05 |
| mAb17664D (CD3 Binding Control-G) - 0.4 mg/kg | 6.05E+06 ± 1.32E+06 |
| REGN5458 (BCMA × CD3-G) - 0.4 mg/kg | 1.73E+06 ± 8.69E+05 |
| REGN5459 (BCMA × CD3-G20) - 0.4 mg/kg | 1.28E+06 ± 7.36E+05 |
| | Radiance [p/s/cm²/sr] 31 days post-implantation (mean ± SEM) |
| No tumor (background BLI) | 6.62E+05 ± 3.35E+04 |
| No PBMC/Antibody (positive control) | 1.58E+07 ± 4.84E+06 |
| mAb17664D (CD3 Binding Control-G) - 0.4 mg/kg | 1.35E+07 ± 2.35E+06 |
| REGN5458 (BCMA × CD3-G) - 0.4 mg/kg | 3.50E+06 ± 2.42E+06 |
| REGN5459 (BCMA × CD3-G20) - 0.4 mg/kg | 1.98E+06 ± 1.36E+06 |
| | Radiance [p/s/cm²/sr] 34 days post-implantation (mean ± SEM) |
| No tumor (background BLI) | 4.57E+05 ± 1.04E+04 |
| No PBMC/Antibody (positive control) | 3.36E+07 ± 1.27E+07 |
| mAb17664D (CD3 Binding Control-G) - 0.4 mg/kg | 2.35E+07 ± 5.72E+06 |
| REGN5458 (BCMA × CD3-G) - 0.4 mg/kg | 4.85E+06 ± 3.24E+06 |
| REGN5459 (BCMA × CD3-G20) - 0.4 mg/kg | 4.24E+06 ± 3.69E+06 |
| | Radiance [p/s/cm²/sr] 38 days post-implantation (mean ± SEM) |
| No tumor (background BLI) | 6.60E+05 ± 3.13E+04 |
| No PBMC/Antibody (positive control) | 3.91E+07 ± 6.87E+06 |
| mAb17664D (CD3 Binding Control-G) - 0.4 mg/kg | 4.84E+07 ± 1.65E+07 |
| REGN5458 (BCMA × CD3-G) - 0.4 mg/kg | 5.30E+06 ± 3.44E+06 |
| REGN5459 (BCMA × CD3-G20) - 0.4 mg/kg | 3.21E+06 ± 2.52E+06 |
| | Radiance [p/s/cm²/sr] 40 days post-implantation (mean ± SEM) |
| No tumor (background BLI) | 5.39E+05 ± 9.67E+03 |
| No PBMC/Antibody (positive control) | Animals euthanized |
| mAb17664D (CD3 Binding Control-G) - 0.4 mg/kg | Animals euthanized |
| REGN5458 (BCMA × CD3-G) - 0.4 mg/kg | 5.06E+06 ± 3.36E+06 |
| REGN5459 (BCMA × CD3-G20) - 0.4 mg/kg | 3.84E+06 ± 3.34E+06 |
| | Radiance [p/s/cm²/sr] 47 days post-implantation (mean ± SEM) |
| No tumor (background BLI) | 7.73E+05 ± 1.91E+04 |
| No PBMC/Antibody (positive control) | Animals euthanized |
| mAb17664D (CD3 Binding Control-G) - 0.4 mg/kg | Animals euthanized |
| REGN5458 (BCMA × CD3-G) - 0.4 mg/kg | 7.76E+05 ± 7.85E+04 |
| REGN5459 (BCMA × CD3-G20) - 0.4 mg/kg | 7.34E+05 ± 2.62E+04 |
| | Radiance [p/s/cm²/sr] 54 days post-implantation (mean ± SEM) |
| No tumor (background BLI) | 7.49E+05 ± 1.95E+04 |
| No PBMC/Antibody (positive control) | Animals euthanized |
| mAb17664D (CD3 Binding Control-G) - 0.4 mg/kg | Animals euthanized |
| REGN5458 (BCMA × CD3-G) - 0.4 mg/kg | 5.78E+05 ± 1.15E+05 |
| REGN5459 (BCMA × CD3-G20) - 0.4 mg/kg | 6.41E+05 ± 5.96E+04 |
| | Radiance [p/s/cm²/sr] 61 days post-implantation (mean ± SEM) |
| No tumor (background BLI) | 6.18E+05 ± 2.77E+04 |
| No PBMC/Antibody (positive control) | Animals euthanized |
| mAb17664D (CD3 Binding Control-G) - 0.4 mg/kg | Animals euthanized |
| REGN5458 (BCMA × CD3-G) - 0.4 mg/kg | 5.23E+05 ± 4.10E+04 |
| REGN5459 (BCMA × CD3-G20) - 0.4 mg/kg | 6.03E+05 ± 5.29E+04 |

Example 16: BCMA×CD3 Bispecific Antibodies Suppress Growth of Syngenic Tumors In Vivo in a Dose-Dependent Manner To determine the in vivo efficacy of anti-BCMA×anti-CD3 bispecific antibodies (Abs), a syngenic tumor study was performed in mice expressing human CD3. C57BL/6 mice that express human CD3deg in place of murine CD3deg (CD3-humanized mice) were subcutaneously implanted with either $0.5 \times 10^6$ B16 melanoma cells that have been engineered to express full-length human BCMA (B16/BCMA cells) or $1 \times 10^6$ MC38 colon carcinoma cells that have been engineered to express full-length human BCMA (MC38/BCMA). The mice (n=7 per group) were then immediately administered a CD3-binding control bispecific Ab (G; mAb17664D) at a dose of 0.4 mg/kg or a BCMA×CD3 (G; REGN5458) bispecific Ab at doses of either 0.4 mg/kg or 0.04 mg/kg. The mice were administered these Abs twice more on days 4 and 7 for a total of three doses, and tumor growth was assessed throughout the experiment. While the B16/BCMA tumors and the MC38/BCMA tumors grew in the CD3-binding control-treated mice, BCMA×CD3 REGN5458 was able to suppress the growth of both tumor lines in a dose-dependent manner in vivo.

Implantation and measurement of syngenic tumors: C57BL/6 mice that express human CD3deg in place of murine CD3deg (CD3-humanized mice) were subcutaneously implanted with either $0.5 \times 10^6$ B16F10 melanoma cells that have been engineered to express full-length human BCMA (B16/BCMA cells) or $1 \times 10^6$ MC38 colon carcinoma cells that have been engineered to express full-length human BCMA (MC38/BCMA). The mice (n=7 per group) were then immediately administered a CD3-binding control bispecific Ab (G; mAb17664D) at a dose of 0.4 mg/kg or a BCMA×CD3 (G; REGN5458) bispecific Ab at doses of either 0.4 mg/kg or 0.04 mg/kg. The mice were administered these Abs twice more on days 4 and 7 for a total of three doses, and tumor growth was assessed throughout the experiment.

Calculation of syngenic tumor growth and inhibition: In order to determine tumor volume by external caliper, the greatest longitudinal diameter (length in mm) and the greatest transverse diameter (width in mm) were determined. Tumor volumes based on caliper measurements were calculated by the formula: Volume (mm$^3$)=(length×width$^2$)/2.

While the B16/BCMA tumors and the MC38/BCMA tumors grew in the CD3-binding control-treated mice, BCMA×CD3 REGN5458 was able to suppress the growth of both tumor lines in a dose-dependent manner in vivo. Results are shown in Table 24, below.

TABLE 24

Average Tumor Size at Various Time Points

Antibody Treatment

| | Average Tumor Size (mm3) ± SEM on Day 5 |
|---|---|
| B16/BCMA Tumor mAb17664D (CD3 Binding Control-G) - 0.4 mg/kg | 25.6 ± 2.7 |
| B16/BCMA Tumor REGN5458 (BCMA × CD3-G) - 0.4 mg/kg | 0.0 ± 0.0 |
| B16/BCMA Tumor REGN5458 (BCMA × CD3-G) - 0.04 mg/kg | 3.3 ± 2.2 |
| MC38/BCMA Tumor mAb17664D (CD3 Binding Control-G) - 0.4 mg/kg | 29.3 ± 4.4 |
| MC38/BCMA Tumor REGN5458 (BCMA × CD3-G) - 0.4 mg/kg | 1.4 ± 1.4 |
| MC38/BCMA Tumor REGN5458 (BCMA × CD3-G) - 0.04 mg/kg | 11.9 ± 2.9 |

| | Average Tumor Size (mm3) ± SEM on Day 10 |
|---|---|
| B16/BCMA Tumor mAb17664D (CD3 Binding Control-G) - 0.4 mg/kg | 179.2 ± 30.6 |
| B16/BCMA Tumor REGN5458 (BCMA × CD3-G) - 0.4 mg/kg | 0.0 ± 0.0 |
| B16/BCMA Tumor REGN5458 (BCMA × CD3-G) - 0.04 mg/kg | 15.4 ± 12.5 |
| MC38/BCMA Tumor mAb17664D (CD3 Binding Control-G) - 0.4 mg/kg | 123.1 ± 14.6 |
| MC38/BCMA Tumor REGN5458 (BCMA × CD3-G) - 0.4 mg/kg | 0.0 ± 0.0 |
| MC38/BCMA Tumor REGN5458 (BCMA × CD3-G) - 0.04 mg/kg | 66.7 ± 22.5 |

| | Average Tumor Size (mm3) ± SEM on Day 14 |
|---|---|
| B16/BCMA Tumor mAb17664D (CD3 Binding Control-G) - 0.4 mg/kg | 763.1 ± 156.2 |
| B16/BCMA Tumor REGN5458 (BCMA × CD3-G) - 0.4 mg/kg | 8.1 ± 4.4 |
| B16/BCMA Tumor REGN5458 (BCMA × CD3-G) - 0.04 mg/kg | 81.4 ± 49.2 |
| MC38/BCMA Tumor mAb17664D (CD3 Binding Control-G) - 0.4 mg/kg | 477.1 ± 77.1 |
| MC38/BCMA Tumor REGN5458 (BCMA × CD3-G) - 0.4 mg/kg | 2.9 ± 2.9 |
| MC38/BCMA Tumor REGN5458 (BCMA × CD3-G) - 0.04 mg/kg | 273.3 ± 115.3 |

| | Average Tumor Size (mm3) ± SEM on Day 18 |
|---|---|
| B16/BCMA Tumor mAb17664D (CD3 Binding Control-G) - 0.4 mg/kg | 2068.9 ± 357.7 |
| B16/BCMA Tumor REGN5458 (BCMA × CD3-G) - 0.4 mg/kg | 47.1 ± 17.0 |
| B16/BCMA Tumor REGN5458 (BCMA × CD3-G) - 0.04 mg/kg | 127.2 ± 63.9 |
| MC38/BCMA Tumor mAb17664D (CD3 Binding Control-G) - 0.4 mg/kg | 1432.5 ± 231.6 |
| MC38/BCMA Tumor REGN5458 (BCMA × CD3-G) - 0.4 mg/kg | 7.5 ± 7.5 |

TABLE 24-continued

Average Tumor Size at Various Time Points

Antibody Treatment

| | |
|---|---|
| MC38/BCMA Tumor REGN5458 (BCMA × CD3-G) - 0.04 mg/kg | 641.5 ± 309.8 |

Example 17: Epitope Mapping of REGN5458 Binding to BCMA by Hydrogen Deuterium Exchange H/D exchange epitope mapping with mass spectrometry (HDX-MS) was performed to determine the amino acid residues of BCMA (recombinant human BCMA, amino acid sequence of SEQ ID NO: 115) interacting with REGN5458 (BCMA×CD3 bispecific antibody). A general description of the H/D exchange method is set forth in e.g., Ehring (1999) *Analytical Biochemistry* 267(2):252-259; and Engen and Smith (2001) *Anal. Chem.* 73:256A-265A.

The HDX-MS experiments were performed on an integrated HDX/MS platform, consisting of a Leaptec HDX PAL system for the deuterium labeling and quenching, a Waters Acquity M-Class (Auxiliary solvent manager) for the sample digestion and loading, a Waters Acquity M-Class (µBinary solvent manager) for the analytical gradient, and Thermo Q Exactive HF mass spectrometer for peptide mass measurement.

The labeling solution was prepared as PBS buffer in D$_2$O at pD 7.0 (10 mM phosphate buffer, 140 mM NaCl, and 3 mM KCl, equivalent to pH 7.4 at 25° C.). For deuterium labeling, 10 µL of hBCMA.hFc (REGN2746, 54.5 pM; SEQ ID NO: 120 or hBCMA.hFc premixed with REGN5458 in 1:2 molar ratio (Ag-Ab complex) was incubated at 20° C. with 90 µL D$_2$O labeling solution for various time-points in duplicates (e.g., Undeuterated control=0 second; deuterium-labeled for 5 minutes and 10 minutes). The deuteration reaction was quenched by adding 100 µL of pre-chilled quench buffer (0.5 M TCEP-HCl, 8 M urea and 1% formic acid) to each sample for a 5-minute incubation at 20° C. The quenched sample was then injected into a Waters HDX Manager for online pepsin/protease XIII digestion. The digested peptides were separated by a C8 column (1.0 mm×50 mm, NovaBioassays) with a 13-minute gradient from 10%-32% B (mobile phase A: 0.5% formic acid in water, mobile phase B: 0.1% formic acid in acetonitrile). The eluted peptides were analyzed by Q Exactive HF mass spectrometry in LC-MS/MS or LC-MS mode.

The LC-MS/MS data of undeuterated BCMA sample were searched against a database including BCMA and its randomized sequence using Byonic search engine (Protein Metrics). The search parameters (in ELN) were set as default using non-specific enzymatic digestion and human glycosylation as common variable modification. The list of identified peptides was then imported into the HDX Workbench software (version 3.3) to calculate the deuterium uptake of each peptide detected by LC-MS from all deuterated samples. For a given peptide, the centroid mass (intensity-weighted average mass) at each time point was used to calculate the deuterium uptake (D) and percentage of deuterium uptake (% D):

Deuterium Uptake (D−uptake) =

Average Mass (deuterated) − Average Mass (undeuterated)

-continued

Percentage of deuterium uptake (% D) =

$$\frac{D\text{-uptake for peptide at each time point} \times 100\%}{\text{Maximum } D\text{-uptake of the peptide (defined in } ELN)}$$

A total of 8 peptides from hBCMA.hFc were identified from both hBCMA.hFc alone and hBCMA.hFc in complex with REGN5458 samples, representing 100% sequence coverage of hBCMA. The averaged standard deviation (SD) of all peptides was evaluated to be 1.4% (detailed calculations were defined in ELN and Pascal, B D et al (2012) *Journal of the American Society for Mass Spectrometry* 23(9):1512-1521). Therefore, any peptide which exhibited a differential percent D-uptake values above 4.2% (3-fold of the averaged SD) was defined as significantly protected. For hBCMA.hFc, peptides corresponding to amino acids 1-43 of SEQ ID NO: 106 (MLQMAGQCSQNEYFDSLLHACI-PCQLRCSSNTPPLTCQRYCNA; SEQ ID NO: 121) were significantly protected by REGN5458. Protection of these residues by REGN5458 was confirmed using hBCMA.mmH (REGN2744, amino acid sequence of SEQ ID NO: 106).

cleavage resulting in increased levels of BCMA on the cell surface. Tables 26-29 report the fold increase in the median fluorescence intensity (MFI) of BCMA on cells incubated overnight in anti-BCMA antibodies or DAPT compared to cells incubated in media only. We observed that overnight incubation with DAPT increased BCMA levels detected by anti-BCMA antibodies (BCMA×CD3 bispecific R5458, the parental BCMA antibody mAb15281, and other in house BCMA antibodies) on H929, Molp8, U266 and MM.1S, 2.3-4 fold, 2.4-8.6 fold, 5.3-9.0 fold, and 11.9 fold, respectively.

Of note, we also observed that overnight incubation of MM cell lines with 66.7 or 667 nM REGN5458 or the parental bivalent anti-BCMA antibody mAb21581 similarly resulted in increased levels of surface BCMA detected by FACS, suggesting that binding of anti-BCMA antibodies prevents cleavage of BCMA by gamma-secretase. Antibody induced increases in surface BCMA differed by cell line, with greater fold increases on Molp8 and MM1S cells compared to H929 or U266. The phenomenon was not limited to REGN5458, as it was also observed with other in house BCMA antibodies.

TABLE 25

Selected BCMA.hFc peptides with significant protection upon binding to REGN5458

| | 5 min | | | 10 min | | | |
|---|---|---|---|---|---|---|---|
| BCMA Residues | REGN2746 Centroid MH+ | REGN2746 + REGN5458 Centroid MH+ | ΔD | REGN2746 Centroid MH+ | REGN2746 + REGN5458 Centroid MH+ | ΔD | –hFc Δ% D |
| 1-28 | 3217.16 | 3212.39 | −4.77 | 3218.05 | 3212.62 | −5.43 | −25.2 |
| 4-26 | 2582.03 | 2577.26 | −4.77 | 2582.71 | 2577.45 | −5.26 | −31 |
| 27-43 | 1921.75 | 1920.69 | −1.06 | 1922.1 | 1920.83 | −1.27 | −11.1 |

Example 18: FACS Binding Assay of BCMA×CD3 Bispecific Antibodies and Additional BCMA Antibodies on Multiple Myeloma Cell Lines After Overnight Incubation with Anti-BCMA Antibodies Flow cytometric analysis was utilized to determine the impact of overnight incubation of multiple myeloma cell lines with anti-BCMA antibodies on the level of surface BCMA. MM cell lines (H929, Molp8, U266 and MM1.S) were washed two times and cultured at 37° C. in R10 media (RPMI+10% FBS+pen/strep/glut) containing 66.7 or 667 nM anti-BCMA antibodies, DAPT (a gamma-secretase inhibitor) or media only. After 18 hours, wells were washed with cold FACS wash (PBS+1% filtered FBS) and resuspended in 667 nM of the same anti-BCMA antibody in cold stain buffer (Miltenyi 130-091-221) for 30 minutes on ice. After incubation, the cells were washed twice with cold FACS wash (PBS+1% filtered FBS) and bound antibody was detected by incubating with the appropriate anti-human secondary antibody (anti-hIgG or anti-HIS) on ice for an additional 30-45 minutes. After incubation, cells were washed, re-suspended in 200 μL cold PBS containing 1% filtered FBS and analyzed by flow cytometry on a BD FACS Canto II. Fold increase in staining was calculated by dividing the MFI of stained cells previously incubated overnight in BCMA abs or DAPT by the MFI of stained cells that were incubated overnight in media only.

BCMA is rapidly cleaved from the surface of cells by the enzyme gamma-secretase. Overnight incubation with the gamma-secretase inhibitors, such as DAPT, prevents BCMA

TABLE 26

MFI fold change over cells incubated in media only (NCI-H929)

| | | 67 nM | | 667 nM | | DAPT | |
|---|---|---|---|---|---|---|---|
| | NCI-H929 | Average | n | Average | n | Average | n |
| mAb21581 | aBCMA (parent to R5458) | 1.2 | 5 | 1.4 | 3 | 3.5 | 6 |
| REGN5458 | BCMA × CD3 | 2.0 | 3 | 3.0 | 1 | 4.0 | 3 |
| mAb16749 | aBCMA | 1.0 | 2 | 0.8 | 1 | 2.3 | 3 |
| mAb16711 | aBCMA | 2.8 | 2 | 2.1 | 1 | 3.8 | 3 |
| mAb16747 | aBCMA | 1.8 | 2 | 2.1 | 1 | 3.9 | 3 |
| REGN960 | scFv IsoC | 1.0 | 2 | 1.1 | 1 | 1.1 | 3 |
| mAb11810 | IgG1 IsoC | 1.0 | 2 | 1.0 | 1 | 1.1 | 3 |
| mAb11810 | IgG4s IsoC | 1.3 | 2 | 1.0 | 1 | 1.1 | 3 |

TABLE 27

MFI fold change over cells incubated in media only (Molp8)

| | | 67 nM | | 667 nM | | DAPT | |
|---|---|---|---|---|---|---|---|
| | Molp8 | Average | n | Average | n | Average | n |
| mAb21581 | aBCMA (parent to R5458) | 2.3 | 5 | 3.7 | 3 | 6.3 | 6 |
| REGN5458 | BCMA × CD3 | 2.3 | 3 | 4.5 | 1 | 8.6 | 3 |

TABLE 27-continued

MFI fold change over cells incubated in media only (Molp8)

| Molp8 | | 67 nM | | 667 nM | | DAPT | |
|---|---|---|---|---|---|---|---|
| | | Average | n | Average | n | Average | n |
| mAb16749 | aBCMA | 1.1 | 2 | 3.4 | 1 | 4.0 | 3 |
| mAb16711 | aBCMA | 3.5 | 2 | 3.0 | 1 | 5.1 | 3 |
| mAb16747 | aBCMA | 2.2 | 2 | 0.6 | 1 | 6.2 | 3 |
| REGN960 | scFv IsoC | 1.1 | 2 | 1.0 | 1 | 1.0 | 3 |
| mAb11810 | IgG1 IsoC | 1.0 | 2 | 1.3 | 1 | 1.1 | 3 |
| mAb11810 | IgG4s IsoC | 0.9 | 2 | 1.2 | 1 | 1.0 | 3 |

TABLE 28

MFI fold change over cells incubated in media only (U266)

| U266 | | 67 nM | | 667 nM | | DAPT | |
|---|---|---|---|---|---|---|---|
| | | Average | n | Average | n | Average | n |
| mAb21581 | aBCMA (parent to R5458) | 1.8 | 2 | 2.3 | 1 | 6.7 | 6 |
| REGN5458 | BCMA × CD3 | 1.4 | 2 | 2.3 | 1 | 9.0 | 3 |
| mAb16749 | aBCMA | 1.3 | 2 | 1.2 | 1 | 5.3 | 3 |
| mAb16711 | aBCMA | 2.2 | 2 | 2.2 | 1 | 7.2 | 3 |
| mAb16747 | aBCMA | 1.5 | 2 | 1.7 | 1 | 8.3 | 3 |
| REGN960 | scFv IsoC | 1.0 | 2 | 1.0 | 1 | 1.0 | 3 |
| mAb11810 | IgG1 IsoC | 1.0 | 2 | 1.1 | 1 | 1.1 | 3 |
| mAb11810 | IgG4s IsoC | 1.1 | 2 | 1.1 | 1 | 1.4 | 3 |

TABLE 29

MFI fold change over cells incubated in media only (MM1S)

| MM1S | | 67 nM | | 667 nM | | DAPT | |
|---|---|---|---|---|---|---|---|
| | | Average | n | Average | n | Average | n |
| mAb21581 | aBCMA (parent to R5458) | 7.3 | 2 | 7.0 | 2 | 11.9 | 2 |

Example 19: Autologous T Cell-Mediated Killing of Human and Cynomolgus Monkey Plasma Cells in the Presence of BCMA×CD3 Bispecific Antibodies The specific killing of enriched CD138$^+$ human or cynomolgus monkey plasma cells by unstimulated autologous T cells was assessed by flow cytometry. Human or cynomolgus bone marrow aspirates and blood were provided within 24 hours of harvest. CD138$^+$ plasma cells were enriched from bone marrow by positive selection using the EasySep™ Human CD138$^+$ Positive Selection kit according to the manufacturer's instructions. PBMC from whole blood were isolated by density separation. PBMC were labeled with 1 µM of Vybrant™ CFDA-SE fluorescent tracking dye. After labeling, 1×10$^4$ enriched CD138$^+$ plasma cells were plated in round-bottom 96 well plates at an E:T ratio of 10:1 with Vybrant™ CFDA-SE labeled PBMC and serial dilutions of REGN5458, CD3-binding control bsAb, or BCMA-binding control mAb for 72 hours at 37° C. in complete media. At the end of the culture, surviving CD138$^+$ plasma cells were analyzed by flow cytometry, utilizing fixable LIVE/DEAD dye and plasma cell specific cell surface markers. Percent viability was normalized to control condition (plasma cells in the presence of PBMC only). T cell activation was assessed by flow cytometry. Activation is reported as the percentage of CD2$^+$/CD4$^+$ or CD2$^+$/CD8$^+$/CD16$^-$ T cells expressing CD25. Percent T cell activation was normalized to control condition (plasma cells in the presence of PBMC only).

In vitro studies evaluated the effect of REGN5458 or negative controls (BCMA-binding control mAb or CD3-binding control bsAb) on primary human and cynomolgus monkey T cell activation and cytotoxicity of autologous plasma cells. The EC$_{50}$ values for cytotoxicity and percent T cell activation for each donor are summarized in Table 30.

REGN5458 mediated cytotoxicity of primary human plasma cells from donors 1 and 2 in the presence autologous T cells in a concentration-dependent manner with EC$_{50}$ values of 42.8 pM and 191 pM, respectively, and resulted in a maximum percent cytotoxicity of 91% and 89%, respectively. In parallel, REGN5458 mediated T cell activation in the presence of human plasma cells from donors 1 and 2 in a concentration-dependent manner with EC$_{50}$ values of 214 pM and 860 pM for CD8$^+$ T cell activation, respectively, and maximum percent CD8$^+$ T cell activation of 2% and 36%, respectively. Cytotoxicity of plasma cells in both donors and increased CD8$^+$ T cell activation in donor 2 only was observed at nanomolar concentrations of CD3-binding control. No effect on cytotoxicity or T cell activation was observed with BCMA-binding control at any of the concentrations tested in either donor.

REGN5458 mediated cytotoxicity of primary cynomolgus plasma cells in both donors in a concentration-dependent manner; an EC$_{50}$ of 1.31 nM was calculated for donor 1, however an EC50 could not be determined for donor 2. In both donors, REGN5458 treatment resulted in increased cytotoxicity of plasma cells (maximum percent cytotoxicity of 94% and 91% for donors 1 and 2, respectively). In parallel, REGN5458 mediated T cell activation in the presence of cynomolgus monkey plasma cells from donors 1 and 2 in a concentration-dependent manner with EC$_{50}$ values of 28.1 nM and 18.1 nM for CD4$^+$ T cell activation and 22.4 nM and 76.7 nM for CD8$^+$ T cell activation, respectively. The resulting maximum percent T cell activation was 9% and 16% for CD4$^+$ T cells and 12% and 17% CD8$^+$ T cells for donors 1 and 2, respectively.

No target cell killing was observed with BCMA-binding control at any concentration tested in either of the cell lines evaluated. Some target cell killing and T cell activation in the presence of plasma cells from donor 2 was observed with CD3-binding control at nanomolar concentrations.

TABLE 30

EC$_{50}$ Values for Cytotoxicity and Percent T Cell Activation for Each Donor

| Cell Lines | | Cytotoxic Kill | | T Cell Activation (% CD25 Upregulation) | | | |
|---|---|---|---|---|---|---|---|
| | | | | CD4$^+$ T cells | | CD8$^+$ T cells | |
| Effector Cells | Target Cells | EC$_{50}$ (M) | Max % Cytotoxicity | EC$_{50}$ (M) | % Activation | EC$_{50}$ (M) | % Activation |
| Primary Human T Cells$^a$ | Human Donor 1 Plasma Cells | 4.28 × 10$^{-11}$ | 91 | NR | NR | 2.14 × 10$^{-10}$ | 2 |
| | Human Donor 2 Plasma Cells | 1.91 × 10$^{-10}$ | 89 | NR | NR | 8.60 × 10$^{-10}$ | 36 |
| Primary Cynomolgus Monkey T Cells$^a$ | Cynomolgus Monkey Donor 1 Plasma Cells | 1.31 × 10$^{-9}$ | 94 | 2.81 × 10$^{-8}$ | 9 | 2.24 × 10$^{-8}$ | 12 |
| | Cynomolgus Monkey Donor 2 Plasma Cells | ND | 91 | ~1.81 × 10$^{-8}$ | 16 | 7.67 × 10$^{-8}$ | 17 |

$^a$Autologous plasma cells were tested for each donor.

Example 20: Anti-BCMA×Anti-CD3 Bispecific Antibodies Act Synergistically with Anti-PD-1 Antibodies to Enhance Anti-Tumor Efficacy In Vivo To determine whether BCMA×CD3 bispecific antibodies (Abs) synergize with PD-1 blockade to provide superior anti-tumor efficacy in vivo, a syngenic tumor study was performed in mice expressing human CD3. The results demonstrate that combining REGN5458 plus PD-1 blockade provides superior anti-tumor efficacy than either REGN5458 or PD-1 blockade alone.

Implantation and measurement of syngenic tumors: C57BL/6 mice that express human CD3deg in place of murine CD3deg (CD3-humanized mice) were subcutaneously implanted with 1×10$^6$ MC38 colon carcinoma cells that have been engineered to express full-length human BCMA (MC38/BCMA). The tumors were allowed to establish for 3 days, at which time the mice (n=6 or 7 per group) were administered a CD3-binding control bispecific Ab (G; H4sH17664D) at a dose of 0.4 mg/kg or a BCMA×CD3 (G; REGN5458) bispecific Ab at doses of either 0.04 mg/kg or 0.24 mg/kg, along with either a surrogate anti-mouse PD-1 antibody (Clone RPM1-14) at 4 mg/kg or an isotype control Ab (Clone 2A3) at 4 mg/kg. The specific treatment groups are shown in Table 31, below.

TABLE 31

Treatment Groups

| Group | Bispecific Treatment | Antibody | n |
|---|---|---|---|
| 1 | H4SH17664D (0.24 mg/kg) | Isotype (4 mg/kg) | 7 |
| 2 | H4SH17664D (0.24 mg/kg) | RPM1-14 (4 mg/kg) | 7 |
| 3 | REGN5458 (0.04 mg/kg) | Isotype (4 mg/kg) | 7 |
| 4 | REGN5458 (0.04 mg/kg) | RPM1-14 (4 mg/kg) | 7 |
| 5 | REGN5458 (0.24 mg/kg) | Isotype (4 mg/kg) | 6 |
| 6 | REGN5458 (0.24 mg/kg) | RPM1-14 (4 mg/kg) | 6 |

The mice were administered these Abs twice more on days 7 and 11 for a total of three doses, and tumor growth was assessed throughout the experiment.

Calculation of syngenic tumor growth and inhibition: In order to determine tumor volume by external caliper, the greatest longitudinal diameter (length in mm) and the greatest transverse diameter (width in mm) were determined. Tumor volumes based on caliper measurements were calculated by the formula: Volume (mm$^3$)=(length×width$^2$)/2.

The results demonstrate that combining REGN5458 plus PD-1 blockade provides superior anti-tumor efficacy than either REGN5458 or PD-1 blockade alone. In particular, the results demonstrate that at day 24 (the last day for which data was collected for all treatment groups) the combination of BCMA×CD3 bispecific antibody and anti-PD-1 antibody produced a statistically significant synergistic therapeutic effect in the inhibition of tumor growth (Table 32, BCMA× CD3 at 0.04 mg/kg and anti-PD-1 at 4 mg/kg). Using a 2-way ANOVA test at day 24, p<0.0001 between (i) REGN5458 (0.04 mg/kg)+Isotype and the combination of REGN5458 (0.04 mg/kg)+anti-PD-1 antibody (Group 3 vs. Group 4), (ii) REGN5458 (0.24 mg/kg)+Isotype and the combination of REGN5458 (0.24 mg/kg)+anti-PD-1 antibody (Group 5 vs. Group 6), (iii) anti-PD-1 and the combination of REGN5458 (0.04 mg/kg)+anti-PD-1 antibody (Group 2 vs. Group 6). Using a 2-way ANOVA test at day 24, p=0.0005 between anti-PD-1 and the combination of REGN5458 (0.04 mg/kg)+anti-PD-1 antibody (Group 2 vs. Group 4). Increasing the dose of BCMA×CD3 bispecific antibody (0.24 mg/kg) in combination with PD-1 blockade resulted in tumor inhibition comparable to the lower bispecific antibody dose plus PD-1 blockade in this experiment. The demonstrated synergy with the lower dose bispecific antibody is advantageous because the use of a lower dose reduces the risk of any adverse side effects. Similarly, the combination of BCMA×CD3 bispecific antibody and anti-PD-1 antibody showed a synergistic therapeutic effect at both doses of bispecific antibody (0.04 mg/kg and 0.24 mg/kg) in the number of tumor-free mice at the end of the experiment (day 28), as shown in Table 33.

TABLE 32

Average Tumor Size at Various Time Points

| Antibody Treatment | Average Tumor Size (mm3) ± SEM on Day 3 |
|---|---|
| CD3-binding control H4SH17664D (0.24 mg/kg) + Isotype (4 mg/kg) | 16.30 ± 1.50<br>n = 7 |
| CD3-binding control H4SH17664D (0.24 mg/kg) + PD-1-blocking RPM1-14 (4 mg/kg) | 14.34 ± 1.17<br>n = 7 |
| BCMA × CD3 REGN5458 (0.04 mg/kg) + Isotype (4 mg/kg) | 15.62 ± 1.61<br>n = 7 |
| BCMA × CD3 REGN5458 (0.04 mg/kg) + PD-1-blocking RPM1-14 (4 mg/kg) | 19.20 ± 2.94<br>n = 7 |

TABLE 32-continued

Average Tumor Size at Various Time Points

| Antibody Treatment | |
|---|---|
| BCMA × CD3 REGN5458 (0.24 mg/kg) + Isotype (4 mg/kg) | 13.13 ± 3.12<br>n = 6 |
| BCMA × CD3 REGN5458 (0.24 mg/kg) + PD-1-blocking RPM1-14 (4 mg/kg) | 20.41 ± 3.15<br>n = 6 |
| *Average Tumor Size (mm3) ± SEM on Day 7* | |
| CD3-binding control H4SH17664D (0.24 mg/kg) + Isotype (4 mg/kg) | 55.78 ± 6.61<br>n = 7 |
| CD3-binding control H4SH17664D (0.24 mg/kg) + PD-1-blocking RPM1-14 (4 mg/kg) | 43.59 ± 8.32<br>n = 7 |
| BCMA × CD3 REGN5458 (0.04 mg/kg) + Isotype (4 mg/kg) | 37.98 ± 3.93<br>n = 7 |
| BCMA × CD3 REGN5458 (0.04 mg/kg) + PD-1-blocking RPM1-14 (4 mg/kg) | 30.30 ± 6.47<br>n = 7 |
| BCMA × CD3 REGN5458 (0.24 mg/kg) + Isotype (4 mg/kg) | 29.27 ± 5.00<br>n = 6 |
| BCMA × CD3 REGN5458 (0.24 mg/kg) + PD-1-blocking RPM1-14 (4 mg/kg) | 29.18 ± 3.65<br>n = 6 |
| *Average Tumor Size (mm3) ± SEM on Day 11* | |
| CD3-binding control H4SH17664D (0.24 mg/kg) + Isotype (4 mg/kg) | 145.74 ± 21.37<br>n = 7 |
| CD3-binding control H4SH17664D (0.24 mg/kg) + PD-1-blocking RPM1-14 (4 mg/kg) | 45.33 ± 11.46<br>n = 7 |
| BCMA × CD3 REGN5458 (0.04 mg/kg) + Isotype (4 mg/kg) | 112.53 ± 17.39<br>n = 7 |
| BCMA × CD3 REGN5458 (0.04 mg/kg) + PD-1-blocking RPM1-14 (4 mg/kg) | 8.81 ± 0.88<br>n = 7 |
| BCMA × CD3 REGN5458 (0.24 mg/kg) + Isotype (4 mg/kg) | 36.63 ± 14.89<br>n = 6 |
| BCMA × CD3 REGN5458 (0.24 mg/kg) + PD-1-blocking RPM1-14 (4 mg/kg) | 12.99 ± 4.35<br>n = 6 |
| *Average Tumor Size (mm3) ± SEM on Day 14* | |
| CD3-binding control H4SH17664D (0.24 mg/kg) + Isotype (4 mg/kg) | 414.28 ± 46.72<br>n = 7 |
| CD3-binding control H4SH17664D (0.24 mg/kg) + PD-1-blocking RPM1-14 (4 mg/kg) | 49.50 ± 17.02<br>n = 7 |
| BCMA × CD3 REGN5458 (0.04 mg/kg) + Isotype (4 mg/kg) | 438.16 ± 59.56<br>n = 7 |
| BCMA × CD3 REGN5458 (0.04 mg/kg) + PD-1-blocking RPM1-14 (4 mg/kg) | 6.86 ± 3.90<br>n = 7 |
| BCMA × CD3 REGN5458 (0.24 mg/kg) + Isotype (4 mg/kg) | 224.33 ± 47.04<br>n = 6 |
| BCMA × CD3 REGN5458 (0.24 mg/kg) + PD-1-blocking RPM1-14 (4 mg/kg) | 22.75 ± 17.62<br>n = 6 |
| *Average Tumor Size (mm3) ± SEM on Day 18* | |
| CD3-binding control H4SH17664D (0.24 mg/kg) + Isotype (4 mg/kg) | 1035.43 ± 123.41<br>n = 6 |
| CD3-binding control H4SH17664D (0.24 mg/kg) + PD-1-blocking RPM1-14 (4 mg/kg) | 100.83 ± 41.62<br>n = 7 |
| BCMA × CD3 REGN5458 (0.04 mg/kg) + Isotype (4 mg/kg) | 1040.12 ± 61.95<br>n = 7 |
| BCMA × CD3 REGN5458 (0.04 mg/kg) + PD-1-blocking RPM1-14 (4 mg/kg) | 7.81 ± 7.81<br>n = 7 |
| BCMA × CD3 REGN5458 (0.24 mg/kg) + Isotype (4 mg/kg) | 515.15 ± 115.38<br>n = 6 |
| BCMA × CD3 REGN5458 (0.24 mg/kg) + PD-1-blocking RPM1-14 (4 mg/kg) | 57.79 ± 43.62<br>n = 6 |
| *Average Tumor Size (mm3) ± SEM on Day 21* | |
| CD3-binding control H4SH17664D (0.24 mg/kg) + Isotype (4 mg/kg) | 1834.87 ± 639.56<br>n = 2 |
| CD3-binding control H4SH17664D (0.24 mg/kg) + PD-1-blocking RPM1-14 (4 mg/kg) | 208.29 ± 91.80<br>n = 7 |
| BCMA × CD3 REGN5458 (0.04 mg/kg) + Isotype (4 mg/kg) | 2133.12 ± 129.26<br>n = 6 |
| BCMA × CD3 REGN5458 (0.04 mg/kg) + PD-1-blocking RPM1-14 (4 mg/kg) | 21.13 ± 21.13<br>n = 7 |
| BCMA × CD3 REGN5458 (0.24 mg/kg) + Isotype (4 mg/kg) | 1225.47 ± 289.39<br>n = 6 |
| BCMA × CD3 REGN5458 (0.24 mg/kg) + PD-1-blocking RPM1-14 (4 mg/kg) | 113.69 ± 85.39<br>n = 6 |
| *Average Tumor Size (mm3) ± SEM on Day 24* | |
| CD3-binding control H4SH17664D (0.24 mg/kg) + Isotype (4 mg/kg) | 2358.81 ± 0.00<br>n = 1 |
| CD3-binding control H4SH17664D (0.24 mg/kg) + PD-1-blocking RPM1-14 (4 mg/kg) | 534.03 ± 205.49<br>n = 7 |
| BCMA × CD3 REGN5458 (0.04 mg/kg) + Isotype (4 mg/kg) | 3648.37 ± 536.71<br>n = 3 |
| BCMA × CD3 REGN5458 (0.04 mg/kg) + PD-1-blocking RPM1-14 (4 mg/kg) | 53.52 ± 53.52<br>n = 7 |
| BCMA × CD3 REGN5458 (0.24 mg/kg) + Isotype (4 mg/kg) | 1493.26 ± 973.01<br>n = 2 |
| BCMA × CD3 REGN5458 (0.24 mg/kg) + PD-1-blocking RPM1-14 (4 mg/kg) | 54.29 ± 54.29<br>n = 5 |
| *Average Tumor Size (mm3) ± SEM on Day 28* | |
| CD3-binding control H4SH17664D (0.24 mg/kg) + Isotype (4 mg/kg) | All Animals Euthanized<br>n = 0 |
| CD3-binding control H4SH17664D (0.24 mg/kg) + PD-1-blocking RPM1-14 (4 mg/kg) | 1196.57 ± 467.34<br>n = 7 |
| BCMA × CD3 REGN5458 (0.04 mg/kg) + Isotype (4 mg/kg) | All Animals Euthanized<br>n = 0 |
| BCMA × CD3 REGN5458 (0.04 mg/kg) + PD-1-blocking RPM1-14 (4 mg/kg) | 141.68 ± 141.68<br>n = 7 |
| BCMA × CD3 REGN5458 (0.24 mg/kg) + Isotype (4 mg/kg) | 1371.17 ± 0.00<br>n = 1 |
| BCMA × CD3 REGN5458 (0.24 mg/kg) + PD-1-blocking RPM1-14 (4 mg/kg) | 104.44 ± 104.44<br>n = 5 |

TABLE 33

Tumor-Free Mice at End of Experiment

| Antibody Treatment | Number of Mice Tumor-Free at End of Experiment (Day 28) |
|---|---|
| CD3-binding control H4SH17664D (0.24 mg/kg) + Isotype (4 mg/kg) | 0 of 7 |
| CD3-binding control H4SH17664D (0.24 mg/kg) + PD-1-blocking RPM1-14 (4 mg/kg) | 2 of 7 |
| BCMA × CD3 REGN5458 (0.04 mg/kg) + Isotype (4 mg/kg) | 0 of 7 |
| BCMA × CD3 REGN5458 (0.04 mg/kg) + PD-1-blocking RPM1-14 (4 mg/kg) | 6 of 7 |
| BCMA × CD3 REGN5458 (0.24 mg/kg) + Isotype (4 mg/kg) | 0 of 6 |
| BCMA × CD3 REGN5458 (0.24 mg/kg) + PD-1-blocking RPM1-14 (4 mg/kg) | 4 of 6 |

Example 21: Anti-BCMA×Anti-CD3 Bispecific Antibodies Act Synergistically with Anti-PD-1 Antibodies to Enhance Anti-Tumor Efficacy In Vivo Similar results were obtained in a second experiment, identical to that discussed above in Example 20, except that the number of mice per group=10, and the higher dose of BCMA×CD3 REGN5458 was 0.4 mg/kg. The specific treatment groups for the second experiment are shown in Table 34, below.

TABLE 34

Treatment Groups

| Group | Bispecific Treatment | Antibody | n |
|---|---|---|---|
| 1 | H4SH17664D (0.4 mg/kg) | Isotype (4 mg/kg) | 10 |
| 2 | H4SH17664D (0.4 mg/kg) | RPM1-14 (4 mg/kg) | 10 |
| 3 | REGN5458 (0.04 mg/kg) | Isotype (4 mg/kg) | 10 |
| 4 | REGN5458 (0.04 mg/kg) | RPM1-14 (4 mg/kg) | 10 |
| 5 | REGN5458 (0.4 mg/kg) | Isotype (4 mg/kg) | 10 |
| 6 | REGN5458 (0.4 mg/kg) | RPM1-14 (4 mg/kg) | 10 |

The results demonstrate that combining REGN5458 plus PD-1 blockade provides superior anti-tumor efficacy than either REGN5458 or PD-1 blockade alone. In particular, the results demonstrate that at day 21 (the last day for which data was collected for all treatment groups) the combination of BCMA×CD3 bispecific antibody and anti-PD-1 antibody produced a synergistic therapeutic effect in the inhibition of tumor growth (Table 35, BCMA×CD3 at 0.04 mg/kg and anti-PD-1 at 4 mg/kg). Using a 2-way ANOVA test at day 21, $p<0.0001$ between (i) REGN5458 (0.04 mg/kg)+Isotype and the combination of REGN5458 (0.04 mg/kg)+anti-PD-1 antibody (Group 3 vs. Group 4), (ii) anti-PD-1 and the combination of REGN5458 (0.04 mg/kg)+anti-PD-1 antibody (Group 2 vs. Group 4), (iii) anti-PD-1 and the combination of REGN5458 (0.4 mg/kg)+anti-PD-1 antibody (Group 2 vs. Group 6). As discussed above in Example 20, increasing the dose of BCMA×CD3 bispecific antibody (0.4 mg/kg) in combination with PD-1 blockade resulted in tumor inhibition comparable to the lower bispecific antibody dose combined with PD-1 blockade in this experiment. The demonstrated synergy with the lower dose bispecific antibody is advantageous because the use of a lower dose reduces the risk of any adverse side effects. Similarly, the combination of BCMA×CD3 bispecific antibody and anti-PD-1 antibody showed a synergistic therapeutic effect at both doses of bispecific antibody (0.04 mg/kg and 0.4 mg/kg) in the number of tumor-free mice at the end of the experiment (day 25), as shown in Table 36.

TABLE 35

Average Tumor Size at Various Time Points

| Antibody Treatment | Average Tumor Size (mm3) ± SEM on Day 3 |
|---|---|
| CD3-binding control H4SH17664D (0.4 mg/kg) + Isotype (4 mg/kg) | 9.85 ± 0.61<br>n = 10 |
| CD3-binding control H4SH17664D (0.4 mg/kg) + PD-1-blocking RPM1-14 (4 mg/kg) | 13.44 ± 1.44<br>n = 10 |
| BCMA × CD3 REGN5458 (0.04 mg/kg) + Isotype (4 mg/kg) | 12.41 ± 2.56<br>n = 10 |
| BCMA × CD3 REGN5458 (0.04 mg/kg) + PD-1-blocking RPM1-14 (4 mg/kg) | 9.73 ± 1.25<br>n = 10 |
| BCMA × CD3 REGN5458 (0.4 mg/kg) + Isotype (4 mg/kg) | 11.22 ± 0.68<br>n = 10 |
| BCMA × CD3 REGN5458 (0.4 mg/kg) + PD-1-blocking RPM1-14 (4 mg/kg) | 9.59 ± 1.78<br>n = 10 |

TABLE 35-continued

Average Tumor Size at Various Time Points

| Antibody Treatment | Average Tumor Size (mm3) ± SEM on Day 6 |
|---|---|
| CD3-binding control H4SH17664D (0.4 mg/kg) + Isotype (4 mg/kg) | 40.43 ± 4.07<br>n = 10 |
| CD3-binding control H4SH17664D (0.4 mg/kg) + PD-1-blocking RPM1-14 (4 mg/kg) | 44.52 ± 2.80<br>n = 10 |
| BCMA × CD3 REGN5458 (0.04 mg/kg) + Isotype (4 mg/kg) | 38.79 ± 3.52<br>n = 10 |
| BCMA × CD3 REGN5458 (0.04 mg/kg) + PD-1-blocking RPM1-14 (4 mg/kg) | 36.42 ± 3.51<br>n = 10 |
| BCMA × CD3 REGN5458 (0.4 mg/kg) + Isotype (4 mg/kg) | 16.11 ± 1.27<br>n = 10 |
| BCMA × CD3 REGN5458 (0.4 mg/kg) + PD-1-blocking RPM1-14 (4 mg/kg) | 24.34 ± 1.86<br>n = 10 |

| Antibody Treatment | Average Tumor Size (mm3) ± SEM on Day 10 |
|---|---|
| CD3-binding control H4SH17664D (0.4 mg/kg) + Isotype (4 mg/kg) | 149.41 ± 17.08<br>n = 10 |
| CD3-binding control H4SH17664D (0.4 mg/kg) + PD-1-blocking RPM1-14 (4 mg/kg) | 107.34 ± 13.73<br>n = 10 |
| BCMA × CD3 REGN5458 (0.04 mg/kg) + Isotype (4 mg/kg) | 116.32 ± 19.99<br>n = 10 |
| BCMA × CD3 REGN5458 (0.04 mg/kg) + PD-1-blocking RPM1-14 (4 mg/kg) | 23.48 ± 3.24<br>n = 10 |
| BCMA × CD3 REGN5458 (0.4 mg/kg) + Isotype (4 mg/kg) | 24.27 ± 6.74<br>n = 10 |
| BCMA × CD3 REGN5458 (0.4 mg/kg) + PD-1-blocking RPM1-14 (4 mg/kg) | 3.60 ± 1.92<br>n = 10 |

| Antibody Treatment | Average Tumor Size (mm3) ± SEM on Day 13 |
|---|---|
| CD3-binding control H4SH17664D (0.4 mg/kg) + Isotype (4 mg/kg) | 386.55 ± 48.49<br>n = 10 |
| CD3-binding control H4SH17664D (0.4 mg/kg) + PD-1-blocking RPM1-14 (4 mg/kg) | 186.87 ± 41.06<br>n = 10 |
| BCMA × CD3 REGN5458 (0.04 mg/kg) + Isotype (4 mg/kg) | 319.91 ± 53.05<br>n = 10 |
| BCMA × CD3 REGN5458 (0.04 mg/kg) + PD-1-blocking RPM1-14 (4 mg/kg) | 10.60 ± 2.34<br>n = 10 |
| BCMA × CD3 REGN5458 (0.4 mg/kg) + Isotype (4 mg/kg) | 50.93 ± 20.00<br>n = 10 |
| BCMA × CD3 REGN5458 (0.4 mg/kg) + PD-1-blocking RPM1-14 (4 mg/kg) | 0.74 ± 0.74<br>n = 10 |

| Antibody Treatment | Average Tumor Size (mm3) ± SEM on Day 18 |
|---|---|
| CD3-binding control H4SH17664D (0.4 mg/kg) + Isotype (4 mg/kg) | 1809.29 ± 242.64<br>n = 9 |
| CD3-binding control H4SH17664D (0.4 mg/kg) + PD-1-blocking RPM1-14 (4 mg/kg) | 688.52 ± 152.20<br>n = 10 |
| BCMA × CD3 REGN5458 (0.04 mg/kg) + Isotype (4 mg/kg) | 1314.27 ± 211.22<br>n = 10 |
| BCMA × CD3 REGN5458 (0.04 mg/kg) + PD-1-blocking RPM1-14 (4 mg/kg) | 6.28 ± 4.55<br>n = 10 |
| BCMA × CD3 REGN5458 (0.4 mg/kg) + Isotype (4 mg/kg) | 248.51 ± 107.21<br>n = 10 |
| BCMA × CD3 REGN5458 (0.4 mg/kg) + PD-1-blocking RPM1-14 (4 mg/kg) | 3.93 ± 2.67<br>n = 10 |

| Antibody Treatment | Average Tumor Size (mm3) ± SEM on Day 21 |
|---|---|
| CD3-binding control H4SH17664D (0.4 mg/kg) + Isotype (4 mg/kg) | 3094.87 ± 482.38<br>n = 8 |
| CD3-binding control H4SH17664D (0.4 mg/kg) + PD-1-blocking RPM1-14 (4 mg/kg) | 1425.22 ± 338.49<br>n = 10 |
| BCMA × CD3 REGN5458 (0.04 mg/kg) + Isotype (4 mg/kg) | 2446.35 ± 395.48<br>n = 10 |

TABLE 35-continued

Average Tumor Size at Various Time Points

| Antibody Treatment | |
|---|---|
| BCMA × CD3 REGN5458 (0.04 mg/kg) + PD-1-blocking RPM1-14 (4 mg/kg) | 15.03 ± 10.35<br>n = 10 |
| BCMA × CD3 REGN5458 (0.4 mg/kg) + Isotype (4 mg/kg) | 453.43 ± 174.75<br>n = 10 |
| BCMA × CD3 REGN5458 (0.4 mg/kg) + PD-1-blocking RPM1-14 (4 mg/kg) | 9.34 ± 7.59<br>n = 10 |

| | Average Tumor Size (mm3) ± SEM on Day 25 |
|---|---|
| CD3-binding control H4SH17664D (0.4 mg/kg) + Isotype (4 mg/kg) | Animals Euthanized<br>n = 0 |
| CD3-binding control H4SH17664D (0.4 mg/kg) + PD-1-blocking RPM1-14 (4 mg/kg) | 1918.27 ± 571.19<br>n = 6 |
| BCMA × CD3 REGN5458 (0.04 mg/kg) + Isotype (4 mg/kg) | 2411.64 ± 451.96<br>n = 3 |
| BCMA × CD3 REGN5458 (0.04 mg/kg) + PD-1-blocking RPM1-14 (4 mg/kg) | 38.96 ± 21.47<br>n = 10 |
| BCMA × CD3 REGN5458 (0.4 mg/kg) + Isotype (4 mg/kg) | 661.70 ± 331.60<br>n = 8 |
| BCMA × CD3 REGN5458 (0.4 mg/kg) + PD-1-blocking RPM1-14 (4 mg/kg) | 32.02 ± 24.67<br>n = 10 |

TABLE 36

Tumor-Free Mice at End of Experiment

| Antibody Treatment | Number of Mice Tumor-Free at End of Experiment (Day 25) |
|---|---|
| CD3-binding control H4SH17664D (0.4 mg/kg) + Isotype (4 mg/kg) | 0 of 10 |
| CD3-binding control H4SH17664D (0.4 mg/kg) + PD-1-blocking RPM1-14 (4 mg/kg) | 1 of 10 |
| BCMA × CD3 REGN5458 (0.04 mg/kg) + Isotype (4 mg/kg) | 0 of 10 |
| BCMA × CD3 REGN5458 (0.04 mg/kg) + PD-1-blocking RPM1-14 (4 mg/kg) | 7 of 10 |
| BCMA × CD3 REGN5458 (0.4 mg/kg) + Isotype (4 mg/kg) | 2 of 10 |
| BCMA × CD3 REGN5458 (0.4 mg/kg) + PD-1-blocking RPM1-14 (4 mg/kg) | 8 of 10 |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A group of nucleic acid molecules encoding a bispecific antigen-binding molecule that binds human B cell maturation antigen (BCMA) and human CD3, wherein the group of nucleic acid molecules comprises:
   (a) a first nucleic acid molecule encoding a heavy chain variable region (HCVR) comprising the amino acid sequence of SEQ ID NO: 66, wherein the first nucleic acid molecule comprises the nucleotide sequence of SEQ ID NO: 65;
   (b) a second nucleic acid molecule encoding a HCVR comprising the amino acid sequence of SEQ ID NO: 90, wherein the second nucleic acid molecule comprises the nucleotide sequence of SEQ ID NO: 89; and
   (c) a third nucleic acid molecule encoding a common light chain variable region (LCVR) comprising the amino acid sequence of SEQ ID NO: 82, wherein the third nucleic acid molecule comprises the nucleotide sequence of SEQ ID NO: 81.

2. The group of nucleic acid molecules of claim 1, wherein the bispecific antigen-binding molecule is a bispecific antibody, the first nucleic acid molecule encodes a first heavy, the second nucleic acid molecule encodes a second heavy chain, and the third nucleic acid molecule encodes a common light chain.

3. The group of nucleic acid molecules of claim 2, wherein the first heavy chain, the second heavy chain, or both the first and second heavy chains comprise a human IgG heavy chain constant region.

4. The group of nucleic acid molecules of claim 3, wherein the first heavy chain, the second heavy chain, or both the first and second heavy chains comprise a human IgG1 heavy chain constant region.

5. The group of nucleic acid molecules of claim 3, wherein the first heavy chain, the second heavy chain, or both the first and second heavy chains comprise a human IgG4 heavy chain constant region.

6. A group of nucleic acid molecules encoding a bispecific antigen-binding molecule that binds human BCMA and human CD3, wherein the group of nucleic acid molecules comprises:
(a) a first nucleic acid molecule encoding a HCVR comprising the amino acid sequence of SEQ ID NO: 66, wherein the first nucleic acid molecule comprises the nucleotide sequence of SEQ ID NO: 65;
(b) a second nucleic acid molecule encoding a HCVR comprising the amino acid sequence of SEQ ID NO: 98, wherein the second nucleic acid molecule comprises the nucleotide sequence of SEQ ID NO: 97; and
(c) a third nucleic acid molecule encoding a common LCVR comprising the amino acid sequence of SEQ ID NO: 82, wherein the third nucleic acid molecule comprises the nucleotide sequence of SEQ ID NO: 81.

7. The group of nucleic acid molecules of claim 3, wherein the bispecific antigen-binding molecule is a bispecific antibody, the first nucleic acid molecule encodes a first heavy, the second nucleic acid molecule encodes a second heavy chain, and the third nucleic acid molecule encodes a common light chain.

8. The group of nucleic acid molecules of claim 7, wherein the first heavy chain, the second heavy chain, or both the first and second heavy chains comprise a human IgG heavy chain constant region.

9. The group of nucleic acid molecules of claim 8, wherein the first heavy chain, the second heavy chain, or both the first and second heavy chains comprise a human IgG1 heavy chain constant region.

10. The group of nucleic acid molecules of claim 8, wherein the first heavy chain, the second heavy chain, or both the first and second heavy chains comprise a human IgG4 heavy chain constant region.

11. An expression vector comprising the group of nucleic acid molecules of claim 1.

12. A host cell comprising the expression vector of claim 11.

13. An isolated host cell comprising the group of nucleic acid molecules of claim 1.

14. A group of expression vectors comprising, respectively, the group of nucleic acid molecules of claim 1.

15. A host cell comprising the group of expression vectors of claim 14.

16. An expression vector comprising the group of nucleic acid molecules of claim 6.

17. A host cell comprising the expression vector of claim 16.

18. An isolated host cell comprising the group of nucleic acid molecules of claim 6.

19. A group of expression vectors comprising, respectively, the group of nucleic acid molecules of claim 6.

20. A host cell comprising the group of expression vectors of claim 19.

* * * * *

SEQUENCE LISTING

```
<160> NUMBER OF SEQ ID NOS: 125

<210> SEQ ID NO 1
<211> LENGTH: 366
<212> TYPE: DNA
<213> ORGANISM: Artificial Sequence
<220> FEATURE:
<223> OTHER INFORMATION: synthetic

<400> SEQUENCE: 1
caggtgcagc tggtggagtc ggggggaggc gtggtccagc ctgggaggtc cctgagactc      60
tcctgtgcag cctctggatt caccttcagt acctatggca ttcactgggt ccgccaggct     120
ccaggcaagg ggctggagtg ggtggcagtt atattacatg atggaagtag taactactat     180
gcagagtccg tgaagggccg attcatcatc tccagagaca attccaagaa cacactgtat     240
ctgcaaatga acagcctgag agctgaggac acggctctat attactgtac gaaaaggtat     300
tcagaagcag ctggcccaaa ttggttcgac ccctggggcc agggaaccct ggtcaccgtc     360
tcctca                                                                366

<210> SEQ ID NO 2
<211> LENGTH: 122
<212> TYPE: PRT
<213> ORGANISM: Artificial Sequence
<220> FEATURE:
<223> OTHER INFORMATION: synthetic

<400> SEQUENCE: 2

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Thr Tyr
             20                  25                  30

Gly Ile His Trp Val Arg Gln Ala Pro Gly Lys Gly Leu Glu Trp Val
         35                  40                  45

Ala Val Ile Leu His Asp Gly Ser Ser Asn Tyr Tyr Ala Glu Ser Val
     50                  55                  60
```

Lys Gly Arg Phe Ile Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Thr Lys Arg Tyr Ser Glu Ala Ala Gly Pro Asn Trp Phe Asp Pro Trp
            100                 105                 110

Gly Gln Gly Thr Leu Val Thr Val Ser Ser
        115                 120

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
ggattcacct tcagtaccta tggc                                          24

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

Gly Phe Thr Phe Ser Thr Tyr Gly
1               5

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
atattacatg atggaagtag taac                                          24

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Ile Leu His Asp Gly Ser Ser Asn
1               5

<210> SEQ ID NO 7
<211> LENGTH: 45
<212> TYPE: DNA
<213> ORGANISM: Artificial Sequence
<220> FEATURE:
<223> OTHER INFORMATION: synthetic

<400> SEQUENCE: 7
acgaaaaggt attcagaagc agctggccca aattggttcg acccc                   45

<210> SEQ ID NO 8
<211> LENGTH: 15
<212> TYPE: PRT

<213> ORGANISM: Artificial Sequence
<220> FEATURE:
<223> OTHER INFORMATION: synthetic

<400> SEQUENCE: 8

Thr Lys Arg Tyr Ser Glu Ala Ala Gly Pro Asn Trp Phe Asp Pro
1               5                   10                  15

<210> SEQ ID NO 9
<211> LENGTH: 321
<212> TYPE: DNA
<213> ORGANISM: Artificial Sequence
<220> FEATURE:
<223> OTHER INFORMATION: synthetic

<400> SEQUENCE: 9
gacatccaga tgacccagtc tccatcctcc gtgtctgcat ctgtaggaga cagagtcacc    60
atcacttgtc gggcgagtcg gggaattagc agctggttag cctggtatca gcagaagcca   120
gggaaagccc ctaagctcct gatccatgct gcatccagtt tgcaaagtgg ggtcccatca   180
aggttcagcg gcagtggatc tgggacagat ttcactctca ccatcagcag cctgcagcct   240
gaagattttg ctacttacta ttgtcaacag gctatcagtt tcccattcac tttcggccct   300
gggaccaaag tggatatcaa a                                              321

<210> SEQ ID NO 10
<211> LENGTH: 107
<212> TYPE: PRT
<213> ORGANISM: Artificial Sequence
<220> FEATURE:
<223> OTHER INFORMATION: synthetic

<400> SEQUENCE: 10

Asp Ile Gln Met Thr Gln Ser Pro Ser Ser Val Ser Ala Ser Val Gly
1               5                   10                  15

Asp Arg Val Thr Ile Thr Cys Arg Ala Ser Arg Gly Ile Ser Ser Trp
            20                  25                  30

Leu Ala Trp Tyr Gln Gln Lys Pro Gly Lys Ala Pro Lys Leu Leu Ile
        35                  40                  45

His Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ile Ser Phe Pro Phe
                85                  90                  95

Thr Phe Gly Pro Gly Thr Lys Val Asp Ile Lys
            100                 105

<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11
cggggaatta gcagctgg                                                   18

<210> SEQ ID NO 12
<211> LENGTH: 6
<212> TYPE: PRT
<213> ORGANISM: Artificial Sequence

```
<220> FEATURE:
<223> OTHER INFORMATION: synthetic

<400> SEQUENCE: 12

Arg Gly Ile Ser Ser Trp
1               5

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13 gctgcatcc                                                                  9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Ala Ala Ser
1

<210> SEQ ID NO 15
<211> LENGTH: 27
<212> TYPE: DNA
<213> ORGANISM: Artificial Sequence
<220> FEATURE:
<223> OTHER INFORMATION: synthetic

<400> SEQUENCE: 15
caacaggcta tcagtttccc attcact                                             27

<210> SEQ ID NO 16
<211> LENGTH: 9
<212> TYPE: PRT
<213> ORGANISM: Artificial Sequence
<220> FEATURE:
<223> OTHER INFORMATION: synthetic

<400> SEQUENCE: 16

Gln Gln Ala Ile Ser Phe Pro Phe Thr
1               5

<210> SEQ ID NO 17
<211> LENGTH: 360
<212> TYPE: DNA
<213> ORGANISM: Artificial Sequence
<220> FEATURE:
<223> OTHER INFORMATION: synthetic

<400> SEQUENCE: 17
gaggtgcagc tggtggagtc tgggggaggc ttggtacagc ctgggggtc cctgagactc          60 tcctgtgcag cctctggatt cacctttagc agctatgtca tgagttgggt ccgccaggct        120
ccagggaagg gactggagtg gtctcagct attattggta gtggtggtag cacatattac         180
gcagactccg tgaagggccg gttcaccatc tccagagaca attccaagaa cacgctgtat        240
ctgcaaatga acagcctgag agccgaggac acggccgtat attactgtgc gaaaagagcc       300
ggggataact ggaactggtt cgacccctgg ggccagggaa ccctggtcac cgtctcctca        360
```

<210> SEQ ID NO 18
<211> LENGTH: 120
<212> TYPE: PRT
<213> ORGANISM: Artificial Sequence
<220> FEATURE:
<223> OTHER INFORMATION: synthetic

<400> SEQUENCE: 18

```
Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Ser Tyr
            20                  25                  30

Val Met Ser Trp Val Arg Gln Ala Pro Gly Lys Gly Leu Glu Trp Val
        35                  40                  45

Ser Ala Ile Ile Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Ala Gly Asp Asn Trp Asn Trp Phe Asp Pro Trp Gly Gln
            100                 105                 110

Gly Thr Leu Val Thr Val Ser Ser
        115                 120
```

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
ggattcacct ttagcagcta tgtc                                            24

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

```
Gly Phe Thr Phe Ser Ser Tyr Val
1               5
```

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
attattggta gtggtggtag caca                                            24

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

Ile Ile Gly Ser Gly Gly Ser Thr
1               5

<210> SEQ ID NO 23
<211> LENGTH: 39
<212> TYPE: DNA
<213> ORGANISM: Artificial Sequence
<220> FEATURE:
<223> OTHER INFORMATION: synthetic

<400> SEQUENCE: 23
gcgaaaagag ccggggataa ctggaactgg ttcgacccc                          39

<210> SEQ ID NO 24
<211> LENGTH: 13
<212> TYPE: PRT
<213> ORGANISM: Artificial Sequence
<220> FEATURE:
<223> OTHER INFORMATION: synthetic

<400> SEQUENCE: 24

Ala Lys Arg Ala Gly Asp Asn Trp Asn Trp Phe Asp Pro
1               5                   10

<210> SEQ ID NO 25
<211> LENGTH: 321
<212> TYPE: DNA
<213> ORGANISM: Artificial Sequence
<220> FEATURE:
<223> OTHER INFORMATION: synthetic

<400> SEQUENCE: 25
gacatccaga tgacccagtc tccatcttcc gtgtctgcat ctttaggaga cagagtcacc    60
atcacttgtc gggcgagtca gggtattagc agctggttag cctggtatca gcggaaacca   120
gggaaagccc ctaagctcct gatctatgct gcatccagtt tgcaaagtgg ggtcccatca   180
aggttcagcg gcagtggatc tgggcggat ttcactctca ccatcagcag cctgcagcct    240
gaagattttg caacttacta ttgtcaacag gctaaaagtg tcccattcac tttcggccct   300
gggaccaaag tggatatcaa a                                             321

<210> SEQ ID NO 26
<211> LENGTH: 107
<212> TYPE: PRT
<213> ORGANISM: Artificial Sequence
<220> FEATURE:
<223> OTHER INFORMATION: synthetic

<400> SEQUENCE: 26

Asp Ile Gln Met Thr Gln Ser Pro Ser Ser Val Ser Ala Ser Leu Gly
1               5                   10                  15

Asp Arg Val Thr Ile Thr Cys Arg Ala Ser Gln Gly Ile Ser Ser Trp
            20                  25                  30

Leu Ala Trp Tyr Gln Arg Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Ala Asp Phe Thr Leu Thr Ile Ser Ser Leu Gln Pro
65                  70                  75                  80

Glu Asp Phe Ala Thr Tyr Tyr Cys Gln Gln Ala Lys Ser Val Pro Phe

```
                85                  90                  95

Thr Phe Gly Pro Gly Thr Lys Val Asp Ile Lys
            100                 105

<210> SEQ ID NO 27
<211> LENGTH: 18
<212> TYPE: DNA
<213> ORGANISM: Artificial Sequence
<220> FEATURE:
<223> OTHER INFORMATION: synthetic

<400> SEQUENCE: 27
cagggtatta gcagctgg                                                   18

<210> SEQ ID NO 28
<211> LENGTH: 6
<212> TYPE: PRT
<213> ORGANISM: Artificial Sequence
<220> FEATURE:
<223> OTHER INFORMATION: synthetic

<400> SEQUENCE: 28

Gln Gly Ile Ser Ser Trp
1               5

<210> SEQ ID NO 29
<211> LENGTH: 9
<212> TYPE: DNA
<213> ORGANISM: Artificial Sequence
<220> FEATURE:
<223> OTHER INFORMATION: synthetic

<400> SEQUENCE: 29 gctgcatcc                                                              9

<210> SEQ ID NO 30
<211> LENGTH: 3
<212> TYPE: PRT
<213> ORGANISM: Artificial Sequence
<220> FEATURE:
<223> OTHER INFORMATION: synthetic

<400> SEQUENCE: 30

Ala Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: synthetic

<400> SEQUENCE: 31
caacaggcta aaagtgtccc attcact                                         27

<210> SEQ ID NO 32
<211> LENGTH: 9
<212> TYPE: PRT
<213> ORGANISM: Artificial Sequence
<220> FEATURE:
<223> OTHER INFORMATION: synthetic

<400> SEQUENCE: 32

Gln Gln Ala Lys Ser Val Pro Phe Thr
1               5
```

<210> SEQ ID NO 33
<211> LENGTH: 351
<212> TYPE: DNA
<213> ORGANISM: Artificial Sequence
<220> FEATURE:
<223> OTHER INFORMATION: synthetic

<400> SEQUENCE: 33

```
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg gtctcaggt atcagttgga atagtggtaa catgggatat      180
gcggactctg tgaagggccg attcaccatc tccagagaca acgccaagaa ctccctgttc     240
ctgcaaatgc acagtttgag agctgaggac acggcctttt attactgtgc aaaagtccgt    300
ctaactgcct ttgactttg gggccaggga accctggtca ccgtctcctc a               351
```

<210> SEQ ID NO 34
<211> LENGTH: 117
<212> TYPE: PRT
<213> ORGANISM: Artificial Sequence
<220> FEATURE:
<223> OTHER INFORMATION: synthetic

<400> SEQUENCE: 34

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Asn Met Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met His Ser Leu Arg Ala Glu Asp Thr Ala Phe Tyr Tyr Cys
                85                  90                  95

Ala Lys Val Arg Leu Thr Ala Phe Asp Phe Trp Gly Gln Gly Thr Leu
            100                 105                 110

Val Thr Val Ser Ser
        115
```

<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35

```
ggattcacct ttgatgatta tgcc                                              24
```

<210> SEQ ID NO 36
<211> LENGTH: 8
<212> TYPE: PRT
<213> ORGANISM: Artificial Sequence
<220> FEATURE:
<223> OTHER INFORMATION: synthetic

<400> SEQUENCE: 36

Gly Phe Thr Phe Asp Asp Tyr Ala
1               5

<210> SEQ ID NO 37
<211> LENGTH: 24
<212> TYPE: DNA
<213> ORGANISM: Artificial Sequence
<220> FEATURE:
<223> OTHER INFORMATION: synthetic

<400> SEQUENCE: 37
atcagttgga atagtggtaa catg                                          24

<210> SEQ ID NO 38
<211> LENGTH: 8
<212> TYPE: PRT
<213> ORGANISM: Artificial Sequence
<220> FEATURE:
<223> OTHER INFORMATION: synthetic

<400> SEQUENCE: 38

Ile Ser Trp Asn Ser Gly Asn Met
1               5

<210> SEQ ID NO 39
<211> LENGTH: 30
<212> TYPE: DNA
<213> ORGANISM: Artificial Sequence
<220> FEATURE:
<223> OTHER INFORMATION: synthetic

<400> SEQUENCE: 39
gcaaaagtcc gtctaactgc ctttgacttt                                    30

<210> SEQ ID NO 40
<211> LENGTH: 10
<212> TYPE: PRT
<213> ORGANISM: Artificial Sequence
<220> FEATURE:
<223> OTHER INFORMATION: synthetic

<400> SEQUENCE: 40

Ala Lys Val Arg Leu Thr Ala Phe Asp Phe
1               5                   10

<210> SEQ ID NO 41
<211> LENGTH: 321
<212> TYPE: DNA
<213> ORGANISM: Artificial Sequence
<220> FEATURE:
<223> OTHER INFORMATION: synthetic

<400> SEQUENCE: 41
gacatccaga tgacccagtc tccatcctcc ctgtctgcat ctgtaggaga cagagtcacc    60
atcacttgcc ggacaagtca gagcattggc aactatttaa attggtttca gcagaaacca   120
gggaaagccc ctaaactcct catctatact gcatccagtt tgcagaatgg agtcccatca   180
aggttcactg gcagtggatc tgggacagat ttcactctca ccatcagcag tctgcaacct   240
gaggattttg taatttacta ctgtcaacag agtttcagta ccccgtatac ttttggccag   300
gggaccaagc tggagatcaa a                                            321

<210> SEQ ID NO 42
<211> LENGTH: 107
<212> TYPE: PRT

<213> ORGANISM: Artificial Sequence
<220> FEATURE:
<223> OTHER INFORMATION: synthetic

<400> SEQUENCE: 42

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Gly Asn Tyr
            20                  25                  30

Leu Asn Trp Phe Gln Gln Lys Pro Gly Lys Ala Pro Lys Leu Leu Ile
        35                  40                  45

Tyr Thr Ala Ser Ser Leu Gln Asn Gly Val Pro Ser Arg Phe Thr Gly
50                  55                  60

Ser Gly Ser Gly Thr Asp Phe Thr Leu Thr Ile Ser Ser Leu Gln Pro
65                  70                  75                  80

Glu Asp Phe Val Ile Tyr Tyr Cys Gln Gln Ser Phe Ser Thr Pro Tyr
                85                  90                  95

Thr Phe Gly Gln Gly Thr Lys Leu Glu Ile Lys
            100                 105
```

<210> SEQ ID NO 43
<211> LENGTH: 18
<212> TYPE: DNA
<213> ORGANISM: Artificial Sequence
<220> FEATURE:
<223> OTHER INFORMATION: synthetic

<400> SEQUENCE: 43
cagagcattg gcaactat                                              18

<210> SEQ ID NO 44
<211> LENGTH: 6
<212> TYPE: PRT
<213> ORGANISM: Artificial Sequence
<220> FEATURE:
<223> OTHER INFORMATION: synthetic

<400> SEQUENCE: 44

```
Gln Ser Ile Gly Asn Tyr
1               5
```

<210> SEQ ID NO 45
<211> LENGTH: 9
<212> TYPE: DNA
<213> ORGANISM: Artificial Sequence
<220> FEATURE:
<223> OTHER INFORMATION: synthetic

<400> SEQUENCE: 45 actgcatcc                                                         9

<210> SEQ ID NO 46
<211> LENGTH: 3
<212> TYPE: PRT
<213> ORGANISM: Artificial Sequence
<220> FEATURE:
<223> OTHER INFORMATION: synthetic

<400> SEQUENCE: 46

```
Thr Ala Ser
1
```

<210> SEQ ID NO 47

```
<211> LENGTH: 27
<212> TYPE: DNA
<213> ORGANISM: Artificial Sequence
<220> FEATURE:
<223> OTHER INFORMATION: synthetic

<400> SEQUENCE: 47
caacagagtt tcagtacccc gtatact                                              27

<210> SEQ ID NO 48
<211> LENGTH: 9
<212> TYPE: PRT
<213> ORGANISM: Artificial Sequence
<220> FEATURE:
<223> OTHER INFORMATION: synthetic

<400> SEQUENCE: 48

Gln Gln Ser Phe Ser Thr Pro Tyr Thr
1               5

<210> SEQ ID NO 49
<211> LENGTH: 354
<212> TYPE: DNA
<213> ORGANISM: Artificial Sequence
<220> FEATURE:
<223> OTHER INFORMATION: synthetic

<400> SEQUENCE: 49
caggtgcagc tggtggagtc tgggggaggc ttggtcaagc ctggagggtc cctgagactc          60
tcctgtgcag cctctggatt caccttcagt gactactaca tcagctggat ccgccaggct         120
ccagggaagg gctggagtg gtttcatac attagttcta gtggtagttc cataaagtac           180
gcagactctg tgaagggccg attcaccatc tccagggaca cgccaagaa ctcactgtat          240 ctgcaaatga acagcctgag agccgaggac acggccgtat attactgtgc gagagaggga         300
gggaactacg gtatggacgt ctggggccaa gggaccacgg tcaccgtctc ctca              354

<210> SEQ ID NO 50
<211> LENGTH: 118
<212> TYPE: PRT
<213> ORGANISM: Artificial Sequence
<220> FEATURE:
<223> OTHER INFORMATION: synthetic

<400> SEQUENCE: 50

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Ile Ser Trp Ile Arg Gln Ala Pro Gly Lys Gly Leu Glu Trp Val
        35                  40                  45

Ser Tyr Ile Ser Ser Ser Gly Ser Ser Ile Lys Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Asn Tyr Gly Met Asp Val Trp Gly Gln Gly Thr
            100                 105                 110

Thr Val Thr Val Ser Ser
        115
```

<210> SEQ ID NO 51
<211> LENGTH: 24
<212> TYPE: DNA
<213> ORGANISM: Artificial Sequence
<220> FEATURE:
<223> OTHER INFORMATION: synthetic

<400> SEQUENCE: 51
ggattcacct tcagtgacta ctac                                      24

<210> SEQ ID NO 52
<211> LENGTH: 8
<212> TYPE: PRT
<213> ORGANISM: Artificial Sequence
<220> FEATURE:
<223> OTHER INFORMATION: synthetic

<400> SEQUENCE: 52

Gly Phe Thr Phe Ser Asp Tyr Tyr
1               5

<210> SEQ ID NO 53
<211> LENGTH: 24
<212> TYPE: DNA
<213> ORGANISM: Artificial Sequence
<220> FEATURE:
<223> OTHER INFORMATION: synthetic

<400> SEQUENCE: 53
attagttcta gtggtagttc cata                                      24

<210> SEQ ID NO 54
<211> LENGTH: 8
<212> TYPE: PRT
<213> ORGANISM: Artificial Sequence
<220> FEATURE:
<223> OTHER INFORMATION: synthetic

<400> SEQUENCE: 54

Ile Ser Ser Ser Gly Ser Ser Ile
1               5

<210> SEQ ID NO 55
<211> LENGTH: 33
<212> TYPE: DNA
<213> ORGANISM: Artificial Sequence
<220> FEATURE:
<223> OTHER INFORMATION: synthetic

<400> SEQUENCE: 55
gcgagagagg gagggaacta cggtatggac gtc                            33

<210> SEQ ID NO 56
<211> LENGTH: 11
<212> TYPE: PRT
<213> ORGANISM: Artificial Sequence
<220> FEATURE:
<223> OTHER INFORMATION: synthetic

<400> SEQUENCE: 56

Ala Arg Glu Gly Gly Asn Tyr Gly Met Asp Val
1               5                   10

<210> SEQ ID NO 57
<211> LENGTH: 321
<212> TYPE: DNA

<213> ORGANISM: Artificial Sequence
<220> FEATURE:
<223> OTHER INFORMATION: synthetic

<400> SEQUENCE: 57

```
gacatccaga tgacccagtc tccatcttcc gtgtctgcat ctgtaggaga cagagtcacc    60
atcacttgtc gggcgagtca gggtattaac aactggttag tctggtatca gcagaaacca   120
gggaaagccc ctaagctcct gatctatgct gcaaccagct tgcaaagtgg ggtcccatca   180
aggttcagcg gcagtgggtc tgggacagat ttcactctca ccatcagcag cctgcagcct   240
gaagattttg caacttacta ttgtcaacag gctaacagtt ccctcccac ttttggccag    300
gggaccaagc tggagatcaa a                                             321
```

<210> SEQ ID NO 58
<211> LENGTH: 107
<212> TYPE: PRT
<213> ORGANISM: Artificial Sequence
<220> FEATURE:
<223> OTHER INFORMATION: synthetic

<400> SEQUENCE: 58

```
Asp Ile Gln Met Thr Gln Ser Pro Ser Ser Val Ser Ala Ser Val Gly
 1               5                  10                  15
Asp Arg Val Thr Ile Thr Cys Arg Ala Ser Gln Gly Ile Asn Asn Trp
             20                  25                  30
Leu Val Trp Tyr Gln Gln Lys Pro Gly Lys Ala Pro Lys Leu Leu Ile
         35                  40                  45
Tyr Ala Ala Thr Ser Leu Gln Ser Gly Val Pro Ser Arg Phe Ser Gly
     50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ala Asn Ser Phe Pro Pro
                 85                  90                  95
Thr Phe Gly Gln Gly Thr Lys Leu Glu Ile Lys
            100                 105
```

<210> SEQ ID NO 59
<211> LENGTH: 18
<212> TYPE: DNA
<213> ORGANISM: Artificial Sequence
<220> FEATURE:
<223> OTHER INFORMATION: synthetic

<400> SEQUENCE: 59

```
cagggtatta acaactgg                                                  18
```

<210> SEQ ID NO 60
<211> LENGTH: 6
<212> TYPE: PRT
<213> ORGANISM: Artificial Sequence
<220> FEATURE:
<223> OTHER INFORMATION: synthetic

<400> SEQUENCE: 60

```
Gln Gly Ile Asn Asn Trp
 1               5
```

<210> SEQ ID NO 61
<211> LENGTH: 9
<212> TYPE: DNA
<213> ORGANISM: Artificial Sequence

```
<220> FEATURE:
<223> OTHER INFORMATION: synthetic

<400> SEQUENCE: 61 gctgcaacc                                                                 9

<210> SEQ ID NO 62
<211> LENGTH: 3
<212> TYPE: PRT
<213> ORGANISM: Artificial Sequence
<220> FEATURE:
<223> OTHER INFORMATION: synthetic

<400> SEQUENCE: 62

Ala Ala Thr
1

<210> SEQ ID NO 63
<211> LENGTH: 27
<212> TYPE: DNA
<213> ORGANISM: Artificial Sequence
<220> FEATURE:
<223> OTHER INFORMATION: synthetic

<400> SEQUENCE: 63
caacaggcta acagtttccc tcccact                                            27

<210> SEQ ID NO 64
<211> LENGTH: 9
<212> TYPE: PRT
<213> ORGANISM: Artificial Sequence
<220> FEATURE:
<223> OTHER INFORMATION: synthetic

<400> SEQUENCE: 64

Gln Gln Ala Asn Ser Phe Pro Pro Thr
1               5

<210> SEQ ID NO 65
<211> LENGTH: 375
<212> TYPE: DNA
<213> ORGANISM: Artificial Sequence
<220> FEATURE:
<223> OTHER INFORMATION: synthetic

<400> SEQUENCE: 65
gaggtgcagc tggtggagtc tgggggaggc ttggtccagc ctggggggtc cctgagactc         60
tcctgtgcag cctctggatt cacctttagt aactttggga tgacctgggt ccgccaggct        120
ccagggaagg ggctggagtg ggtggccaac atgaaccaag atggaagtga aaatactat         180 gtggactctg tgaagggccg attcaccatc tccagagaca cgccaagag ctcactgtat         240 ctgcaaatga acagcctgag agccgaggac acggctgtgt attactgtgc gagagatcgg        300
gaatattgta ttagtaccag ctgctatgat gactttgact actggggcca gggaaccctg        360
gtcaccgtct cctca                                                        375

<210> SEQ ID NO 66
<211> LENGTH: 125
<212> TYPE: PRT
<213> ORGANISM: Artificial Sequence
<220> FEATURE:
<223> OTHER INFORMATION: synthetic

<400> SEQUENCE: 66
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Trp Met Thr Trp Val Arg Gln Ala Pro Gly Lys Gly Leu Glu Trp Val
        35                  40                  45

Ala Asn Met Asn Gln Asp Gly Ser Glu Lys Tyr Tyr Val Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Glu Tyr Cys Ile Ser Thr Ser Cys Tyr Asp Asp Phe
                100                 105                 110

Asp Tyr Trp Gly Gln Gly Thr Leu Val Thr Val Ser Ser
            115                 120                 125

<210> SEQ ID NO 67
<211> LENGTH: 24
<212> TYPE: DNA
<213> ORGANISM: Artificial Sequence
<220> FEATURE:
<223> OTHER INFORMATION: synthetic

<400> SEQUENCE: 67
ggattcacct ttagtaactt ttgg                                      24

<210> SEQ ID NO 68
<211> LENGTH: 8
<212> TYPE: PRT
<213> ORGANISM: Artificial Sequence
<220> FEATURE:
<223> OTHER INFORMATION: synthetic

<400> SEQUENCE: 68

Gly Phe Thr Phe Ser Asn Phe Trp
1               5

<210> SEQ ID NO 69
<211> LENGTH: 24
<212> TYPE: DNA
<213> ORGANISM: Artificial Sequence
<220> FEATURE:
<223> OTHER INFORMATION: synthetic

<400> SEQUENCE: 69
atgaaccaag atggaagtga gaaa                                      24

<210> SEQ ID NO 70
<211> LENGTH: 8
<212> TYPE: PRT
<213> ORGANISM: Artificial Sequence
<220> FEATURE:
<223> OTHER INFORMATION: synthetic

<400> SEQUENCE: 70

Met Asn Gln Asp Gly Ser Glu Lys
1               5

<210> SEQ ID NO 71
<211> LENGTH: 54
<212> TYPE: DNA
<213> ORGANISM: Artificial Sequence
<220> FEATURE:
<223> OTHER INFORMATION: synthetic

<400> SEQUENCE: 71
gcgagagatc gggaatattg tattagtacc agctgctatg atgactttga ctac    54

<210> SEQ ID NO 72
<211> LENGTH: 18
<212> TYPE: PRT
<213> ORGANISM: Artificial Sequence
<220> FEATURE:
<223> OTHER INFORMATION: synthetic

<400> SEQUENCE: 72

Ala Arg Asp Arg Glu Tyr Cys Ile Ser Thr Ser Cys Tyr Asp Asp Phe
1               5                   10                  15

Asp Tyr

<210> SEQ ID NO 73
<211> LENGTH: 324
<212> TYPE: DNA
<213> ORGANISM: Artificial Sequence
<220> FEATURE:
<223> OTHER INFORMATION: synthetic

<400> SEQUENCE: 73
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcatagtgg ggtcccatca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                          324

<210> SEQ ID NO 74
<211> LENGTH: 108
<212> TYPE: PRT
<213> ORGANISM: Artificial Sequence
<220> FEATURE:
<223> OTHER INFORMATION: synthetic

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 75
<211> LENGTH: 18
<212> TYPE: DNA

```
<213> ORGANISM: Artificial Sequence
<220> FEATURE:
<223> OTHER INFORMATION: synthetic

<400> SEQUENCE: 75
cagagcatta gcagctat                                                 18

<210> SEQ ID NO 76
<211> LENGTH: 6
<212> TYPE: PRT
<213> ORGANISM: Artificial Sequence
<220> FEATURE:
<223> OTHER INFORMATION: synthetic

<400> SEQUENCE: 76

Gln Ser Ile Ser Ser Tyr
1               5

<210> SEQ ID NO 77
<211> LENGTH: 9
<212> TYPE: DNA
<213> ORGANISM: Artificial Sequence
<220> FEATURE:
<223> OTHER INFORMATION: synthetic

<400> SEQUENCE: 77 gctgcatcc                                                            9

<210> SEQ ID NO 78
<211> LENGTH: 3
<212> TYPE: PRT
<213> ORGANISM: Artificial Sequence
<220> FEATURE:
<223> OTHER INFORMATION: synthetic

<400> SEQUENCE: 78

Ala Ala Ser
1

<210> SEQ ID NO 79
<211> LENGTH: 30
<212> TYPE: DNA
<213> ORGANISM: Artificial Sequence
<220> FEATURE:
<223> OTHER INFORMATION: synthetic

<400> SEQUENCE: 79
caacagagtt acagtacccc tccgatcacc                                    30

<210> SEQ ID NO 80
<211> LENGTH: 10
<212> TYPE: PRT
<213> ORGANISM: Artificial Sequence
<220> FEATURE:
<223> OTHER INFORMATION: synthetic

<400> SEQUENCE: 80

Gln Gln Ser Tyr Ser Thr Pro Pro Ile Thr
1               5                   10

<210> SEQ ID NO 81
<211> LENGTH: 324
<212> TYPE: DNA
<213> ORGANISM: Artificial Sequence
<220> FEATURE:
<223> OTHER INFORMATION: synthetic
```

<400> SEQUENCE: 81

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                          324
```

<210> SEQ ID NO 82
<211> LENGTH: 108
<212> TYPE: PRT
<213> ORGANISM: Artificial Sequence
<220> FEATURE:
<223> OTHER INFORMATION: synthetic

<400> SEQUENCE: 82

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```

<210> SEQ ID NO 83
<211> LENGTH: 18
<212> TYPE: DNA
<213> ORGANISM: Artificial Sequence
<220> FEATURE:
<223> OTHER INFORMATION: synthetic

<400> SEQUENCE: 83

```
cagagcatta gcagctat                                                  18
```

<210> SEQ ID NO 84
<211> LENGTH: 6
<212> TYPE: PRT
<213> ORGANISM: Artificial Sequence
<220> FEATURE:
<223> OTHER INFORMATION: synthetic

<400> SEQUENCE: 84

```
Gln Ser Ile Ser Ser Tyr
1               5
```

<210> SEQ ID NO 85
<211> LENGTH: 9
<212> TYPE: DNA
<213> ORGANISM: Artificial Sequence
<220> FEATURE:
<223> OTHER INFORMATION: synthetic

<400> SEQUENCE: 85

<210> SEQ ID NO 86
<211> LENGTH: 3
<212> TYPE: PRT
<213> ORGANISM: Artificial Sequence
<220> FEATURE:
<223> OTHER INFORMATION: synthetic

<400> SEQUENCE: 86

Ala Ala Ser
1

<210> SEQ ID NO 87
<211> LENGTH: 30
<212> TYPE: DNA
<213> ORGANISM: Artificial Sequence
<220> FEATURE:
<223> OTHER INFORMATION: synthetic

<400> SEQUENCE: 87
caacagagtt acagtacccc tccgatcacc                                    30

<210> SEQ ID NO 88
<211> LENGTH: 10
<212> TYPE: PRT
<213> ORGANISM: Artificial Sequence
<220> FEATURE:
<223> OTHER INFORMATION: synthetic

<400> SEQUENCE: 88

Gln Gln Ser Tyr Ser Thr Pro Pro Ile Thr
1               5                   10

<210> SEQ ID NO 89
<211> LENGTH: 372
<212> TYPE: DNA
<213> ORGANISM: Artificial Sequence
<220> FEATURE:
<223> OTHER INFORMATION: synthetic

<400> SEQUENCE: 89
gaagtacagc ttgtagaatc cggcggagga ctggtacaac ctggaagaag tcttagactg    60
agttgcgcag ctagtgggtt acattcgac gattacagca tgcattgggt gaggcaagct   120
cctggtaaag gattgaatg ggttagcggg atatcatgga actcaggaag caagggatac   180
gccgacagcg tgaaaggccg atttacaata tctagggaca cgcaaaaaa ctctctctac   240 cttcaaatga actctcttag ggcagaagac acagcattgt attattgcgc aaaatacggc   300
agtggttatg gcaagtttta tcattatgga ctggacgtgt ggggacaagg gacaacagtg   360
acagtgagta gc                                                      372

<210> SEQ ID NO 90
<211> LENGTH: 124
<212> TYPE: PRT
<213> ORGANISM: Artificial Sequence
<220> FEATURE:
<223> OTHER INFORMATION: synthetic

<400> SEQUENCE: 90

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr

```
                20                  25                  30
Ser Met His Trp Val Arg Gln Ala Pro Gly Lys Gly Leu Glu Trp Val
        35                  40                  45

Ser Gly Ile Ser Trp Asn Ser Gly Ser Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr His Tyr Gly Leu Asp
            100                 105                 110

Val Trp Gly Gln Gly Thr Thr Val Thr Val Ser Ser
            115                 120
```

<210> SEQ ID NO 91
<211> LENGTH: 24
<212> TYPE: DNA
<213> ORGANISM: Artificial Sequence
<220> FEATURE:
<223> OTHER INFORMATION: synthetic

<400> SEQUENCE: 91
gggtttacat tcgacgatta cagc                                          24

<210> SEQ ID NO 92
<211> LENGTH: 8
<212> TYPE: PRT
<213> ORGANISM: Artificial Sequence
<220> FEATURE:
<223> OTHER INFORMATION: synthetic

<400> SEQUENCE: 92

Gly Phe Thr Phe Asp Asp Tyr Ser
1               5

<210> SEQ ID NO 93
<211> LENGTH: 24
<212> TYPE: DNA
<213> ORGANISM: Artificial Sequence
<220> FEATURE:
<223> OTHER INFORMATION: synthetic

<400> SEQUENCE: 93
atatcatgga actcaggaag caag                                          24

<210> SEQ ID NO 94
<211> LENGTH: 8
<212> TYPE: PRT
<213> ORGANISM: Artificial Sequence
<220> FEATURE:
<223> OTHER INFORMATION: synthetic

<400> SEQUENCE: 94

Ile Ser Trp Asn Ser Gly Ser Lys
1               5

<210> SEQ ID NO 95
<211> LENGTH: 51
<212> TYPE: DNA
<213> ORGANISM: Artificial Sequence
<220> FEATURE:
<223> OTHER INFORMATION: synthetic

<400> SEQUENCE: 95

```
gcaaaatacg gcagtggtta tggcaagttt tatcattatg gactggacgt g        51
```

<210> SEQ ID NO 96
<211> LENGTH: 17
<212> TYPE: PRT
<213> ORGANISM: Artificial Sequence
<220> FEATURE:
<223> OTHER INFORMATION: synthetic

<400> SEQUENCE: 96

```
Ala Lys Tyr Gly Ser Gly Tyr Gly Lys Phe Tyr His Tyr Gly Leu Asp
1               5                   10                  15
Val
```

<210> SEQ ID NO 97
<211> LENGTH: 372
<212> TYPE: DNA
<213> ORGANISM: Artificial Sequence
<220> FEATURE:
<223> OTHER INFORMATION: synthetic

<400> SEQUENCE: 97

```
gaagtacagc ttgtagaatc cggcggagga ctggtacaac ctggaagaag tcttagactg     60
agttgcgcag ctagtgggtt tacattcgac gattacagca tgcattgggt gaggcaagct    120
cctggtaaag gattgaatg ggttagcggg atatcatgga actcaggaag catcggatac    180
gccgacagcg tgaaaggccg atttacaata tctagggaca acgcaaaaaa ctctctctac    240
cttcaaatga actctcttag gcagaagac acagcattgt attattgcgc aaaatacggc    300
agtggttatg gcaagtttta ttattatgga atggacgtgt ggggacaagg gacaacagtg    360
acagtgagta gc                                                        372
```

<210> SEQ ID NO 98
<211> LENGTH: 124
<212> TYPE: PRT
<213> ORGANISM: Artificial Sequence
<220> FEATURE:
<223> OTHER INFORMATION: synthetic

<400> SEQUENCE: 98

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
            85                  90                  95

Ala Lys Tyr Gly Ser Gly Tyr Gly Lys Phe Tyr Tyr Tyr Gly Met Asp
            100                 105                 110

Val Trp Gly Gln Gly Thr Thr Val Thr Val Ser Ser
        115                 120
```

<210> SEQ ID NO 99
<211> LENGTH: 24

```
<212> TYPE: DNA
<213> ORGANISM: Artificial Sequence
<220> FEATURE:
<223> OTHER INFORMATION: synthetic

<400> SEQUENCE: 99
gggtttacat tcgacgatta cagc                                           24

<210> SEQ ID NO 100
<211> LENGTH: 8
<212> TYPE: PRT
<213> ORGANISM: Artificial Sequence
<220> FEATURE:
<223> OTHER INFORMATION: synthetic

<400> SEQUENCE: 100

Gly Phe Thr Phe Asp Asp Tyr Ser
1               5

<210> SEQ ID NO 101
<211> LENGTH: 24
<212> TYPE: DNA
<213> ORGANISM: Artificial Sequence
<220> FEATURE:
<223> OTHER INFORMATION: synthetic

<400> SEQUENCE: 101
atatcatgga actcaggaag catc                                           24

<210> SEQ ID NO 102
<211> LENGTH: 8
<212> TYPE: PRT
<213> ORGANISM: Artificial Sequence
<220> FEATURE:
<223> OTHER INFORMATION: synthetic

<400> SEQUENCE: 102

Ile Ser Trp Asn Ser Gly Ser Ile
1               5

<210> SEQ ID NO 103
<211> LENGTH: 51
<212> TYPE: DNA
<213> ORGANISM: Artificial Sequence
<220> FEATURE:
<223> OTHER INFORMATION: synthetic

<400> SEQUENCE: 103
gcaaaatacg gcagtggtta tggcaagttt tattattatg gaatggacgt g             51

<210> SEQ ID NO 104
<211> LENGTH: 17
<212> TYPE: PRT
<213> ORGANISM: Artificial Sequence
<220> FEATURE:
<223> OTHER INFORMATION: synthetic

<400> SEQUENCE: 104

Ala Lys Tyr Gly Ser Gly Tyr Gly Lys Phe Tyr Tyr Tyr Gly Met Asp
1               5                   10                  15

Val

<210> SEQ ID NO 105
<211> LENGTH: 249
<212> TYPE: DNA
<213> ORGANISM: Artificial Sequence
```

```
<220> FEATURE:
<223> OTHER INFORMATION: hBCMA ecto.mmh

<400> SEQUENCE: 105
atgttgcaga tggctgggca gtgctcccaa aatgaatatt ttgacagttt gttgcatgct      60
tgcataccct gtcaacttcg atgttcttct aatactcctc ctctaacatg tcagcgttat     120
tgtaatgcaa gtgtgaccaa ttcagtgaaa ggaacgaatg cggaacaaaa actcatctca     180
gaagaggatc tgggtggaga acaaaaactc atctcagaag aggatctgca ccatcaccat     240
caccattga                                                             249

<210> SEQ ID NO 106
<211> LENGTH: 82
<212> TYPE: PRT
<213> ORGANISM: Artificial Sequence
<220> FEATURE:
<223> OTHER INFORMATION: hBCMA ecto.mmh

<400> SEQUENCE: 106

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Glu Gln Lys Leu Ile Ser Glu Glu Asp Leu
    50                  55                  60

Gly Gly Glu Gln Lys Leu Ile Ser Glu Glu Asp Leu His His His His
65                  70                  75                  80

His His

<210> SEQ ID NO 107
<211> LENGTH: 864
<212> TYPE: DNA
<213> ORGANISM: Artificial Sequence
<220> FEATURE:
<223> OTHER INFORMATION: hBCMA ecto.mFc

<400> SEQUENCE: 107
atgttgcaga tggctgggca gtgctcccaa aatgaatatt ttgacagttt gttgcatgct      60
tgcataccct gtcaacttcg atgttcttct aatactcctc ctctaacatg tcagcgttat     120
tgtaatgcaa gtgtgaccaa ttcagtgaaa ggaacgaatg cggagcccag agggcccaca     180
atcaagccct gtcctccatg caaatgccca gcacctaacc tcttgggtgg accatccgtc     240
ttcatcttcc ctccaaagat caaggatgta ctcatgatct ccctgagccc catagtcaca     300
tgtgtggtgg tggatgtgag cgaggatgac ccagatgtcc agatcagctg gtttgtgaac     360
aacgtggaag tacacacagc tcagacacaa acccatagag aggattacaa cagtactctc     420
cgggtggtca gtgccctccc catccagcac caggactgga tgagtggcaa ggagttcaaa     480
tgcaaggtca acaacaaaga cctcccagcg cccatcgaga accatctc aaaacccaaa      540 gggtcagtaa gagctccaca ggtatatgtc ttgcctccac cagaagaaga tgactaag      600 aaacaggtca ctctgacctg catggtcaca gacttcatgc ctgaagacat ttacgtggag     660
tggaccaaca cgggaaaaac agagctaaac tacaagaaca ctgaaccagt cctggactct     720
gatggttctt acttcatgta cagcaagctg agagtgaaa agaagaactg ggtggaaaga     780
aatagctact cctgttcagt ggtccacgag ggtctgcaca tcaccacac gactaagagc     840
```
ttctcccgga ctccgggtaa atga                                                864

<210> SEQ ID NO 108
<211> LENGTH: 287
<212> TYPE: PRT
<213> ORGANISM: Artificial Sequence
<220> FEATURE:
<223> OTHER INFORMATION: hBCMA ecto.mFc

<400> SEQUENCE: 108

```
Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Glu Pro Arg Gly Pro Thr Ile Lys Pro Cys
    50                  55                  60

Pro Pro Cys Lys Cys Pro Ala Pro Asn Leu Leu Gly Gly Pro Ser Val
65                  70                  75                  80

Phe Ile Phe Pro Pro Lys Ile Lys Asp Val Leu Met Ile Ser Leu Ser
                85                  90                  95

Pro Ile Val Thr Cys Val Val Val Asp Val Ser Glu Asp Asp Pro Asp
            100                 105                 110

Val Gln Ile Ser Trp Phe Val Asn Asn Val Glu Val His Thr Ala Gln
        115                 120                 125

Thr Gln Thr His Arg Glu Asp Tyr Asn Ser Thr Leu Arg Val Val Ser
    130                 135                 140

Ala Leu Pro Ile Gln His Gln Asp Trp Met Ser Gly Lys Glu Phe Lys
145                 150                 155                 160

Cys Lys Val Asn Asn Lys Asp Leu Pro Ala Pro Ile Glu Arg Thr Ile
                165                 170                 175

Ser Lys Pro Lys Gly Ser Val Arg Ala Pro Gln Val Tyr Val Leu Pro
            180                 185                 190

Pro Pro Glu Glu Glu Met Thr Lys Lys Gln Val Thr Leu Thr Cys Met
        195                 200                 205

Val Thr Asp Phe Met Pro Glu Asp Ile Tyr Val Glu Trp Thr Asn Asn
    210                 215                 220

Gly Lys Thr Glu Leu Asn Tyr Lys Asn Thr Glu Pro Val Leu Asp Ser
225                 230                 235                 240

Asp Gly Ser Tyr Phe Met Tyr Ser Lys Leu Arg Val Glu Lys Lys Asn
                245                 250                 255

Trp Val Glu Arg Asn Ser Tyr Ser Cys Ser Val Val His Glu Gly Leu
            260                 265                 270

His Asn His His Thr Thr Lys Ser Phe Ser Arg Thr Pro Gly Lys
        275                 280                 285
```

<210> SEQ ID NO 109
<211> LENGTH: 246
<212> TYPE: DNA
<213> ORGANISM: Artificial Sequence
<220> FEATURE:
<223> OTHER INFORMATION: mfBCMA ecto.mmh

<400> SEQUENCE: 109
atgttgcaga tggctcggca gtgctcccaa aatgaatatt ttgacagttt gttgcatgat    60

```
tgcaaacctt gtcaacttcg atgttctagt actcctcctc taacatgtca gcgttattgc    120
aatgcaagta tgaccaattc agtgaaagga atgaatgcgg aacaaaaact catctcagaa    180
gaggatctgg gtggagaaca aaaactcatc tcagaagagg atctgcacca tcaccatcac    240
cattga                                                                246
```

<210> SEQ ID NO 110
<211> LENGTH: 81
<212> TYPE: PRT
<213> ORGANISM: Artificial Sequence
<220> FEATURE:
<223> OTHER INFORMATION: mfBCMA ecto.mmh

<400> SEQUENCE: 110

```
Met Leu Gln Met Ala Arg Gln Cys Ser Gln Asn Glu Tyr Phe Asp Ser
1               5                   10                  15

Leu Leu His Asp Cys Lys Pro Cys Gln Leu Arg Cys Ser Ser Thr Pro
            20                  25                  30

Pro Leu Thr Cys Gln Arg Tyr Cys Asn Ala Ser Met Thr Asn Ser Val
        35                  40                  45

Lys Gly Met Asn Ala Glu Gln Lys Leu Ile Ser Glu Glu Asp Leu Gly
    50                  55                  60

Gly Glu Gln Lys Leu Ile Ser Glu Glu Asp Leu His His His His
65                  70                  75                  80

His
```

<210> SEQ ID NO 111
<211> LENGTH: 861
<212> TYPE: DNA
<213> ORGANISM: Artificial Sequence
<220> FEATURE:
<223> OTHER INFORMATION: mfBCMA ecto.mFc

<400> SEQUENCE: 111

```
atgttgcaga tggctcggca gtgctcccaa atgaatatat ttgacagttt gttgcatgat     60
tgcaaacctt gtcaacttcg atgttctagt actcctcctc taacatgtca gcgttattgc    120
aatgcaagta tgaccaattc agtgaaagga atgaatgcgg agcccagagg gcccacaatc    180
aagccctgtc ctccatgcaa atgcccagcc ctaacctct gggtggacc atccgtcttc     240 atcttccctc caaagatcaa ggatgtactc atgatctccc tgagcccat agtcacatgt    300 gtggtggtgg atgtgagcga ggatgaccca gatgtccaga tcagctggtt tgtgaacaac    360
gtggaagtac acacagctca gacacaaacc catagagagg attacaacag tactctccgg    420
gtggtcagtg ccctccccat ccagcaccag gactggatga gtggcaagga gttcaaatgc    480
aaggtcaaca caaagacct cccagcgccc atcgagaaa ccatctcaaa acccaaaggg     540
tcagtaagag ctccacaggt atatgtcttg cctccaccag aagaagagat gactaagaaa    600
caggtcactc tgacctgcat ggtcacagac ttcatgcctg aagacattta cgtggagtgg    660
accaacaacg ggaaaacaga gctaaactac aagaacactg aaccagtcct ggactctgat    720
ggttcttact tcatgtacag caagctgaga gtgaaaaga gaactgggt ggaaagaaat     780 agctactcct gttcagtggt ccacgagggt ctgcacaatc accacacgac taagagcttc    840
tcccggactc cgggtaaatg a                                               861
```

<210> SEQ ID NO 112
<211> LENGTH: 286
<212> TYPE: PRT

<213> ORGANISM: Artificial Sequence
<220> FEATURE:
<223> OTHER INFORMATION: mfBCMA ecto.mFc

<400> SEQUENCE: 112

```
Met Leu Gln Met Ala Arg Gln Cys Ser Gln Asn Glu Tyr Phe Asp Ser
1               5                   10                  15

Leu Leu His Asp Cys Lys Pro Cys Gln Leu Arg Cys Ser Ser Thr Pro
            20                  25                  30

Pro Leu Thr Cys Gln Arg Tyr Cys Asn Ala Ser Met Thr Asn Ser Val
        35                  40                  45

Lys Gly Met Asn Ala Glu Pro Arg Gly Pro Thr Ile Lys Pro Cys Pro
    50                  55                  60

Pro Cys Lys Cys Pro Ala Pro Asn Leu Leu Gly Gly Pro Ser Val Phe
65              70                  75                  80

Ile Phe Pro Pro Lys Ile Lys Asp Val Leu Met Ile Ser Leu Ser Pro
                85                  90                  95

Ile Val Thr Cys Val Val Val Asp Val Ser Glu Asp Asp Pro Asp Val
            100                 105                 110

Gln Ile Ser Trp Phe Val Asn Asn Val Glu Val His Thr Ala Gln Thr
        115                 120                 125

Gln Thr His Arg Glu Asp Tyr Asn Ser Thr Leu Arg Val Val Ser Ala
    130                 135                 140

Leu Pro Ile Gln His Gln Asp Trp Met Ser Gly Lys Glu Phe Lys Cys
145             150                 155                 160

Lys Val Asn Asn Lys Asp Leu Pro Ala Pro Ile Glu Arg Thr Ile Ser
                165                 170                 175

Lys Pro Lys Gly Ser Val Arg Ala Pro Gln Val Tyr Val Leu Pro Pro
            180                 185                 190

Pro Glu Glu Glu Met Thr Lys Lys Gln Val Thr Leu Thr Cys Met Val
        195                 200                 205

Thr Asp Phe Met Pro Glu Asp Ile Tyr Val Glu Trp Thr Asn Asn Gly
    210                 215                 220

Lys Thr Glu Leu Asn Tyr Lys Asn Thr Glu Pro Val Leu Asp Ser Asp
225             230                 235                 240

Gly Ser Tyr Phe Met Tyr Ser Lys Leu Arg Val Glu Lys Lys Asn Trp
                245                 250                 255

Val Glu Arg Asn Ser Tyr Ser Cys Ser Val Val His Glu Gly Leu His
            260                 265                 270

Asn His His Thr Thr Lys Ser Phe Ser Arg Thr Pro Gly Lys
        275                 280                 285
```

<210> SEQ ID NO 113
<211> LENGTH: 849
<212> TYPE: DNA
<213> ORGANISM: Artificial Sequence
<220> FEATURE:
<223> OTHER INFORMATION: Mouse BCMA ecto domain with mouse Fc

<400> SEQUENCE: 113

```
atggcgcaac agtgtttcca cagtgaatat tttgacagtc tgctgcatgc ttgcaaaccg    60
tgtcacttgc gatgttccaa ccctcctgca acctgtcagc ttactgtgta tccaagcgtg   120
accagttcag tgaaagggac gtacacggag cccagagggc cacaatcaa gccctgtcct   180 ccatgcaaat gccagcacc taacctcttg ggtggaccat ccgtcttcat cttccctcca   240
aagatcaagg atgtactcat gatctccctg agccccatag tcacatgtgt ggtggtggat   300
```

```
gtgagcgagg atgacccaga tgtccagatc agctggtttg tgaacaacgt ggaagtacac    360
acagctcaga cacaaaccca tagagaggat tacaacagta ctctccgggt ggtcagtgcc    420
ctccccatcc agcaccagga ctggatgagt ggcaaggagt tcaaatgcaa ggtcaacaac    480
aaagacctcc cagcgcccat cgagagaacc atctcaaaac ccaagggtc agtaagagct     540 ccacaggtat atgtcttgcc tccaccagaa gagagatga ctaagaaaca ggtcactctg     600
acctgcatgg tcacagactt catgcctgaa gacatttacg tggagtggac caacaacggg    660
aaaacagagc taaactacaa gaacactgaa ccagtcctgg actctgatgg ttcttacttc    720
atgtacagca agctgagagt ggaaaagaag aactgggtgg aaagaaatag ctactcctgt    780
tcagtggtcc acgagggtct gcacaatcac cacacgacta agagcttctc ccggactccg    840
ggtaaatga                                                            849
```

<210> SEQ ID NO 114
<211> LENGTH: 282
<212> TYPE: PRT
<213> ORGANISM: Artificial Sequence
<220> FEATURE:
<223> OTHER INFORMATION: Mouse BCMA ecto domain with mouse Fc

<400> SEQUENCE: 114

```
Met Ala Gln Gln Cys Phe His Ser Glu Tyr Phe Asp Ser Leu Leu His
1               5                   10                  15

Ala Cys Lys Pro Cys His Leu Arg Cys Ser Asn Pro Pro Ala Thr Cys
                20                  25                  30

Gln Pro Tyr Cys Asp Pro Ser Val Thr Ser Ser Val Lys Gly Thr Tyr
            35                  40                  45

Thr Glu Pro Arg Gly Pro Thr Ile Lys Pro Cys Pro Pro Cys Lys Cys
        50                  55                  60

Pro Ala Pro Asn Leu Leu Gly Gly Pro Ser Val Phe Ile Phe Pro Pro
65                  70                  75                  80

Lys Ile Lys Asp Val Leu Met Ile Ser Leu Ser Pro Ile Val Thr Cys
                85                  90                  95

Val Val Val Asp Val Ser Glu Asp Asp Pro Asp Val Gln Ile Ser Trp
            100                 105                 110

Phe Val Asn Asn Val Glu Val His Thr Ala Gln Thr Gln Thr His Arg
        115                 120                 125

Glu Asp Tyr Asn Ser Thr Leu Arg Val Val Ser Ala Leu Pro Ile Gln
    130                 135                 140

His Gln Asp Trp Met Ser Gly Lys Glu Phe Lys Cys Lys Val Asn Asn
145                 150                 155                 160

Lys Asp Leu Pro Ala Pro Ile Glu Arg Thr Ile Ser Lys Pro Lys Gly
                165                 170                 175

Ser Val Arg Ala Pro Gln Val Tyr Val Leu Pro Pro Pro Glu Glu Glu
            180                 185                 190

Met Thr Lys Lys Gln Val Thr Leu Thr Cys Met Val Thr Asp Phe Met
        195                 200                 205

Pro Glu Asp Ile Tyr Val Glu Trp Thr Asn Asn Gly Lys Thr Glu Leu
    210                 215                 220

Asn Tyr Lys Asn Thr Glu Pro Val Leu Asp Ser Asp Gly Ser Tyr Phe
225                 230                 235                 240

Met Tyr Ser Lys Leu Arg Val Glu Lys Lys Asn Trp Val Glu Arg Asn
                245                 250                 255
```

```
Ser Tyr Ser Cys Ser Val Val His Glu Gly Leu His Asn His Thr
            260                 265                 270

Thr Lys Ser Phe Ser Arg Thr Pro Gly Lys
        275                 280

<210> SEQ ID NO 115
<211> LENGTH: 184
<212> TYPE: PRT
<213> ORGANISM: Artificial Sequence
<220> FEATURE:
<223> OTHER INFORMATION: human BCMA (TNFRSF17) Protein NP_001183.2

<400> SEQUENCE: 115

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 116
<211> LENGTH: 207
<212> TYPE: PRT
<213> ORGANISM: Artificial Sequence
<220> FEATURE:
<223> OTHER INFORMATION: human CD3 Epsilon Protein (>NP_000724.1 T-cell
      surface glycoprotein CD3 epsilon chain precursor

<400> SEQUENCE: 116

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
```

```
                     85                  90                  95
Val Cys Tyr Pro Arg Gly Ser Lys Pro Glu Asp Ala Asn Phe Tyr Leu
                100                 105                 110

Tyr Leu Arg Ala Arg Val Cys Glu Asn Cys Met Glu Met Asp Val Met
            115                 120                 125

Ser Val Ala Thr Ile Val Ile Val Asp Ile Cys Ile Thr Gly Gly Leu
        130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 117
<211> LENGTH: 171
<212> TYPE: PRT
<213> ORGANISM: Artificial Sequence
<220> FEATURE:
<223> OTHER INFORMATION: human CD3 Delta Protein (>NP_000723.1 T-cell
      surface glycoprotein CD3 delta chain isoform A
      precursor

<400> SEQUENCE: 117

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170

<210> SEQ ID NO 118
<211> LENGTH: 164
<212> TYPE: PRT
<213> ORGANISM: Artificial Sequence
<220> FEATURE:
<223> OTHER INFORMATION: human CD3 Zeta  Protein (>NP_932170.1 T-cell
      surface glycoprotein CD3 zeta chain isoform 1
      precursor

<400> SEQUENCE: 118
```

```
Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 119
<211> LENGTH: 182
<212> TYPE: PRT
<213> ORGANISM: Artificial Sequence
<220> FEATURE:
<223> OTHER INFORMATION: human CD3 Gamma Protein (>NP_000064.1 T-cell
      surface glycoprotein CD3 gamma chain precursor

<400> SEQUENCE: 119

Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180
```

<210> SEQ ID NO 120
<211> LENGTH: 281
<212> TYPE: PRT
<213> ORGANISM: Artificial Sequence
<220> FEATURE:
<223> OTHER INFORMATION: Human BCMA ecto.hFc Protein

<400> SEQUENCE: 120

```
Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Asp Lys Thr His Thr Cys Pro Pro Cys Pro
50                  55                  60

Ala Pro Glu Leu Leu Gly Gly Pro Ser Val Phe Leu Phe Pro Pro Lys
65                  70                  75                  80

Pro Lys Asp Thr Leu Met Ile Ser Arg Thr Pro Glu Val Thr Cys Val
                85                  90                  95

Val Val Asp Val Ser His Glu Asp Pro Glu Val Lys Phe Asn Trp Tyr
            100                 105                 110

Val Asp Gly Val Glu Val His Asn Ala Lys Thr Lys Pro Arg Glu Glu
        115                 120                 125

Gln Tyr Asn Ser Thr Tyr Arg Val Val Ser Val Leu Thr Val Leu His
    130                 135                 140

Gln Asp Trp Leu Asn Gly Lys Glu Tyr Lys Cys Lys Val Ser Asn Lys
145                 150                 155                 160

Ala Leu Pro Ala Pro Ile Glu Lys Thr Ile Ser Lys Ala Lys Gly Gln
                165                 170                 175

Pro Arg Glu Pro Gln Val Tyr Thr Leu Pro Pro Ser Arg Asp Glu Leu
            180                 185                 190

Thr Lys Asn Gln Val Ser Leu Thr Cys Leu Val Lys Gly Phe Tyr Pro
        195                 200                 205

Ser Asp Ile Ala Val Glu Trp Glu Ser Asn Gly Gln Pro Glu Asn Asn
    210                 215                 220

Tyr Lys Thr Thr Pro Pro Val Leu Asp Ser Asp Gly Ser Phe Phe Leu
225                 230                 235                 240

Tyr Ser Lys Leu Thr Val Asp Lys Ser Arg Trp Gln Gln Gly Asn Val
                245                 250                 255

Phe Ser Cys Ser Val Met His Glu Ala Leu His Asn His Tyr Thr Gln
            260                 265                 270

Lys Ser Leu Ser Leu Ser Pro Gly Lys
        275                 280
```

<210> SEQ ID NO 121
<211> LENGTH: 43
<212> TYPE: PRT
<213> ORGANISM: Artificial Sequence
<220> FEATURE:
<223> OTHER INFORMATION: Peptides 1-43 of human BCMA

<400> SEQUENCE: 121

```
Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
```

Pro Pro Leu Thr Cys Gln Arg Tyr Cys Asn Ala
          35                  40

<210> SEQ ID NO 122
<211> LENGTH: 125
<212> TYPE: PRT
<213> ORGANISM: Artificial Sequence
<220> FEATURE:
<223> OTHER INFORMATION: 21587N VH

<400> SEQUENCE: 122

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Tyr Tyr
            20                  25                  30

Tyr Trp Asn Trp Ile Arg Gln Pro Pro Gly Lys Gly Leu Glu Trp Ile
        35                  40                  45

Gly Tyr Ile Ser Tyr Ser Gly Asn Thr Asn Tyr Asn Pro Ser Leu Lys
    50                  55                  60

Ser Arg Val Thr Ile Ser Val Ala Thr Ser Arg Asn Gln Phe Ser Leu
65                  70                  75                  80

Thr Leu Ser Ser Val Thr Ala Ala Asp Thr Ala Val Tyr Tyr Cys Ala
                85                  90                  95

Arg Phe Ala Glu Tyr Cys Gly Gly Asn Ile Cys Tyr Tyr Tyr Gly Met
            100                 105                 110

Asp Val Trp Gly Gln Gly Thr Thr Val Thr Val Ser Ser
        115                 120                 125

<210> SEQ ID NO 123
<211> LENGTH: 108
<212> TYPE: PRT
<213> ORGANISM: Artificial Sequence
<220> FEATURE:
<223> OTHER INFORMATION: 21587N VL (Non-germline Cys in CDR3)

<400> SEQUENCE: 123

Glu Ile Val Leu Thr Gln Ser Pro Gly Thr Leu Ser Leu Ser Pro Gly
1               5                   10                  15

Glu Arg Ala Thr Phe Ser Cys Arg Ala Ser Gln Ser Val Gly Ser Ser
            20                  25                  30

Phe Leu Ala Trp Tyr Gln Gln Lys Pro Gly Gln Ala Pro Arg Arg Leu
        35                  40                  45

Met Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Cys Gly Gly Ser Pro
                85                  90                  95

Trp Thr Phe Gly Gln Gly Thr Lys Val Glu Ile Lys
            100                 105

<210> SEQ ID NO 124
<211> LENGTH: 127
<212> TYPE: PRT
<213> ORGANISM: Artificial Sequence
<220> FEATURE:
<223> OTHER INFORMATION: 21589N VH

<400> SEQUENCE: 124

```
Gln Val Gln Leu Val Gln Ser Gly Ala Glu Val Lys Arg Pro Gly Ser
1               5                   10                  15

Ser Val Lys Val Ser Cys Lys Ala Ser Gly Gly Thr Phe Ser Thr Tyr
                20                  25                  30

Ala Ile Asn Trp Val Arg Gln Ala Pro Gly Gln Gly Leu Glu Trp Met
            35                  40                  45

Gly Gly Ile Ile Pro Ile Phe Gly Thr Thr Asn Tyr Ala Gln Lys Phe
        50                  55                  60

Gln Gly Arg Val Thr Ile Thr Thr Asp Gly Ser Thr Thr Thr Thr Tyr
65                  70                  75                  80

Met Glu Leu Ser Ser Leu Arg Ser Glu Asp Thr Ala Val Tyr Tyr Cys
                85                  90                  95

Ala Arg Thr Val Tyr Asp Leu Asn Ser Lys Gly Tyr Tyr Tyr Tyr Tyr
            100                 105                 110

Gly Leu Asp Val Trp Gly Gln Gly Thr Thr Val Thr Val Ser Ser
            115                 120                 125

<210> SEQ ID NO 125
<211> LENGTH: 114
<212> TYPE: PRT
<213> ORGANISM: Artificial Sequence
<220> FEATURE:
<223> OTHER INFORMATION: 21589N VL

<400> SEQUENCE: 125

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
                20                  25                  30

Asp Asp Gly Asn Thr Tyr Leu Asp Trp Tyr Leu Gln Lys Pro Gly Gln
            35                  40                  45

Ser Pro Gln Leu Leu Ile Tyr Thr Leu Ser Tyr Arg Ala Ser Gly Val
        50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Ile Tyr Tyr Cys Met Gln
                85                  90                  95

Arg Ile Glu Phe Pro Ser Leu Thr Phe Gly Gly Gly Thr Lys Val Glu
            100                 105                 110

Ile Lys
```

UNITED STATES PATENT AND TRADEMARK OFFICE
CERTIFICATE OF CORRECTION

PATENT NO. : 12,258,412 B2
APPLICATION NO. : 17/828847
DATED : March 25, 2025
INVENTOR(S) : Eric Smith et al.

Page 1 of 1

It is certified that error appears in the above-identified patent and that said Letters Patent is hereby corrected as shown below:

In the Claims

Claim 7
Column 147, Line 21:
"claim 3"
Should read:
--claim 6--

Signed and Sealed this
Thirteenth Day of May, 2025

Coke Morgan Stewart
*Acting Director of the United States Patent and Trademark Office*